(12) United States Patent
Chae et al.

(10) Patent No.: US 9,760,834 B2
(45) Date of Patent: Sep. 12, 2017

(54) DISCOVERY SYSTEMS FOR IDENTIFYING ENTITIES THAT HAVE A TARGET PROPERTY

(71) Applicant: Hampton Creek, Inc., San Francisco, CA (US)

(72) Inventors: Lee Chae, San Francisco, CA (US); Josh Stephen Tetrick, San Francisco, CA (US); Meng Xu, San Francisco, CA (US); Matthew D. Schultz, San Francisco, CA (US); Chuan Wang, San Francisco, CA (US); Nicolas Tilmans, San Francisco, CA (US); Michael Brzustowicz, San Francisco, CA (US)

(73) Assignee: Hampton Creek, Inc., San Francisco, CA (US)

( * ) Notice: Subject to any disclaimer, the term of this patent is extended or adjusted under 35 U.S.C. 154(b) by 0 days.

(21) Appl. No.: 15/282,052

(22) Filed: Sep. 30, 2016

(65) Prior Publication Data

US 2017/0091637 A1    Mar. 30, 2017

Related U.S. Application Data

(60) Provisional application No. 62/235,174, filed on Sep. 30, 2015, provisional application No. 62/401,787, filed on Sep. 29, 2016.

(51) Int. Cl.
*G06N 5/04* (2006.01)
*G06N 99/00* (2010.01)

(52) U.S. Cl.
CPC .......... *G06N 5/048* (2013.01); *G06N 99/005* (2013.01)

(58) Field of Classification Search
CPC ....................................................... G06N 5/04
(Continued)

(56) References Cited

U.S. PATENT DOCUMENTS

2005/0141769 A1    6/2005   Ho et al.
2007/0275397 A1*  11/2007   Wehrman ........... C12N 15/1055
                                                    435/6.12
(Continued)

OTHER PUBLICATIONS

Thomas G. McCloud ("High Throughput Extraction of Plant, Marine and Fungal Specimens for Preservation of Biologically Active Molecules" 2010).*

(Continued)

*Primary Examiner* — Lut Wong
(74) *Attorney, Agent, or Firm* — Morgan, Lewis & Bockius LLP

(57) ABSTRACT

Systems and methods for assaying a test entity for a property, without measuring the property, are provided. Exemplary test entities include proteins, protein mixtures, and protein fragments. Measurements of first features in a respective subset of an N-dimensional space and of second features in a respective subset of an M-dimensional space, is obtained as training data for each reference in a plurality of reference entities. One or more of the second features is a metric for the target property. A subset of first features, or combinations thereof, is identified using feature selection. A model is trained on the subset of first features using the training data. Measurement values for the subset of first features for the test entity are applied to thereby obtaining a model value that is compared to model values obtained using measured values of the subset of first features from reference entities exhibiting the property.

29 Claims, 18 Drawing Sheets

(58) Field of Classification Search
USPC .......................................................... 706/45
See application file for complete search history.

(56) References Cited

U.S. PATENT DOCUMENTS

| | | |
|---|---|---|
| 2008/0281764 A1 | 11/2008 | Baxter |
| 2009/0269772 A1* | 10/2009 | Califano ............ G01N 33/5008 435/6.16 |
| 2010/0158396 A1 | 6/2010 | Wang et al. |
| 2011/0184896 A1 | 7/2011 | Guyon |
| 2011/0224913 A1 | 9/2011 | Cui et al. |
| 2015/0173394 A1 | 6/2015 | Huertas et al. |

OTHER PUBLICATIONS

G. Colebatch ("Functional genomics: tools of the trade" 2001).*
Banerjee, et al. "Food Gels: Gelling Process and New Applications", Critical Reviews in Food Science and Nutrition, (2012) vol. 52, pp. 334-346.
Boivin, et al. "Optimization of protein purification and characterization using Thermofluor screens", Protein Expression and Purification, 91 (2013) pp. 192-206.
Breiman "Bagging Predictors", Kluwer Academic Publishers, Boston, (1996) 24, pp. 123-140.
Ebden "Gaussian Processes for Regression/Classification/Dimensionality Reduction: A Quick Introduction", Aug. 2008/2015, 13 pages.
Efron, et al. "Least Angle Regression", The Annals of Statistics, 2004, vol. 32, No. 2, pp. 407-499.
Friedman, et al. "Regularization Paths for Generalized Linear Models via Coordinate Descent", Journal of Statistical Software, Jan. 2010, vol. 33, Issue 1, http://www.jstatsoft.org/, 22 pages.
Gunasekaran, et al. "Dynamic oscillatory shear testing of foods—selected applications" Trends in Food Science a& Technology, vol. 11 (2000) pp. 115-127.
Kreuziger-Keppy "Total Protein Quantitation by the Thermo Scientific Pierce 660 nm Protein Assay", Thermo Fisher Scientific, Note: 51839, 2009, 3 pages.
Kumar, et al. "What is a Good Nearest Neighbors Algorithm for Finding Similar Patches in Images?", Columbia University, University of Wisconsin-Madison, 14 pages.
Lanckriet, et al. "A statistical framework for genomic data fusion", Bioinformatics, vol. 20, No. 16 (2004), pp. 2626-2635.
Latypov, et al. "Structural and thermodynamic effects of ANS binding to human interleukin-1 receptor antagonist", Protein Science (2008), vol. 17, pp. 652-663.
Pedregosa, et al."Scikit-learn: Machine Learning in Python", Journal of Machine Learning Research, 12 (2011) pp. 2825-2830.
Pons, et al. "Instrumental Texture Profile Analysis With Particular Reference to Gelled Systems", Journal of Texture Studies, vol. 27 (1996), pp. 597-624.
Ristic, et al. "Formulation screening by differential scanning fluorimetry: how often does it work?", Structural Biology Communications, Acta Cryst. (2015), F71, pp. 1359-1364.
Rosa, et al. "Meltdown: A Tool to Help in the Interpretation of Thermal Melt Curves Acquired by Differential Scanning Fluorimetry", Journal of Biomolecular Screening, www.jbx.sagepub.com, Dec. 4, 2015, 8 pages.
Schölkopf, et al. "Kernel Principal Component Analysis", Max-Planck-Institute f. biol. Kybernetik, 6 pages.
Seabrook, et al. "High-Throughput Thermal Scanning for Protein Stability: Making a Good Technique More Robust", 2013, vol. 15, pp. 387-392.
Tabilo-Munizaga, et al. "Rheology for the food industry", Journal of Food Engineering, vol. 67 (2005), pp. 147-156.
Thannhauser, et al. "Analysis for Disulfide Bonds in Peptides and Proteins", Methods in Enzymology, vol. 143, 1987, pp. 115-119.
Van Der Wollenberg "Redundancy Analysis-An Alternative for Canonical correlation Analysis", Psychometrika, vol. 42, No. 2, Jun. 1977, pp. 207-219.
Wagstaff "Clustering with Missing Values: No Imputation Required", Jet Propulsion Laboratory, kiri.wagstaff@jpl.nasa.gov, 10 pages.
Walters, et al. "Measurement of Viscosity", Elsevier Inc. (2010), Chapter 7, pp. 69-75.
Wang, et al. "Thermal Gelation of Globular Proteins: Influence of Protein Conformation on Gel Strength", Journal of Agricultural and Food Chemistry, Mar. 1991, vol. 39, No. 3, pp. 433-438.
Winther, et al. "Quantification of thiols and disulfides", Biochimica et Biophysica Acta, 1840 (2014) pp. 838-846.
"Characterizing Protein/Ligand Binding by DSC", Calorimetry Sciences Corporation , Document No. 20111020706, Feb. 2006, 4 pages.
"Viscosity Measurement", Chapter 6, pp. 235-256.

* cited by examiner

402

A discovery system for inferentially screening a test entity to determine whether it exhibits a target property without directly measuring the test entity for the target property. The discovery system comprises at least one processor and memory addressable by the at least one processor. The memory stores at least one program for execution by the at least one processor. The at least one program comprises instructions for performing the disclosed methods.

404

Obtain a training set that comprises a plurality of reference entities and, for each respective reference entity, (i) a respective measurement of each first feature in a respective subset of first features in an N-dimensional feature space and (ii) a respective measurement of each second feature in a respective subset of an M-dimensional feature space. N is a positive integer of two or greater. M is a positive integer. The training set collectively provides at least one measurement for each first feature in the N-dimensional feature space. The training set collectively provides at least one measurement for each second feature in the M-dimensional feature space. At least one second feature in the M-dimensional feature space is a metric for the target property. The N-dimensional feature space does not include any of the second features in the M-dimensional space. The M-dimensional feature space does not include any of the first features in the N-dimensional space. The test entity comprises a protein, a fragment thereof, or a mixture of the protein with one or more other proteins.

406

The respective measurement of each first feature in the N-dimensional feature space for a single reference entity in the plurality of reference entities is obtained from a molecular assay set comprising three or more different molecular assays.

408

A plurality of first features in the N-dimensional feature space for a single reference entity in the plurality of reference entities is obtained from a single molecular assay of the reference entity.

410

Each first feature in the plurality of first features is measured using the single molecular assay under a different physical condition (e.g. pH, temperature, or concentration) of the single reference entity.

412

The respective measurement of each second feature in a respective subset of the M-dimensional feature space for a single reference entity in the plurality of reference entities is obtained from a functional assay set comprising three or more different functional assays of the single reference entity.

Fig. 4A

| Feature | Coefficients (λ @ min mse) | Coefficients (λ @ 1se) | p-value (of non-zero coefficients) |
|---|---|---|---|
| (Intercept) | 0 | 0 | - |
| Feature 1 | 1.54E-01 | 0 | < 0.01 |
| Feature 3 | 1.94E-01 | 1.86E-01 | < 0.01 |
| Feature 6 | -3.22E-01 | -2.67E-01 | < 0.01 |
| Feature 1:3:5 | -4.25E-02 | -2.06E-01 | < 0.01 |
| Feature 1:5:6 | 2.11E-01 | 1.13E-01 | < 0.01 |
| Feature 3:4:5 | 0 | -3.50E-02 | < 0.01 |
| Feature 3:5:6 | 1.96E-01 | 7.76E-02 | < 0.01 |

Fig. 7

DISCOVERY SYSTEMS FOR IDENTIFYING ENTITIES THAT HAVE A TARGET PROPERTY

CROSS REFERENCE TO RELATED APPLICATIONS

This application claims priority to U.S. Provisional Application No. 62/235,174, entitled "Machine Learning Networks for Food Application," filed Sep. 30, 2015, and U.S. Provisional Application No. 62/401,787, entitled "Systems and Methods for Identifying Entities That Have a Target Property," filed Sep. 29, 2016, each of which is hereby incorporated by reference.

TECHNICAL FIELD

The invention is directed to discovery systems that predict the suitability of test entities for food applications based in part on their basic biochemical and/or physicochemical and functional properties.

BACKGROUND

Plants consist of various organic components such as proteins, carbohydrates, lipids, natural products and metabolites. It is estimated that there are roughly 18 billion plant proteins in nature (assuming 400,000 plant species and 45,000 proteins per species). Even limiting to the roughly 20,000 varieties of cultivated plants, still yields 900 million proteins. This vast number presents a significant challenge to assaying for possible food applications, even using modern high-throughput techniques. To complicate matters, some of these compounds may be most useful in combination, resulting is a combinatorial explosion of possibilities. For instance, within the limited set of cultivated plants, there may be 405 quadrillion possible two-protein combinations and 121 octillion three-protein combinations.

Current food development methods fail to make use of satisfactory ways for efficiently screening the vast array of proteins and other compositions in plants for possible use as food ingredients. Such ingredients would be commercially useful in new or existing consumer food products. For instance, no aggregate data exist for use of plant components in food applications. Moreover, although there exist a broad array of molecular and functional assays that may be used to screen extracts from plants for possible use as food ingredients, many such assays are difficult to perform and simply cannot be feasibly used on a scale that would sample an appreciable fraction of the vast array of possible combinations of entities, such as proteins, from plants.

What is needed, therefore, are systems and methods for surveying the vast space of possible entities from plants, and for identifying desirable entities from such sources for food applications.

SUMMARY

The present disclosure addresses the need in the art for surveying the vast space of entities obtained from plants and selecting desired entities from such sources for food applications. The present disclosure makes uses of unique supervised regression models, supervised classification models and/or unsupervised models to identify features of entities that are informative of the presence, absence, or extent of a target property exhibited by an entity. A training set comprising a plurality of reference entities is trained using feature measurement data measured from the reference entities of the training set. This training set is limited in size and thus a number of molecular assays and more complex functional assays can be run on each reference entity in the training set in order to obtain values for a number of molecular features and functional features of the reference entities of the training set. The measured values for the molecular features do not directly inform whether a reference entity in the training set has a target property or the extent to which the reference entity of the training set has the target property. On the other hand, the measured values for the functional features provide a basis for determining whether the particular reference entity of the training set has the target property. For instance, in some embodiments, measured values for a functional feature across the reference entities of the training set correlate with presence, absence and/or the extent to which a member of the test population has the target property. The measured molecular and functional measurement data from each reference entity in the training set is used to train a model, using either supervised or unsupervised techniques, to thereby advantageously derive a model that identifies a relationship between at least a subset of the measured molecular features and presence, absence and/or extent to which a reference entity in the training population has the target property. Because of this, the trained model can be used to rapidly test for the presence, absence and/or extent to which a test entity has the target property. That is, a test entity can be rapidly screened for the presence, absence and/or the extent to which it possesses the target property without any requirement that the functional assays be run on the test entity. Moreover, in some embodiments, the model training incorporates data dimension reduction techniques in order to limit the number of molecular features that are used in model training, and thus the number of molecular features that need to be measured for each test entity.

In one particular embodiment, systems and methods for assaying a test entity for a target property, without measuring the property, are provided. In some embodiments, the test entity comprises a protein, protein mixture, or protein fragments. Training data is obtained comprising measurements of first features in a respective subset of an N-dimensional space, and measurements of second features in a respective subset of an M-dimensional space, for each respective reference in a plurality of reference entities. At least one of the second features serves as a metric for the target property. A subset of first features, or combinations thereof, is identified using feature selection. A model is trained on the subset of first features using the training data. Measurement values for the subset of first features for the test entity are inputted into the model to obtain a model value that is compared to model values obtained using measurements of the subset of first features from reference entities exhibiting the target property.

In another aspect, disclosed herein are methods and systems for screening plant compounds. Preferred methods provide large-scale machine learning models that predict the suitability of plant compounds for food applications based on their biochemical and/or physicochemical and functional properties. In one implementation, the methods and systems generate predicted outputs based on the inputs of preselected plant compounds (samples) in the absence of functional testing of the samples. For instance, in one embodiment, disclosed herein are methods for selecting a plant compound comprising the following steps: (i) assessing one or more biochemical and/or physicochemical properties of one or more plant compounds, (ii) determining functional properties of the one or more plant compounds for a desired food application, (iii) inputting the biochemical and/or physicochemical properties and the functional properties of the one or more plant compounds in a machine learning model, and (iv) generating a predictive output of a sample plant compound based on one or more biochemical and/or physicochemical and/or functional properties of one or more plant compounds using the machine learning model. In additional embodiments, the method further comprises selecting the predictive output of a sample plant compound as an ingredient in a food application. Preferably, the machine learning model can determine the viability or impracticalness of a sample as a replacement ingredient. More preferably, the machine learning model obviates testing for the functional properties of the sample, which can minimize time and cost for producing finished food products. Even more preferably, building and maintaining (e.g., updating) input data and output data is carried out through the use of machine learning techniques. In further aspects, the method comprises iterating the model with various combinations of plant compounds wherein the model predicts the food functional properties of a sample based on the one or more biochemical and/or physicochemical properties of numerous plant compounds.

In various embodiments, the systems and methods of the present disclosure further comprise assessing biochemical and/or physicochemical properties (first features) of an entity selected from the set comprising but not limited to: protein state, charge, stability, protein content, molecular weight (e.g., average molecular weight or molecular weight distribution), pH, solubility, protein bond interactions (e.g., this could involve interactions beyond covalent interactions—ionic, hydrophobic bonds etc.), concentration, isoelectric point, hardness, viscosity, moisture, volume, specific gravity, density, phase transition, temperature (pressure and humidity dependence thereof), extensibility, phospholipid concentration, textural features, and aggregation of the corresponding entity.

In various embodiments, the systems and methods of the present disclosure further comprise assessing and/or verifying the functional properties (second features) of an entity selected from the set comprising but not limited to: emulsification, water binding, swelling, phase separation, oil holding capacity, foaming, coalescence, gelling, film formation, gelation, caramelization, aeration, chewiness, gumminess, springiness, sensory (taste, texture, flavor, aroma, mouthfeel, aftertaste, finish, appearance), syneresis, cohesiveness, brittleness, elasticity, adhesiveness, shelf-life, color, and odor.

In yet further embodiments, the method further comprise assessing the replacement ingredient in model food systems such as in finished products and formulations. Accordingly, in various embodiments, the methods and systems of the invention can be used to identify one or more plant-derived food ingredients that have equivalent or similar characteristics to an existing food ingredient and/or identify novel food ingredients.

One aspect of the present disclosure provides a discovery system for inferentially screening a test entity to determine whether it exhibits a target property without directly measuring the test entity for the target property. The discovery system comprises at least one processor and memory addressable by the at least one processor. The memory stores at least one program for execution by the at least one processor. The at least one program comprises instructions for obtaining a training set that comprises a plurality of reference entities and, for each respective reference entity, (i) a respective measurement of each first feature in a respective subset of first features in an N-dimensional feature space and (ii) a respective measurement of each second feature in a respective subset of an M-dimensional feature space. That is, for each reference entity, one, all or some subset of all the first features in the N-dimensional feature space are measured, and one, all or some subset of second features in the M-dimensional feature space are measured. There is no requirement that the same subset of first features or the same subset of second features be measured for each reference entity and in fact, in typical embodiments, the identity of the first features in the subset of first features and the identity of the second features in the subset of second features will vary from reference entity to reference entity in the training set. Here, N is a positive integer of two or greater. Moreover, M is a positive integer. Also, the training set collectively provides at least one measurement for each first feature in the N-dimensional feature space. Furthermore, the training set collectively provides at least one measurement for each second feature in the M-dimensional feature space. Thus, although the same subset of features need not be measured for each reference entity in the training set, collectively there is at least one measurement of each first feature in the N-dimensional space and at least one measurement of each second feature in the M-dimensional space. In some embodiments, collectively there are at least two measurements, at least three measurements, at least four measurements, at least five measurements or at least six measurements of each first feature in the N-dimensional space and at least one measurement of each second feature in the M-dimensional space.

At least one second feature in the M-dimensional feature space is a metric for the target property. Further, the N-dimensional feature space does not include any of the second features in the M-dimensional space and the M-dimensional feature space does not include any of the first features in the N-dimensional space.

In typical embodiments, the test entity comprises a protein, a fragment thereof, or a mixture of the protein with one or more other proteins. However, the present disclosure is not so limited, and in some embodiments the test entity alternatively comprises one or more different organic molecules derived from living organisms such as protein (e.g., unmodified protein, sulfated, acylated or glycosylated protein, non-ribosomal peptide), amino acids, one or more different oils (e.g., triglyceride, sterols and other neutral lipids), one or more different polar lipids (e.g., phospholipids, glycolipids, sphingolipids), one or more different carbohydrates (e.g., polysaccharide, oligosaccharide, disaccharide, monosaccharide, etc.), one or more different sugar alcohols, one or more different phenols, one or more different polyphenols, one or more different nucleic acids, one or more different polynucleic acids, one or more different polyketides, one or more different xenobiotic compounds, combinations and covalently-bound combinations thereof (e.g., glycosidic protein or protein-bound lipid), and/or mixtures thereof (e.g., an oil and a phospholipid, etc.). In some embodiments, the test entity comprises two or more different organic molecules derived from living organisms such as protein (e.g., unmodified protein, sulfated, acylated or glycosylated protein, non-ribosomal peptide), two or more different amino acids, two or more different oils (e.g., triglyceride, sterols and other neutral lipids), two or more different polar lipids (e.g., phospholipids, glycolipids, sphingolipids), two or more different carbohydrates (e.g., polysaccharide, oligosaccharide, disaccharide, monosaccharide), two or more different sugar alcohols, two or more different phenols, two or more different polyphenols, two or more different nucleic acids, two or more different polynucleic acids, two or more different polyketides, two or more different xenobiotic compounds, two or more different combinations and covalently-bound combinations thereof (e.g., glycosidic protein or protein-bound lipid), and/or two or more different mixtures thereof (e.g., an oil and a phospholipid, etc.).

The at least one program further comprises instructions for identifying two or more first features, or one or more combinations thereof, in the N-dimensional feature space using a feature selection method and the training set, thereby selecting a set of first features $\{p_1, \ldots, p_{N-K}\}$ from the N-dimensional feature space, where N–K is a positive integer less than N. The at least one program further comprises instructions for training a model using measurements for the set of first features $\{p_1, \ldots, p_{N-K}\}$ across the training set, thereby obtaining a trained model. The at least one program further comprises instructions for obtaining measurement values for the set of first features $\{p_1, \ldots, p_{N-K}\}$ of the test entity and inputting them into the trained model thereby obtaining a trained model output value for the test entity. The at least one program further comprises instructions for comparing the trained model output value of the test entity to one or more trained model output values computed using measurement values for the set of first features $\{p_1, \ldots, p_{N-K}\}$ of one or more reference entities that exhibits the target property, thereby determining whether the test entity exhibits the target property. In this way, advantageously, the test entity is screened to determine whether, and/or to what extent, the test entity exhibits the target property without any requirement that the test entity be measured for the second features.

In some embodiments, the trained model is a linear regression model of the form:

$$f(X) = \beta_0 + \Sigma_{j=1}^{t} X_j \beta_j$$

where t is a positive integer, f(X) are the measurements for a second feature in the M-dimensional feature space across the training set, $\beta_0, \beta_1, \ldots, \beta_t$ are parameters that are determined by the training of the model, and each $X_j$ in $\{X_1, \ldots, X_t\}$ is a first feature $p_i$ in the set of first features $\{p_1, \ldots, p_{N-K}\}$ of the training set, a transformation of the first feature $p_i$, a basis expansion of the first feature $p_i$, or an interaction between two or more features in the set of first features $\{p_1, \ldots, p_{N-K}\}$. In some such embodiments, at least one $X_j$ in $\{X_1, \ldots, X_t\}$ represents an interaction between two or more features in the set of first features $\{p_1, \ldots p_{N-K}\}$. In some embodiments, $\{X_1, \ldots, X_t\}$ is determined by the identifying of the two or more first features, or one or more combinations thereof, as described above, or the training of the model, as described above, from the N-dimensional feature space using a subset selection or shrinkage method.

In some alternative embodiments, the trained model is a nonlinear regression model. In some embodiments, the target second feature 212 for the regression training set comprises a plurality of subgroups (e.g., two or more, three or more trait subgroups, four or more specific trait subgroups, etc.). These subgroups can correspond to perceived differences in a target property (e.g., sour, sweet, bitter, etc.) In some embodiments, a generalization of the logistic regression model that handles multicategory responses can be used to develop a model 214 that discriminates between the various subgroups found in the training set 206. For example, measured data for selected first features 210 can be applied to any of the multi-category logit models described in Agresti, *An Introduction to Categorical Data Analysis*, 1996, John Wiley & Sons, Inc., New York, Chapter 8, hereby incorporated by reference in its entirety, in order to develop a model 214 capable of discriminating between any of a plurality of categories of a second feature 212 represented in the training set 206.

In some embodiments, the trained model is a clustering applied to the measurements for the set of first features $\{p_1, \ldots, p_{N-K}\}$ across the training set without use of respective measurements of each second feature in the M-dimensional feature space. In such embodiments, the inputting the set of first features $\{p_1, \ldots, p_{N-K}\}$ of the test entity into the trained model described above comprises clustering the set of first features $\{p_1, \ldots, p_{N-K}\}$ of the test entity together with the measurements for the set of first features $\{p_1, \ldots, p_{N-K}\}$ across the training set, and the comparing the trained model output value of the test entity to one or more trained model output values described above comprises determining whether the set of first features $\{p_1, \ldots, p_{N-K}\}$ of the test entity co-clusters with the set of first features $\{p_1, \ldots, p_{N-K}\}$ of one or more reference entities in the training set that exhibit the target property. In some such embodiments, this clustering comprises unsupervised clustering.

In some embodiments, the model used is a k-nearest neighbors classifier and the inputting the set of first features $\{p_1, \ldots, p_{N-K}\}$ of the test entity into the trained model and the comparing the trained model output value of the test entity to one or more trained model output values computed using measurement values for the set of first features $\{p_1, \ldots, p_{N-K}\}$ of one or more reference entities comprises obtaining the trained model output value as the outcome of the set of first features $\{p_1, \ldots, p_{N-K}\}$ of the test entity against the k nearest neighbors of the test entity in the training set using the trained k-nearest neighbors classifier, and the k nearest neighbors of the test entity includes one or more reference entities that exhibit the target property.

In some embodiments, the model is a support vector machine.

In some embodiments, the respective measurement of each first feature in a respective subset of first features in the N-dimensional feature space for each corresponding reference entity in the training set is taken when the corresponding reference entity is in the form of an emulsion or a liquid, and the set of first features $\{p_1, \ldots, p_{N-K}\}$ comprises protein concentration, hydrophobicity, or phospholipid concentration of the corresponding reference entity.

In some embodiments, the respective measurement of each first feature in a respective subset of first features in the N-dimensional feature space for each corresponding reference entity in the training set is taken when the corresponding reference entity is in the form of an emulsion or a liquid, and the set of first features $\{p_1, \ldots, p_{N-K}\}$ comprises all or a subset of protein state, charge, stability, protein content, molecular weight (e.g., average molecular weight or molecular weight distribution), pH, solubility, protein bond interactions (e.g., this could involve interactions beyond covalent interactions—ionic, hydrophobic bonds etc.), concentration, isoelectric point, hardness, viscosity, moisture content, volume, specific gravity, density, phase transition, temperature (pressure and humidity dependence thereof), extensibility, phospholipid concentration, a textural feature, and aggregation of the corresponding entity.

In some embodiments, the respective measurement of each first feature in a respective subset of first features in the N-dimensional feature space for each corresponding reference entity in the training set is taken when the corresponding reference entity is in the form of an emulsion or a liquid, and the set of first features $\{p_1, \ldots, p_{N-K}\}$ comprises an amount of inter- and intra-molecular bonding within the corresponding reference entity.

In some embodiments, the training a model using measurements for the set of first features $\{p_1, \ldots, p_{N-K}\}$ across the training set, thereby obtaining a trained model described above, further comprises training the model using measurements of each corresponding reference entity in the training set for a single second feature selected from the group consisting of dye penetration, viscosity, gelation, texture, angled layering, layer strength, flow consistency, and gelling speed.

In some embodiments, the training a model using measurements for the set of first features $\{p_1, \ldots, p_{N-K}\}$ across the training set, thereby obtaining a trained model described above, further comprises training the model using measurements of each corresponding reference entity in the training set for a single second feature that is hardness, fracturability, cohesiveness, springiness, chewiness, or adhesiveness as determined by a texture profile analysis assay.

In some embodiments, N is 10 or more, and N–K is 5 or less. In some embodiments, N is 35 or more, M is 60 or more, and N–K is 10 or less. In some embodiments, N is 200 or more, and N–K explains (accounts for) at least sixty percent, at least seventy percent, or at least eighty percent of the variance of a single second feature across the training set.

In some embodiments, the respective measurement of each first feature in the N-dimensional feature space for a single reference entity in the plurality of reference entities is obtained from a molecular assay set comprising three or more different molecular assays.

In some embodiments, a plurality of first features in the N-dimensional feature space for a single reference entity in the plurality of reference entities is obtained from a single molecular assay of the reference entity. In some such embodiments, each first feature in the plurality of first features is measured using the single molecular assay under a different physical condition (e.g., pH, temperature, or concentration of the first entity).

In some embodiments, the respective measurement of each second feature in the M-dimensional feature space for a single reference entity in the plurality of reference entities is obtained from a functional assay set comprising three or more different functional assays of the single reference entity.

In some embodiments, a plurality of second features in the M-dimensional feature space for a single reference entity in the plurality of reference entities is obtained from a single functional assay. In some such embodiments, each second feature in the plurality of second features is measured using the single functional assay under a different physical condition (e.g., pH, temperature, or concentration of the second entity).

In some embodiments, the test entity consists of the protein or the peptide in a solution.

In some embodiments, the feature selection method comprises regularization (e.g., using Lasso, LARS, or Elastic net) across the training set using the N-dimensional feature space and a single second feature in the M-dimensional feature space.

In some embodiments, the feature selection method comprises application of random forest regression to the training set using the N-dimensional feature space and all or a portion of the M-dimensional feature space.

In some embodiments, the feature selection method comprises application of Gaussian process regression to the training set using the N-dimensional feature space and a single second feature in the M-dimensional feature space.

In some embodiments, the feature selection method comprises application of principal component analysis to the training set thereby identifying a plurality of principal components where the plurality of principal components collectively represent the set of first features $\{p_1, \ldots, p_{N-K}\}$ from the M-dimensional feature space across the training set. In some such embodiments, the training of the model using measurements for the set of first features $\{p_1, \ldots, p_{N-K}\}$ and measurements for the one or more second features across the training set comprises training the model using the plurality of principal components samples for each reference entity in the plurality of reference entities and measurements for one or more second features in each reference entity in the training set. In some such embodiments, the model is a support vector machine.

In some embodiments, a plurality of first features in the N-dimensional feature space is obtained from a molecular assay of each reference entity in the training set and the feature selection method comprises application of a kernel function to the respective measurement of each measured first feature in the plurality of first features in the N-dimensional feature space for each reference entity in the plurality of reference entities thereby deriving a kernel matrix. Then, principal component analysis is applied to the kernel matrix to identify a plurality of principal components that collectively represent the set of first features $\{p_1, \ldots, p_{N-K}\}$ from the N-dimensional feature space. In such embodiments, the training of the model using measurements for the set of first features $\{p_1, \ldots, p_{N-K}\}$ across the training set comprises training the model using the plurality of principal components samples for each reference entity in the plurality of reference entities. In some such embodiments, the model is a support vector machine.

In some embodiments, a first plurality of first features in the N-dimensional feature space is obtained from a first molecular assay of each reference entity in the training set and a second plurality of first features in the N-dimensional feature space is obtained from a second molecular assay of each reference entity in the training set. In such embodiments, the feature selection method comprises (i) application of a first kernel function to the respective measurement of each measured first feature in the first plurality of first features in the N-dimensional feature space for each reference entity in the plurality of reference entities, thereby deriving a first kernel matrix, (ii) application of a second kernel function to the respective measurement of each measured first feature in the second plurality of first features in the N-dimensional feature space for each reference entity in the plurality of reference entities, thereby deriving a second kernel matrix, and (iii) applying principal component analysis to the first kernel matrix and the second the kernel matrix to thereby identifying a plurality of principal components that collectively represent the set of first features $\{p_1, \ldots, p_{N-K}\}$ from the N-dimensional feature space. In such embodiments, the training the model using measurements for the set of first features $\{p_1, \ldots, p_{N-K}\}$ across the training set comprises training the model using the plurality of principal components samples for each reference entity in the plurality of reference entities. In some such embodiments, the model is a support vector machine.

In some embodiments, the test entity originates from a member of the Plant Kingdom.

In some embodiments, the test entity is extracted from a plant, and the at least one program further comprises instructions for associating one or more data structures with the test entity, and the one or more data structures identify the test entity, an extraction parameter for the test entity, and a characteristic of the plant. In some such embodiments, the extraction parameter is (i) an elution pH or time and a predetermined purification column for the test entity, (ii) a buffer type used to extract the test entity from the plant, (iii) a specific pH or pH range used to extract the test entity from the plant, (iv) a specific ionic strength or an ionic strength range used to extract the test entity from the plant, or (v) a specific temperature or temperature range used to extract the test entity from the plant. In some such embodiments, the one or more data structures comprises at least three extraction parameters used to extract the test entity from the plant selected from the group consisting of: (i) an elution pH or time and a predetermined purification column for the test entity, (ii) a buffer type used to extract the test entity from the plant, (iii) a specific pH or pH range used to extract the test entity from the plant, (iv) a specific ionic strength or an ionic strength range used to extract the test entity from the plant, or (v) a specific temperature or temperature range used to extract the test entity from the plant. In some such embodiments, the characteristic of the plant is a plant taxonomy feature. In some such embodiments, the plant taxonomy feature is a family name of the plant, a genus of the plant, a species of the plant, a subspecies name of the plant, a varietal of the plant, or a forma of the plant. In some such embodiments, the one or more data structures comprises at least three characteristics of the plant selected from the group consisting of a plural family name of the plant, a genus of the plant, a species of the plant, a subspecies name of the plant, a varietal of the plant, a forma of the plant, a harvesting date of the plant, an arrival date of the plant, a source geographic origin of the plant, or a physical form of the plant. In some such embodiments, the one or more data structures specify a material characteristic (e.g., harvesting date of the test entity, an arrival date of the test entity, a geographic origin of the test entity, a form of the test entity, a particle size of the test entity, a vendor of the test entity, or a volume of the test entity) of the test entity. In some such embodiments, the one or more data structures comprises at least two characteristics of the test entity selected from the group consisting of a harvesting date of the test entity, an arrival date of the test entity, a geographic origin of the test entity, a form of the test entity, a particle size of the test entity, a vendor of the test entity, or a volume of the test entity.

In some embodiments, the test entity consists of the protein. In alternative embodiments, the test entity comprises a mixture of two or more proteins from a single plant species. In still other embodiments, the test entity comprises a mixture of five or more proteins from a single plant species. In still other embodiments, the test entity comprises a mixture of five or more proteins from two or more plant species. In still other embodiments, test entity comprises a mixture of five or more proteins from three or more plant species. In still other embodiments, the test entity comprises a mixture of ten or more proteins from five or more plant species. In embodiments where the test entity consists of or comprises one or more proteins, the one or more proteins may be in solution.

In some embodiments, the protein is from an Angiosperm, Gymnosperm, Pteridophyte, Bryopyte, or Algae. In some embodiments, the protein is from a Fabeaceae, Poaceae, Brassicaceae, Apiaceae, Solanaceae, Cucurbitaceae, Rosaceae, Algae, Anacardiaceae, Amaranthaceae, Lauraceae, Linaceae, Cannabaceae, or Piperaceae. In some embodiments, the protein is from a Fungi.

In some embodiments, after a model is trained, the model is used to evaluate each test entity in a plurality of test entities using the techniques disclosed above, where at least some of the respective test entities in the plurality of test entities comprise a different protein, a different fragment thereof, or a mixture of the different proteins with one or more other proteins. In some such embodiments, the plurality of test entities comprises more than 50 different test entities each from a single plant species. In some such embodiments, the plurality of test entities comprises more than 100 different test entities each from a single plant species. In some such embodiments, the plurality of test entities comprises more than 200 different test entities each from a single plant species. In some such embodiments, the plurality of test entities comprises more than 300 different test entities each from a single plant species.

In some embodiments, a first subset of the plurality of reference entities do not exhibit the target property or exhibit the target property to a lesser degree than a second subset of the plurality of reference entities.

In some embodiments, a representation of the training set as a matrix of the plurality of reference entities against the N-dimensional feature space and the M-dimensional feature space has a sparseness of 90 percent or greater or a sparseness of 99 percent or greater.

Another aspect of the present disclosure provides a method for inferentially screening a test entity to determine whether it exhibits a target property without directly measuring the test entity for the target property. The method comprises obtaining a training set that comprises a plurality of reference entities and, for each respective reference entity, (i) a respective measurement of each first feature in a respective subset of first features in an N-dimensional feature space and (ii) a respective measurement of each second feature in a respective subset of an M-dimensional feature space, wherein N is a positive integer of two or greater, M is a positive integer, the training set collectively provides at least one measurement for each first feature in the N-dimensional feature space, the training set collectively provides at least one measurement for each second feature in the M-dimensional feature space, at least one second feature in the M-dimensional feature space is a metric for the target property, the N-dimensional feature space does not include any of the second features in the M-dimensional space, the M-dimensional feature space does not include any of the first features in the N-dimensional space, and the test entity comprises a protein, a first fragment thereof, or a mixture of the protein with one or more other proteins.

In the method, two or more first features, or one or more combinations thereof, in the N-dimensional feature space are identified using a feature selection method and the training set, thereby selecting a set of first features $\{p_1, \ldots, p_{N-K}\}$ from the N-dimensional feature space, wherein N–K is a positive integer less than N.

In the method, a model is trained using measurements for the set of first features $\{p_1, \ldots, p_{N-K}\}$ across the training set, thereby obtaining a trained model. In the method, measurement values are obtained for the set of first features $\{p_1, \ldots, p_{N-K}\}$ of the test entity and inputted into the trained model thereby obtaining a trained model output value for the test entity. In the method, the trained model output value of the test entity is compared to one or more trained model output values computed using measurement values for the set of first features $\{p_1, \ldots, p_{N-K}\}$ of one or more reference entities that exhibits the target property, thereby determining whether the test entity exhibits the target property.

BRIEF DESCRIPTION OF THE DRAWINGS

FIG. 4A, FIG. 4B, FIG. 4C, FIG. 4D, FIG. 4E, FIG. 4F, FIG. 4G, and FIG. 4H collectively provide a flowchart for inferentially screening a test entity to determine whether it exhibits a target property without directly measuring the test entity for the target property, where optional elements of the flow chart are indicated by dashed boxes, in accordance with various embodiments of the present disclosure.

FIG. 7 illustrates regression coefficients for a model trained to identify protein gelling ability without any requirement for the direct measurement of protein gelling as well as p-values that represent their statistical significance, in accordance with an embodiment of the present disclosure.

Like reference numerals refer to corresponding parts throughout the several views of the drawings.

DETAILED DESCRIPTION

Figure 1:
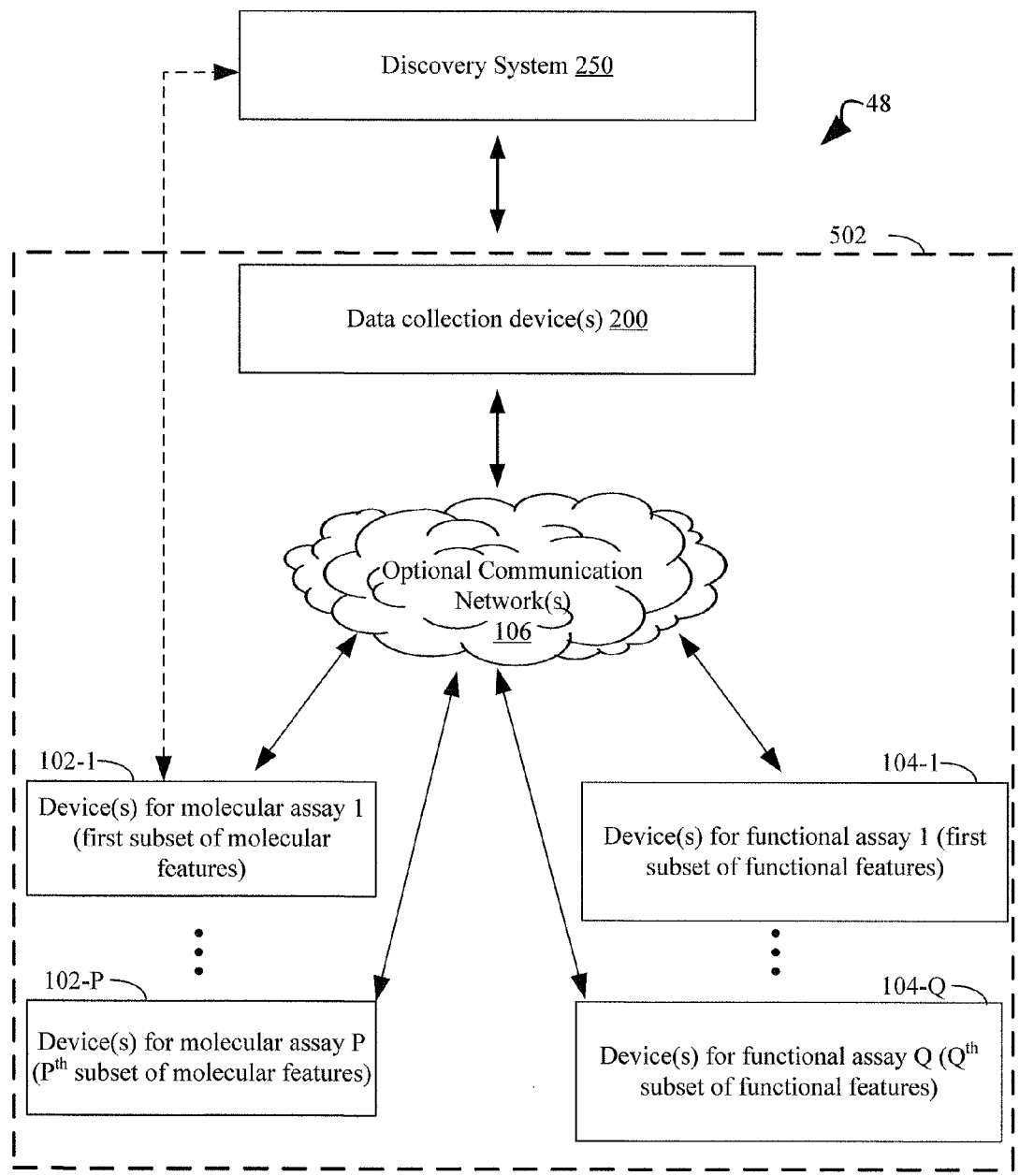
FIG. 1 illustrates an exemplary system topology for a discovery system for inferentially screening a test entity to determine whether it exhibits a target property without directly measuring the test entity for the target property, in accordance with an embodiment of the present disclosure.

Systems and methods are provided for assaying a test entity for a property of interest ("target property"), without measuring the property of interest. In some embodiments, the test entity comprises a protein, protein mixture, or protein fragments. Training data is obtained comprising measurements of first features in a respective subset of an N-dimensional space and measurements of second features in a respective subset of an M-dimensional space, for each respective reference in a plurality of reference entities. At least one of the second features serves as a metric for the target property. A subset of first features, or combinations thereof, is identified using feature selection and the training data. At least one model is trained on the subset of first features using the training data. Measurement values for the subset of first features for the test entity are inputted into the model to obtain a model value that is compared to model values obtained using measurements of the subset of first features from reference entities exhibiting the property of interest.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, and networks have not been described in detail so as not to unnecessarily obscure aspects of the embodiments.

It will also be understood that, although the terms "first", "second", etc. may be used herein to describe various elements, these elements should not be limited by these terms. These terms are only used to distinguish one element from another. For example, a "first subject" could be termed a "second subject", and, similarly, a "second subject" could be termed a "first subject" without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
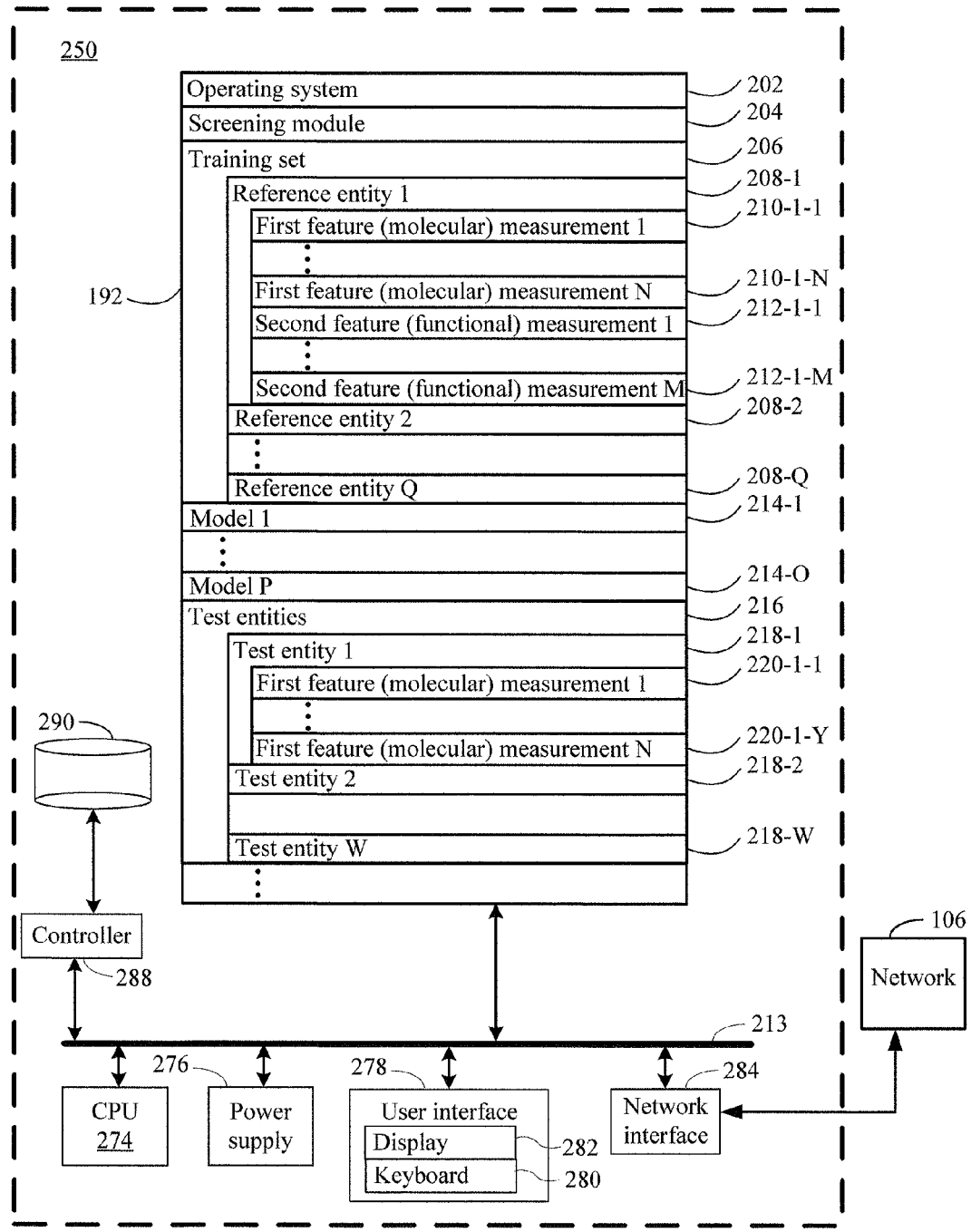
FIG. 2 illustrates a discovery system for inferentially screening a test entity to determine whether it exhibits a target property without directly measuring the test entity for the target property, in accordance with an embodiment of the present disclosure.
Figure 3:
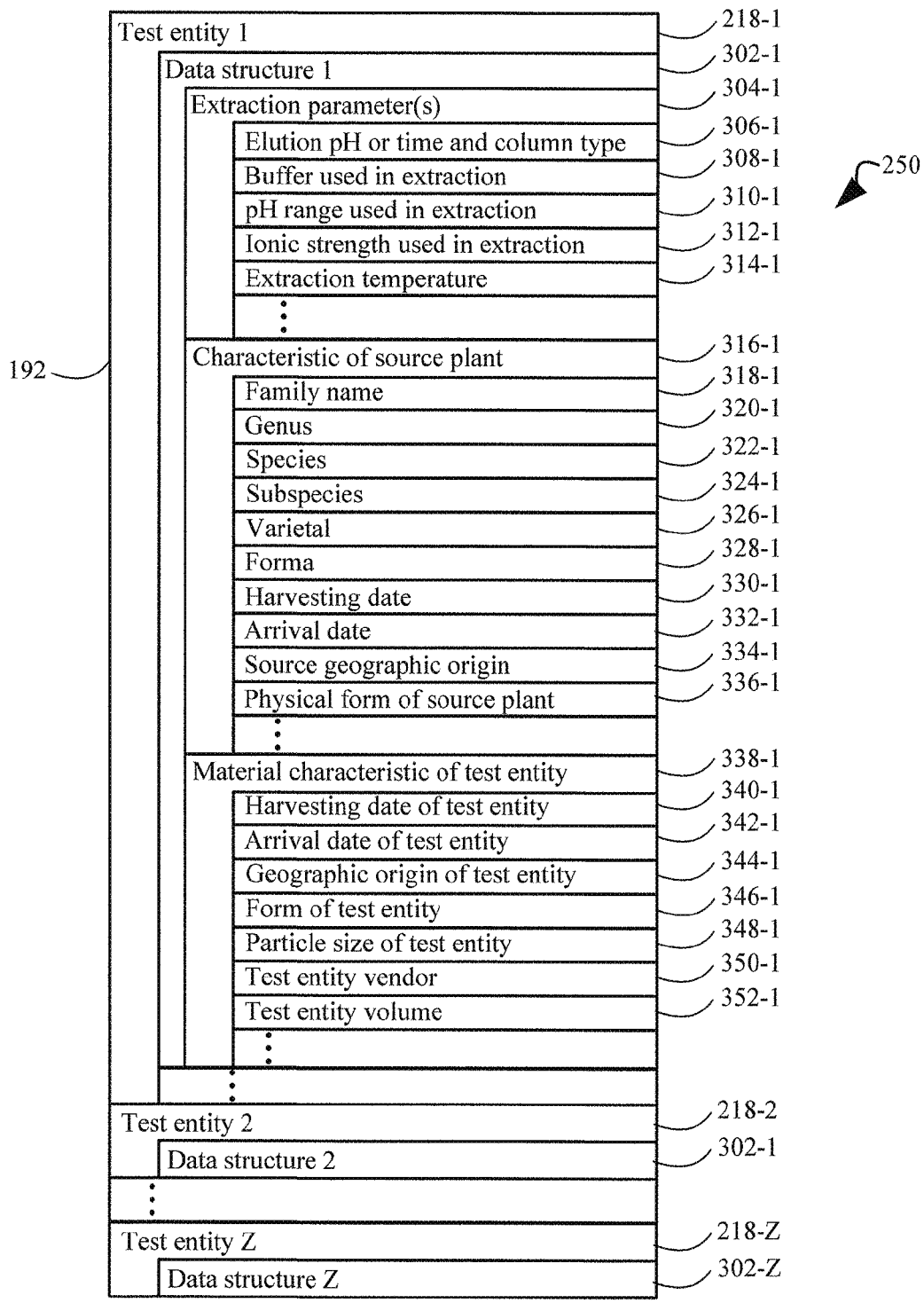
FIG. 3 illustrates exemplary data structures, in accordance with an embodiment of the present disclosure.

A detailed description of a system 48 for inferentially screening a test entity to determine whether it exhibits a target property without directly measuring the test entity for the target property in accordance with the present disclosure is described in conjunction with FIGS. 1 through 3. As such, FIGS. 1 through 3 collectively illustrate the topology of the system in accordance with the present disclosure. In the topology, there is a discovery system for inferentially screening a test entity to determine whether it exhibits a target property without directly measuring the test entity for the target property ("discovery system 250") (FIGS. 1, 2, and 3), one or more data collection devices 200, devices for one or more molecular assays 102, and devices for one or more functional assays 104 (FIG. 1). Throughout the present disclosure, the data collection devices 200 and the discovery system 250 will be referenced as separate devices solely for purposes of clarity. That is, the disclosed functionality of the data collection device 200 and the disclosed functionality of the discovery system 250 are contained in separate devices as illustrated in FIG. 1. However, it will be appreciated that, in fact, in some embodiments, the disclosed functionality of the one or more data collection devices 200 and the disclosed functionality of the discovery system 250 are contained in a single device. Likewise, in some embodiments the data collection device 200 and the devices for molecular assays 102 and/or the devices for functional assays 104 are the same devices.

Referring to FIG. 1, the discovery system 250 inferentially screens a test entity to determine whether it exhibits a target property without directly measuring the test entity for the target property. To do this, the data collection device 200, which is in electrical communication with the discovery system 250, receives a training set that comprises a plurality of reference entities and, for each respective reference entity, (i) a respective measurement of each first feature in a respective subset of first features in an N-dimensional feature space from the one or more devices 102 for molecular assays and (ii) a respective measurement of each second feature in a respective subset of an M-dimensional feature space from the one or more devices 104 for functional assays. In some embodiments, the data collection device 200 receives such data directly from the device(s) 102 and the device(s) 104. For instance, in some embodiments the data collection device 200 receives this data wirelessly through radio-frequency signals. In some embodiments such signals are in accordance with an 802.11 (WiFi), Bluetooth, ZigBee, or by RFID communication. In some embodiments, the data collection device 200 receives such data directly, analyzes the data, and passes the analyzed data to the discover system 250.

In some embodiments, the data collection device 200 and/or the discovery system 250 is not proximate to the devices 102 and/or devices 104 and/or does not have direct wireless capabilities or such wireless capabilities are not used for the purpose of acquiring training data. In such embodiments, a communication network 106 may be used to communicate measurements of first features and second features from the sensors 102 and the sensors 104 to the data collection device 200 and/or the discovery system 250.

Examples of networks 106 include, but are not limited to, the World Wide Web (WWW), an intranet and/or a wireless network, such as a cellular telephone network, a local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more devices for molecular assays 102 and the one or more devices for functional assays 104 may wirelessly transmit information directly to the data collection device 200 and/or discovery system 250. Further, the data collection device 200 and/or the discovery system 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the discovery system 250 comprises one or more computers. For purposes of illustration in FIG. 2, the discovery system 250 is represented as a single computer that includes all of the functionality for inferentially screening a test entity to determine whether it exhibits a target property without directly measuring the test entity for the target property. However, the disclosure is not so limited. In some embodiments, the functionality for inferentially screening a test entity to determine whether it exhibits a target property without directly measuring the test entity for the target property is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary discovery system 250 for inferentially screening a test entity to determine whether it exhibits a target property without directly measuring the test entity for the target property comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the discovery system 250 but that can be electronically accessed by the discovery system 250 over an Internet, intranet, or other form of network or electronic cable (illustrated as element 106 in FIG. 2) using network interface 284.

In some embodiments, the memory 192 of the discovery system 250 for inferentially screening a test entity to determine whether it exhibits a target property without directly measuring the test entity for the target property stores:

- an operating system 202 that includes procedures for handling various basic system services;
- a screening module 204;
- a training set 206, that comprises a plurality of reference entities and, for each respective reference entity 208, (i) a respective measurement of each first feature 210 in a respective subset of first features in an N-dimensional feature space and (ii) a respective measurement of each second feature 212 in a respective subset of an M-dimensional feature space, where N is a positive integer of two or greater, M is a positive integer, and where the training set collectively provides at least one measurement for each first feature in the N-dimensional feature space and at least one measurement for each second feature in the M-dimensional feature space, and where at least one second feature in the M-dimensional feature space is a metric for the target property;
- one or more models 214 for assessing whether a test entity exhibits the target property; and
- data for one or more test entities 218, the data including a set of measurements of first features 220 in the N-dimensional space.

In some embodiments, the screening module 204 is accessible within any browser (phone, tablet, laptop/desktop). In some embodiments, the screening module 204 runs on native device frameworks, and is available for download onto the discovery system 250 running an operating system 202 such as Android or iOS.

Referring to FIG. 3, in some embodiments, one or more data structures 302 are associated with a test entity 218. For instance, in some such embodiments, the test entity is extracted from a plant and the one or more data structures associated with the test entity identify the test entity, one or more extraction parameter(s) 304 for the test entity, one or more characteristic(s) of the source plant 316 from which the test entity 218 was extracted, and/or a material characteristic 338 of the test entity 218.

In some such embodiments, the extraction parameter 304 is (i) an elution pH or time and a predetermined purification column 304 for the test entity, (ii) a buffer type 308 used to extract the test entity 218 from the plant, (iii) a specific pH or pH range 310 used to extract the test entity from the plant, (iv) a specific ionic strength or an ionic strength range 312 used to extract the test entity from the plant, or (v) a specific temperature or temperature range 314 used to extract the test entity from the plant.

In some such embodiments, the characteristic 316 of the source plant is a plant taxonomy feature. In some such embodiments, the plant taxonomy feature is a family name 318 of the source plant, a genus 320 of the source plant, a species 322 of the source plant, a subspecies name 324 of the source plant, a varietal 326 of the source plant, or a forma 328 of the source plant. In some embodiments the characteristic 316 of the source plant is a harvesting date 330 of the source plant, an arrival date 332 of the source plant, a source geographic origin 334 of the plant, or a physical form 336 of the source plant.

In some such embodiments, the material characteristic 338 of the test entity is a harvesting date of the test entity 340, an arrival date of the test entity 342, a geographic origin of the test entity 344, a form of the test entity 346, a particle size of the test entity 348, a vendor of the test entity 350, or a volume of the test entity 352. In some such embodiments, the one or more data structures comprises at least two characteristics of the test entity selected from the group consisting of a harvesting date of the test entity, an arrival date of the test entity, a geographic origin of the test entity, a form of the test entity, a particle size of the test entity, a vendor of the test entity, or a volume of the test entity.

In some implementations, one or more of the above identified data elements or modules of the discovery system 250 for inferentially screening a test entity to determine whether it exhibits a target property without directly measuring the test entity for the target property are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments, the memory 192 and/or 290 stores additional modules and data structures not described above.

In some embodiments, a discovery system 250 for inferentially screening a test entity to determine whether it exhibits a target property without directly measuring the test entity for the target property is a smart phone (e.g., an iPHONE), laptop, tablet computer, desktop computer, or other form of electronic device (e.g., a gaming console). In some embodiments, the discovery system 250 is not mobile. In some embodiments, the discovery system 250 is mobile.

In some embodiments the discovery system 250 is a tablet computer, desktop computer, or other form or wired or wireless networked device. In some embodiments, the discovery system 250 has any or all of the circuitry, hardware components, and software components found in the discovery system 250 depicted in FIG. 2 or 3. In the interest of brevity and clarity, only a few of the possible components of the discovery system 250 are shown in order to better emphasize the additional software modules that are installed on the discovery system 250.

Now that details of a system 48 for inferentially screening a test entity to determine whether it exhibits a target property without directly measuring the test entity for the target property have been disclosed, details regarding a flow chart of processes and features of the system, in accordance with an embodiment of the present disclosure, are disclosed with reference to FIGS. 4A through 4G. In some embodiments, such processes and features of the system are carried out by the screening module 204 illustrated in FIG. 2.

Block 402. With reference to block 402 of FIG. 4A, a discovery system 250 for inferentially screening a test entity 218 to determine whether it exhibits a target property without directly measuring the test entity for the target property is provided. The discovery system comprises at least one processor 274 and memory 192/290 addressable by the at least one processor. The memory stores at least one program for execution by the at least one processor. The at least one program comprises instructions for performing the disclosed methods.

Block 404. With reference to bock 404 of FIG. 4A, a training set that comprises a plurality of reference entities is obtained. In some embodiments, the plurality of reference entities consists of between 5 and 1000 reference entities, between 5 and 500 reference entities, or between 5 and 250 reference entities. In some embodiments, the plurality of reference entities comprises 10 or more reference entities, 30 or more reference entities, 50 or more reference entities, 75 or more reference entities, 100 or more reference entities, 200 or more reference entities, or 300 or more reference entities.

Figure 10:
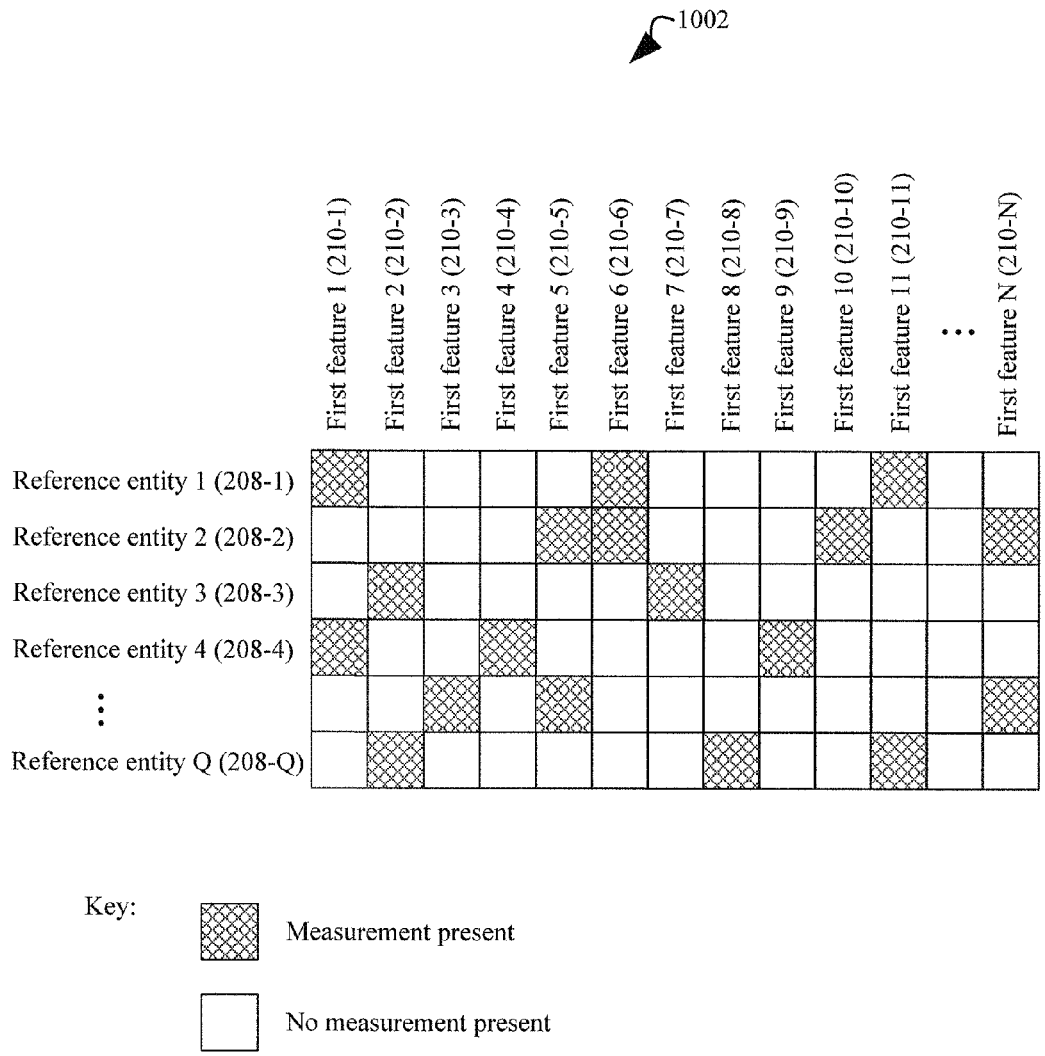
FIG. 10 illustrates how reference entities of a training set include certain measurements of first features in an N-dimensional feature space in accordance with an embodiment of the present disclosure.

For each respective reference entity 208 in the training set 206 comprises a respective measurement of each first feature 210 in a respective subset of first features in an N-dimensional feature space. Here, N is a positive integer of two or greater. There is no requirement that each respective entity 208 include a measurement for each of the first features 210 in the N-dimensional feature space, as FIG. 10 illustrates. Reference entity 208-1 includes measurements for first features 210-1, 210-6, and 210-11 whereas reference entity 208-2 includes measurements for first features 210-5, 210-6, 210-10, and 210-N. Thus, reference entity 208-1 includes a respective measurement of each first feature 210 in a first subset of first features in the N-dimensional feature space (first features 210-1, 210-6, and 210-11) and reference entity 208-2 includes a respective measurement of each first feature 210 in a second subset of first features in the N-dimensional feature space (first features 210-5, 210-6, 210-10, and 210-N), where the first and second subsets are not necessarily the same and in fact are different in this example.

In some embodiments, N is an integer of 10 or more, 30 or more, 50 or more, 75 or more, 100 or more, 200 or more, or 300 or more, 500 or more, 1000 or more, or 2000 or more.

Figure 11:
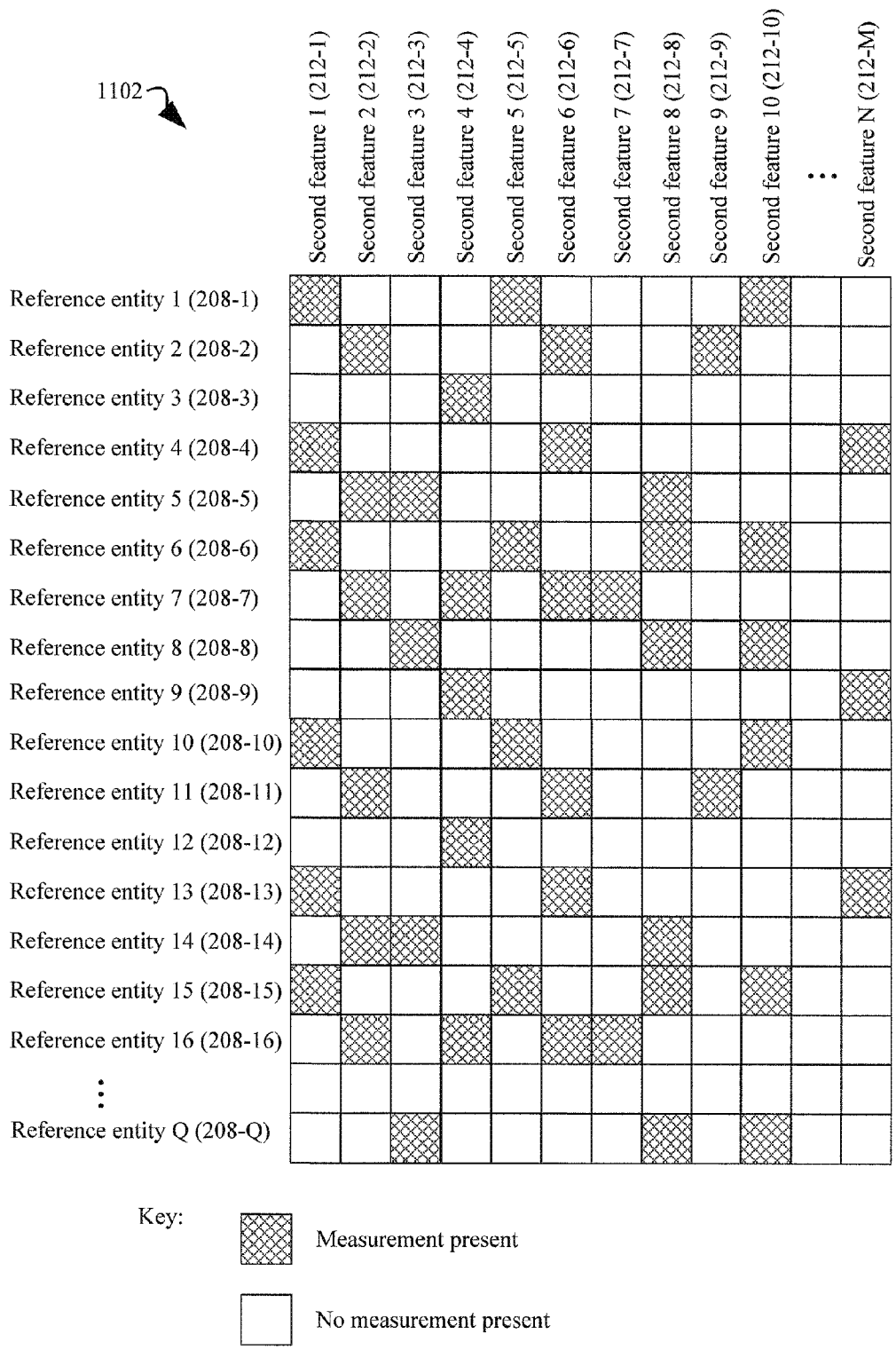
FIG. 11 illustrates how reference entities of a training set include certain measurements of second features in an M-dimensional feature space in accordance with an embodiment of the present disclosure.

For each respective reference entity 208, the training set 206 further comprises a respective measurement of each second feature 212 in a respective subset of an M-dimensional feature space. Here M is a positive integer. There is no requirement that each respective entity 208 include a measurement for each of the second features 212 in the M-dimensional feature space, as FIG. 11 illustrates. Reference entity 208-1 includes measurements for second features 212-1, 212-5, and 212-10 whereas reference entity 208-2 includes measurements for second features 212-2, 212-6, and 212-9. Thus, reference entity 208-1 includes a respective measurement of each second feature 212 in a first subset of second features in the M-dimensional feature space (second features 212-1, 212-5, and 212-10) and reference entity 208-2 includes a respective measurement of each second feature 212 in a second subset of second features in the M-dimensional feature space (second features 212-2, 212-6, and 212-9), where the first and second subsets are not necessarily the same and in fact are different in this example.

In some embodiments, M is an integer of 1, 2, 3, 4, 5, 6, 7, 8, 9, or 10 or more. In some embodiments M is an integer of 15 or more, 20 or more, 30 or more, 50 or more, 75 or more, 100 or more, 200 or more, or 300 or more, 500 or more, 1000 or more, or 2000 or more.

The training set 206 collectively provides at least one measurement for each first feature 210 in the N-dimensional feature space. For instance, as illustrated in FIG. 10, the training set 206 includes at least one measurement for each first feature 210 in the N-dimensional feature space. To illustrate, for the first feature 210-1, the training set 206 includes a reference entity 208-1 and a reference entity 208-4 that each includes a measurement for the first feature 210-1. Further, for second feature 210-2, the training set 206 includes a reference entity 208-3 and a reference entity 208-Q that each includes a measurement for the first feature 210-2. In some embodiments, the training set 206 collectively provides two or more measurements for each first feature 210 in the N-dimensional feature space, where each such measurement is from a different reference entity 208 in the training set 206. In some embodiments, the training set 206 collectively provides three or more measurements for each first feature 210 in the N-dimensional feature space, where each such measurement is from a different reference entity 208 in the training set 206. In some embodiments, the training set 206 collectively provides four or more measurements for each first feature 210 in the N-dimensional feature space, where each such measurement is from a different reference entity 208 in the training set 206.

Measurements of some of these first features 210 are inherently numeric quantities (e.g. molecular weight) while others are categorical variables (e.g. structural class). However, some categorical values can be inferred as continuous variables under certain experimental conditions. For example, a protein's ability to polymerize may be a function of solvent composition. In this way, categorical variables can be transformed to a mixture of states, where a protein has a finite probability of being in each state. Moreover, additional first features may be created from linear (and possibly non-linear) combinations of existing, directly measured, first features.

The training set 206 collectively provides at least one measurement for each second feature 212 in the M-dimensional feature space. For instance, as illustrated in FIG. 11, the training set 206 includes at least one measurement for each second feature 212 in the N-dimensional feature space. To illustrate, for the second feature 212-1, the training set 206 includes a reference entity 208-1, a reference entity 208-4, a reference entity 208-6, a reference entity 208-10, a reference entity 208-13, and a reference entity 208-15 that each includes a measurement for the second feature 212-1. Further, for second feature 212-2, the training set 206 includes a reference entity 208-2, a reference entity 208-5, a reference entity 208-8, a reference entity 208-11, a reference entity 208-14, and a reference entity 208-16 that each includes a measurement for the second feature 212-2. In some embodiments, the training set 206 collectively provides two or more measurements for each second feature 212 in the M-dimensional feature space, where each such measurement is from a different reference entity 208 in the training set 206. In some embodiments, the training set 206 collectively provides three or more measurements for each second feature 212 in the M-dimensional feature space, where each such measurement is from a different reference entity 208 in the training set 206. In some embodiments, the training set 206 collectively provides four or more measurements for each second feature 212 in the M-dimensional feature space, where each such measurement is from a different reference entity 208 in the training set 206.

Non-limiting examples of first features (input features) 210 of an entity are protein content, molecular weight (e.g., average molecular weight or molecular weight distribution), pH, solubility, protein bond interactions (e.g., involving interactions beyond covalent interactions—ionic, hydrophobic bonds etc.), concentration, isoelectric point, hardness, viscosity, moisture content, volume, specific gravity, density, phase transition, temperature (pressure and humidity dependence thereof), extensibility, phospholipid concentration, a textural feature, and aggregation of the corresponding entity. In some embodiments, such first features 210 are basic biochemical and/or physicochemical properties of reference entities, which can be obtained either through biochemical and/or physicochemical assays or possibly from publically available data. For instance, in some embodiments reference entities 208 are plant compounds (e.g., sample protein) and the first features 210 are measurements from biochemical and/or physicochemical assays.

At least one second feature 212 (output feature) in the M-dimensional feature space is a metric for the target property. Non-limiting examples of second features (output features) 212 are structure, emulsification ability, stability, water binding ability, phase separation, oil holding capacity, foaming ability, coalescence, gelling, gelation, caramelization, aeration, chewiness, gumminess, springiness, sensory (taste, texture, flavor, aroma, mouthfeel, aftertaste, finish, appearance), syneresis, cohesiveness, brittleness, elasticity, adhesiveness, shelf-life, color, and odor. The N-dimensional feature space does not include any of the second features in the M-dimensional space. The M-dimensional feature space does not include any of the first features in the N-dimensional space.

In some embodiments, the test entity comprises a protein, a fragment thereof, or a mixture of the protein with one or more other proteins. However, the present disclosure is not so limited. In some embodiments, the test entity comprises organic molecules derived from living organisms such as protein (e.g., unmodified protein, sulfated, acylated or glycosylated protein, non-ribosomal peptide), amino acids, oil (e.g., triglyceride, sterols and other neutral lipids), polar lipid (e.g., phospholipids, glycolipids, sphingolipids), carbohydrate (e.g., polysaccharide, oligosaccharide, disaccharide, monosaccharide), sugar alcohols, phenols, polyphenols, nucleic acids, polynucleic acids, polyketide, a xenobiotic compound, combinations and covalently-bound combinations thereof (e.g., glycosidic protein or protein-bound lipid), and/or mixtures thereof (e.g., an oil and a phospholipid, etc.). In some embodiments, the test entity 218 is naturally occurring and is extracted from an organism such as a plant. In some embodiments, the test entity is synthetically made. In typical embodiments, the test entity 218 is obtained from a plant. Various components of plants have been used for food applications including use as flavoring agents, for example, diterpenes (e.g., steviol), and coloring agents such as carotenoids. More recently, Canadian yellow pea proteins have been found to be useful as a replacement ingredient for eggs. See Tetrick et al., WO2013067453, which is hereby incorporated by reference. This and other plant compounds may be more commercially suitable ingredients based on their functional characteristics such as emulsification and taste in addition to the benefits of sustainability and lower costs.

Referring to block 406 of FIG. 4A, in some embodiments, the respective measurement of each first feature 210 in the N-dimensional feature space for a single reference entity 208 in the plurality of reference entities is obtained from a molecular assay set comprising three or more different molecular assays. To this end, numerous molecular assays exist for measuring first features of reference entities (e.g., plant compounds or components), which include, without limitation, SDS-PAGE, HPLC, LC-MS, GC-MS, probe spectrofluorometry using ANS, CPA, DPH, Prodan, SDS binding, hydrophobic interaction chromatography, contact angle, and hydrophobic partition. See, Nakai, 2004, "Measurement of Protein Hydrophobicity," Current Protocols in Food Analytical Chemistry B:B5:B5.2, which is hereby incorporated by reference. Thus, in embodiments where the respective measurement of each first feature 210 in the N-dimensional feature space for a single reference entity 208 in the plurality of reference entities is obtained from a molecular assay set comprising three or more different molecular assays, three or more such molecular assays are invoked for a given reference entity 208 in order to obtain the measurements of the first features 210 for the given reference entity.

Referring to block 408 of FIG. 4A, in some embodiments, a plurality of first features 210 in the N-dimensional feature space for a single reference entity 208 in the plurality of reference entities is obtained from a single molecular assay of the reference entity. For instance, in some embodiments, the single molecular assay is run under several different environmental or process conditions in order to obtain the plurality of measurements of the first features 210 for the given reference entity. To illustrate, referring to block 410 of FIG. 4A, in some embodiments, each first feature 210 in the plurality of first features is measured using a single molecular assay under a different physical condition (e.g. pH, temperature, or concentration) of the single reference entity. In one such example, for a given reference entity, a particular molecular assay is run at each of four different pH values in order to obtain measurements for the reference entity at four different pH values and the measurements at each pH value represent a different first feature 210 in the N-dimensional feature space. As another example, for a given reference entity, a particular molecular assay is run at each of seven different temperatures in order to obtain measurements for the reference entity at seven different temperatures and the measurements at each temperature represent a different first feature 210 in the N-dimensional feature space. In some embodiments, this plurality of first features is augmented with other first feature measurements for the given reference entity in order to form the full set of first feature measurements for the reference entity.

In some embodiments, each second feature 212 represents a metric for an organoleptic property of food. Organoleptic properties of food are described as taste, odor, color and texture. Mouthfeel is a concept used in the testing and description of food products. Examples of properties which may serve as second features 212 that are metrics for mouthfeel include, but are not limited to, cohesiveness (e.g., degree to which an entity deforms before rupturing when biting with molars), density (e.g., compactness of cross section of the entity after biting completely through with the molars), dryness (e.g., degree to which the sample feels dry in the mouth, fracturability (e.g., force with which the entity crumbles, cracks or shatters, and encompasses crumbliness, crispiness, crunchiness and brittleness), graininess (e.g., degree to which a sample contains small grainy particles, may be seen as the opposite of smoothness), gumminess, (e.g., energy required to disintegrate a semi-solid entity to a state ready for swallowing), hardness (e.g., force required to deform the entity to a given distance, for instance, the force to compress between molars, bite through with incisors, compress between tongue and palate), heaviness, (e.g., weight of entity perceived when first placed on tongue), moisture absorption (e.g., amount of saliva absorbed by entity), moisture release (e.g., amount of wetness/juiciness released from sample) mouthcoating (e.g., type and degree of coating in the mouth after mastication, for instance fat/oil), roughness (e.g., degree of abrasiveness of entities' surface perceived by the tongue), slipperiness (e.g., degree to which the entity slides over the tongue), smoothness (e.g., absence of any particles, lumps, bumps, etc., in the entity), uniformity (e.g., degree to which the entity is even throughout, homogeneity), uniformity of bite, (e.g., evenness of force through bite of entity), uniformity of chew (e.g., degree to which the chewing characteristics of the entity are even throughout mastication) viscosity (e.g., force required to draw the entity from a spoon over the tongue), and wetness (e.g., an amount of moisture perceived on entities' surface). In some embodiments, such second features can be measured and such measurements can be used to assess the suitability of replacement ingredients in model food systems such as in finished products and formulations in accordance with the systems and methods of the present disclosure.

Referring to block 412 of FIG. 4A, in some embodiments, each respective measurement of each second feature 212 in a respective subset of the M-dimensional feature space for a single reference entity 208 is obtained from a functional assay set comprising three or more different functional assays for the single reference entity.

Figure 4B:
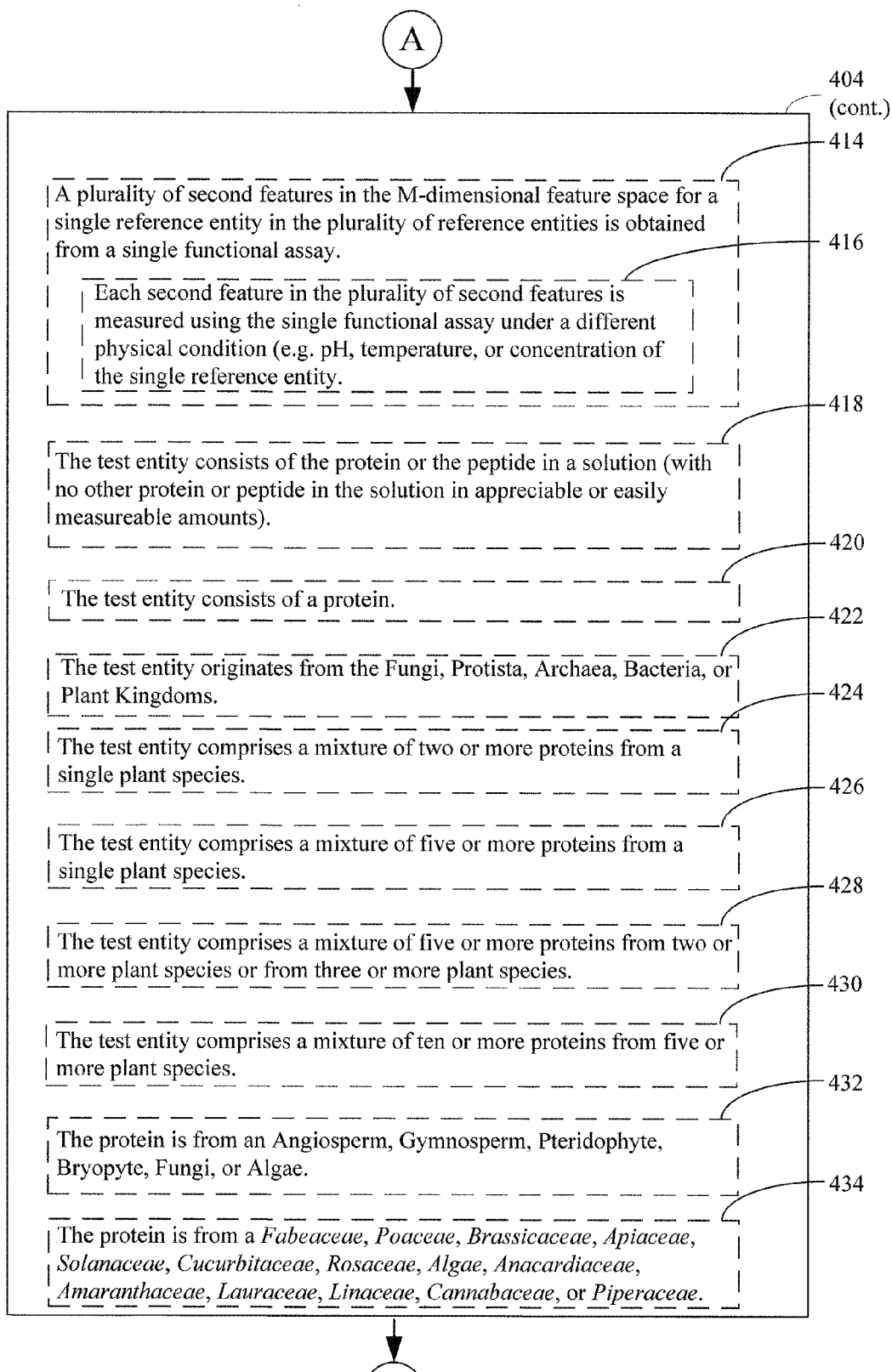

Referring to block 414 of FIG. 4B, in some embodiments, a plurality of second features 212 in the M-dimensional feature space for a single reference entity 208 in the plurality of reference entities is obtained from a single functional assay of the reference entity. For instance, in some embodiments, the single functional assay is run under several different environmental or process conditions in order to obtain the plurality of measurements of the second features 210 for the given reference entity. For instance, in some embodiments, a single functional assay is run under several different environmental or process conditions in order to obtain the plurality of measurements of the second features 212 for the given single reference entity. To illustrate, referring to block 416 of FIG. 4B, in some embodiments, each second feature 212 in a plurality of second features is measured using a single functional assay under a different physical condition (e.g. pH, temperature, or concentration) of the single reference entity. In one such example, for a given reference entity, a particular functional assay is run at each of three different pH values in order to obtain measurements for the reference entity at three different pH values and the measurements at each pH value represent a different second feature 212 in the M-dimensional feature space. As another example, for a given reference entity, a particular functional assay is run at each of seven different concentrations (of the reference entity in solution) in order to obtain measurements for the reference entity at seven different concentrations and the measurements at each concentration represent a different second feature 212 in the M-dimensional feature space. In some embodiments, this plurality of second features is augmented with other second feature measurements for the given reference entity in order to form the full set of second feature measurements for the reference entity.

Referring to FIG. 4B, in some embodiments a test entity 218 consists of a protein or a peptide in a solution (block 418). In some such embodiments there is no other protein or peptide in the solution in appreciable or easily measureable amounts. That is, a single protein or peptide in solution is provided as a test entity.

In some such embodiments, the test entity 218 consists of a protein (420). That is, the test entity is a single protein as opposed to a peptide or some other compound. In such embodiments, the sum total of all proteins in the test entity 218 other than the single protein is less than 5 percent (w/v) of the test entity 218, less than 4 percent (w/v) of the test entity 218, less than 3 percent (w/v) of the test entity 218, less than 2 percent (w/v) of the test entity 218, less than 1 percent (w/v) of the test entity 218, less than 0.5 percent (w/v) of the test entity 218, less than 0.25 percent (w/v) of the test entity 218, or less than 0.05 percent (w/v) of the test entity 218.

Representative test entities 218 are plant protein fractions, concentrates or isolates, such as pea proteins, isolates, and/or concentrates; garbanzo (chickpea) proteins, isolates, and/or concentrates; fava bean proteins, isolates, and/or concentrates; soy proteins, isolates, and/or concentrates; rice proteins, isolates, and/or concentrate; potato proteins, isolates, and/or concentrates; hemp proteins, isolates, and/or concentrates; or any combinations thereof. Additional representative test entities 218 are plant proteins such as soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, green pea powder, green bean powder, and any proteins derived from beans, lentils, and pulses. In other embodiments, the pea proteins can be derived from green peas or yellow peas. In particular embodiments, the pea proteins can be derived from yellow peas, such as Canadian yellow peas.

In some embodiments, the test entity 218 originates from a member of the Plant Kingdom. For instance, in some embodiments a plant is crushed or otherwise processed and the test entity is extracted from the plant (block 422). In some embodiments, test entity 218 originates from a member of the Fungi, Protista, Archaea, or Bacteria Kingdoms. For instance, in some embodiments one or more different members of the Fungi Kingdom are harvested or otherwise processed and the test entity is extracted from the harvest or other form of processed product. In some embodiments a species or combination of species of the Protista Kingdom are harvested or otherwise processed and the test entity is extracted from the harvest or other form of processed product. In some embodiments a species or combination of species from the Archaea Kingdom are harvested or otherwise processed and the test entity is extracted from the harvest or other form of processed product. In some embodiments a species or combination of species from the Bacteria Kingdom are harvested or otherwise processed and the test entity is extracted from the harvest or other form of processed product.

In some such embodiments, the test entity 218 comprises a mixture of two or more proteins, three or more proteins, four or more proteins, five or more proteins, ten or more proteins, or 20 or more proteins from a single plant species (blocks 424-426). In some such embodiments, multiple plant specimens of the single plant species are used to source the test entity 218. In some such embodiments, a single plant specimen of the single plant species is used to source the test entity 218. In some such embodiments, multiple plant specimens or a single plant specimen of the single plant species harvested from a specific geographical location (e.g., a particular appellation, a particular region, a particular county, a particular state, a particular country) is used to source the test entity 218. In some such embodiments, multiple plant specimens or a single plant specimen of the single plant species harvested at a predetermined time or year (e.g., Spring, Summer, Fall, Winter) is used to source the test entity 218. In some such embodiments, multiple plant specimens or a single plant specimen of the single plant species that has been stored for a predetermined amount of time after harvesting (e.g., less than one hour, less than one day, less than one week, less than one month) is used to source the test entity 218.

In some embodiments, the test entity 218 comprises a mixture of five or more proteins from two or more plant species or from three or more plant species (block 428).

In some embodiments, the test entity 218 comprises a mixture of between five and ten proteins from between two and five plant species. In some embodiments, the test entity 218 comprises a mixture of between five and ten proteins from a single plant species. In some embodiments, the test entity 218 comprises a mixture of between five and ten proteins from a combination of two plant species. In some embodiments, the test entity 218 comprises a mixture of between five and ten proteins from a combination of three plant species. In some embodiments, the test entity 218 comprises a mixture of between five and ten proteins from a combination of four plant species. In some embodiments, the test entity 218 comprises a mixture of between five and ten proteins from a combination of five plant species.

In some embodiments, the test entity 218 comprises a mixture of between ten and twenty proteins from between two and ten plant species. In some embodiments, the test entity 218 comprises a mixture of between ten and twenty proteins from a single plant species. In some embodiments, the test entity 218 comprises a mixture of between ten and twenty proteins from a combination of two plant species. In some embodiments, the test entity 218 comprises a mixture of between ten and twenty proteins from a combination of three plant species. In some embodiments, the test entity 218 comprises a mixture of between ten and twenty proteins from a combination of four plant species. In some embodiments, the test entity 218 comprises a mixture of between ten and twenty proteins from a combination of five plant species. In some embodiments, the test entity 218 comprises a mixture of between ten and twenty proteins from a mixture of six plant species. In some embodiments, the test entity 218 comprises a mixture of between ten and twenty proteins from a combination of seven plant species. In some embodiments, the test entity 218 comprises a mixture of between ten and twenty proteins from a combination of eight plant species. In some embodiments, the test entity 218 comprises a mixture of between ten and twenty proteins from a combination of nine plant species. In some embodiments, the test entity 218 comprises a mixture of between ten and twenty proteins from a combination of ten plant species. In some embodiments, the test entity 218 comprises a mixture of ten or more proteins from five or more plant species (block 430).

In some embodiments, the test entity 218 comprises a protein. In some embodiments, the protein is from an Angiosperm, Gymnosperm, Pteridophyte, Bryopyte, or Algae (block 432). In some embodiments, the protein is from a Fungi. In some embodiments, the test entity 218 consists of a first protein. In some embodiments, the first protein is from an Angiosperm, Gymnosperm, Pteridophyte, Bryopyte, or Algae (block 432). In some embodiments, the first protein is from a Fungi. In such embodiments, the sum total of all proteins in the test entity other than the first protein is less than 5 percent (w/v) of the test entity 218, less than 4 percent (w/v) of the test entity 218, less than 3 percent (w/v) of the test entity 218, less than 2 percent (w/v) of the test entity 218, less than 1 percent (w/v) of the test entity 218, less than 0.5 percent (w/v) of the test entity 218, less than 0.25 percent (w/v) of the test entity 218, or less than 0.05 percent (w/v) of the test entity 218.

In some embodiments, the protein is from a Fabeaceae, Poaceae, Brassicaceae, Apiaceae, Solanaceae, Cucurbitaceae, Rosaceae, Algae, Anacardiaceae, Amaranthaceae, Lauraceae, Linaceae, Cannabaceae, or a Piperaceae (Block 434).

Figure 4C:
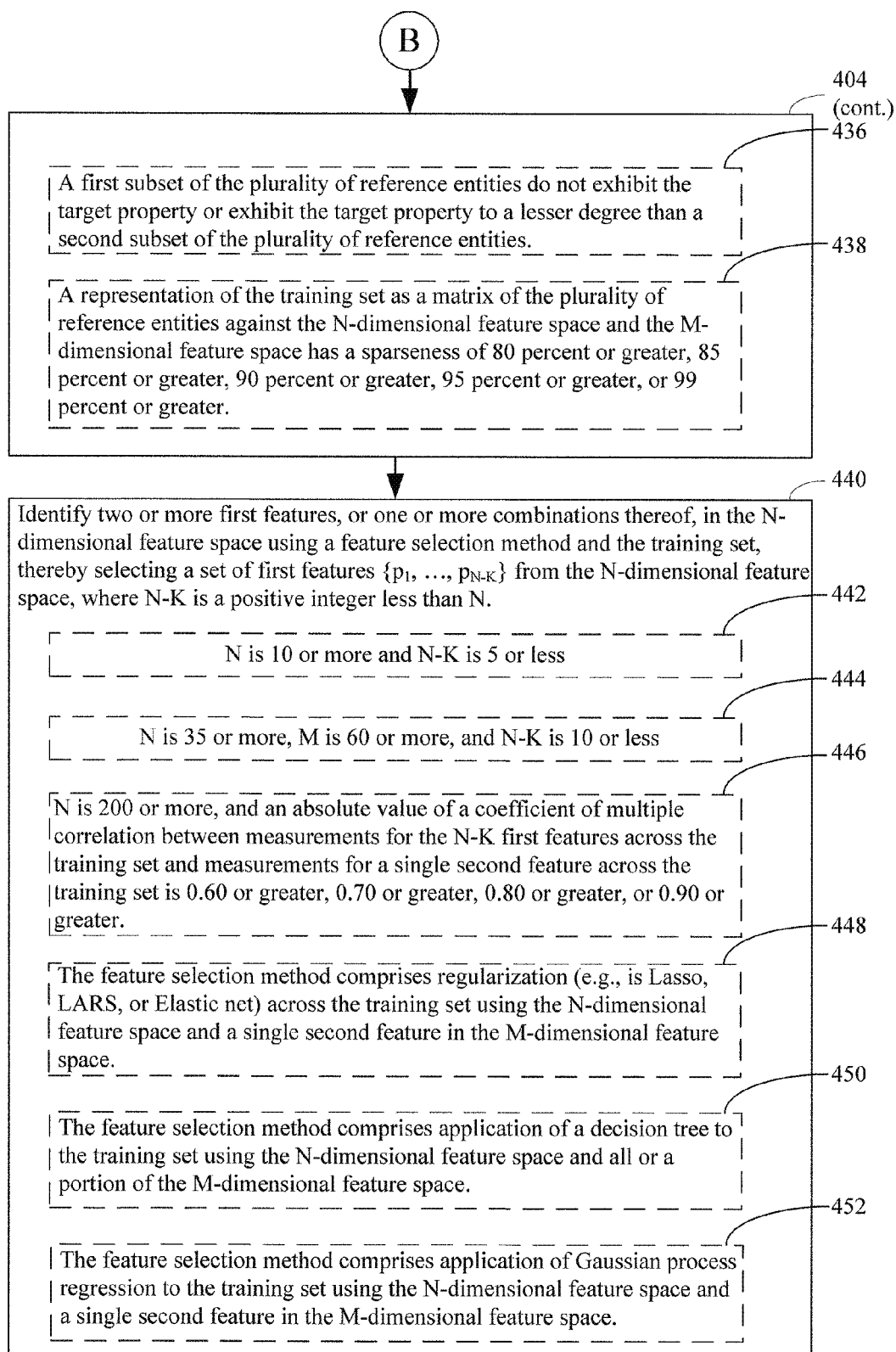

Referring to block 436 of FIG. 4C, in some embodiments, a first subset of the plurality of reference entities do not exhibit the target property or exhibit the target property to a lesser degree than a second subset of the plurality of reference entities. This variance in the extent to which each reference property exhibits the target property can be used to train a model 214 as described in further detail below. However, in some embodiments, all the reference entities exhibit the target property. Certain models (e.g., clustering) 214 can be invoked in accordance with the systems and methods of the present disclosure even in those instances where there are no reference entities that do not exhibit the target property.

Referring to block 438 of FIG. 4C, in some embodiments, a representation of the training set 206 as a matrix of the plurality of reference entities against the N-dimensional feature space and the M-dimensional feature space has a sparseness of 80 percent or greater, 85 percent or greater, 90 percent or greater, 95 percent or greater, or 99 percent or greater. Such a matrix is a two-dimensional matrix defined by the dimensions (i) reference entity identity by (ii) first features (210) or second features (212). Such a two-dimensional matrix can be conceptualized by combining the two-dimensional matrix 1002 of FIG. 10 (reference entities× first features) and the two-dimensional matrix 1102 FIG. 11 (reference entities×second features). For instance, matrices 1002 and 1102 can simply be combined based on their common dimension of reference entities. The term "sparseness" as used herein can be addressed by considering the sparseness of the matrix 1002 illustrated in FIG. 10. There, sparseness is the percentage of cells that do not contain a measurement (60 cells, assuming N is 12) as compared to the total number of cells (6×12=72, assuming N is 12) in the matrix 1002, or $60/72$ which equals 83.3 percent. In general, sparseness of the two dimensional matrix of a respective reference entity in the plurality of reference entities against the N-dimensional feature space and the M-dimensional feature space is the percentage of missing measurements in the N-dimensional feature space and the M-dimensional feature space for the respective reference entity divided by the total possible number of measurements in the N-dimensional feature space and the M-dimensional feature space for the reference entity.

Very sparse datasets can be used in the systems and methods of the present disclosure. Moreover, the systems and methods of the present disclosure enable for the sampling of a large number of first features 210. This is advantageous because it is typically not known a priori which of the first features 210 will provide useful surrogates for the second features 212. In general, it is desirable to identify first features 210 that serve as surrogates to the second features 212 because the measurements of the first features are cheaper or faster to make than measurements of the second features. In typical embodiments, prior to subjecting an entire training set 206 that contains a sparse sampling of measurements for a vast array of first features and measurements for second features to a model 214, the training set 206 is subjected to a feature selection method to identify a set of first features $\{p_1, \ldots, p_{N-K}\}$ from the N-dimensional feature space, where N–K is a positive integer less than N. In other words, a feature selection method is used to select a subset of first features to use from among the total possible universe of first features in the training set 206. To numerically illustrate, in one example the N-dimensional feature space consists of 1000 different first features and the feature selection method is used to identify 100 or fewer of these first features to use in model training or model application using the systems and methods of the present disclosure. In this numeric example, N is 1000, K is 900, and $\{p_1, \ldots, p_{N-K}\}$ is $\{p_1, P_2, P_3, \ldots, p_{100}\}$ where each $p_i$ in $\{p_1, \ldots, p_{N-K}\}$ represents a different first feature 210 from the N-dimensional space selected by the feature selection method. In this way, in some embodiments, two or more first features 210 in the N-dimensional feature space are identified using a feature selection method and the training set 206, thereby selecting a set of first features {p₁, ..., p_{N-K}} from the N-dimensional feature space, where N–K is a positive integer less than N (block 440).

In some embodiments N is 10 or more and N–K is 5 or less (block 442). That is, the number of different first features 210 in the N-dimensional space sampled by the training set 206 is ten or more and, after the feature selection method, five or fewer first features 210 are selected. In some embodiments, N is 35 or more, M is 60 or more, and N–K is 10 or less (block 444). That is, the number of different first features 210 in the N-dimensional space sampled by the training set 206 is 35 or more, the number of second features 212 in the M-dimensional space sampled by the training set 206 is 60 or more and, after the feature selection method, ten or fewer first features 210 are selected. In some embodiments, a first feature selection method is used to select a first subset of first features from the N-dimensional space and a second feature selection method is used to select a second subset of second features from the M-dimensional space. In some embodiments, the feature selection method is used to select first features and second features of the training set. In some embodiments, N is 5 or greater, 10 or greater, 20 or greater, 30 or greater, 40 or greater, 50 or greater or 100 or greater. In some embodiments, N–K is 100 or less, 50 or less, 25 or less or 10 or less. In some embodiments, N–K is between 4 and 50, between 2 and 75, or between 4 and 200.

In some embodiments N is 200 or more, and the absolute value of the coefficient of multiple correlation between the measurements for the selected N–K first features across the training set and the variation of a single second feature 212 across the training set is 0.5 or greater (e.g., less than –0.50 or greater than 0.50), 0.6 or greater, 0.7 or greater or 0.8 or greater (block 446). In some embodiments, for the computation of the coefficient of multiple correlation between the measurements for the selected N–K first features across the training set 206 and the variation of a single second feature 212 across the training set 206, only those reference entities 208 that have measurements for each of the N–K first features and the single second feature contribute to the computation of the coefficient of multiple correlation. The coefficient of multiple correlation is a measure of how well a given variable (e.g., measurements of the second feature 212 across the training set) can be predicted using a linear function of a set of other variables (e.g., measurements of the N–K first features across the training set). It is the correlation between the dependent variable's values and the best predictions that can be computed linearly from the predictive variables. The coefficient of multiple correlation takes values between 0 and 1, with a higher value indicating a better predictability of the dependent variable (the second feature 212) from the independent variables (the N–K first features), with a value of 1 indicating that the predictions are exactly correct and a value of 0 indicating that no linear combination of the independent variables is a better predictor than is the fixed mean of the dependent variable. See, Allison, 1998, *Multiple Regression: A Primer*. London: Sage Publications, which is hereby incorporated by reference. In some embodiments, rather than a coefficient of multiple correlation, a Pearson coefficient is used which yield correlation coefficients between –1 and 1, with a higher absolute value for the correlation coefficient indicating a better predictability of the dependent variable from the independent variables. In some embodiments, a nonparametric correlation is used such as a Spearman R, Kendall tau, or a Gamma statistic.

In some embodiments, each of the first features 210 are independent features whereas the second features 212, or at least the one or more second features used in model training are dependent on the value of one or more first features. In some embodiments the measurement values of the N–K first features selected by the feature selection method are not dependent upon the values of the one or more second features 212 used in model training.

The present disclosure encompasses a broad array of feature selection methods known to those of skill in the art. In some embodiments, the feature selection method is a least angle regression or a stepwise regression. Feature selection methods are particularly advantageous in identifying, from among the multitude of variables (e.g., measurements of the first features across the training set and measurements for second features across the training set) present across the training set, which first features have a significant causal effect on a given second feature (e.g., which of the first features are causal for a poor outcome of a second feature or conversely which of the first features are causal for excellent outcome of a second feature). Feature selection techniques are described, for example, in Saeys et al., 2007, "A Review of Feature Selection Techniques in Bioinformatics," Bioinformatics 23, 2507-2517, and Tibshirani, 1996, "Regression and Shrinkage and Selection via the Lasso," J. R. Statist. Soc. B, pp. 267-288, each of which is hereby incorporated by reference.

Representative but non-limiting examples of some such feature selection methods are described with reference to blocks 448 through 452 of FIG. 4C.

In some embodiments, the feature selection method comprises regularization (e.g., is Lasso, least-angle-regression, or Elastic net) across the training set using the N-dimensional feature space and a single second feature in the M-dimensional feature space (block 448) to improve prediction accuracy. Lasso is described in Hastie et al., 2001, *The Elements of Statistical Learning*, pp. 64-65, which is hereby incorporated by reference. Least angle regression is described in Efron et al., 2004, "Least Angle Regression," The Annals of Statistics, pp. 407-499, which is hereby incorporated by reference. Elastic net, which encompasses ridge regression, is described in Hastie, 2005, "Regularization and Variable Selection via the Elastic Net," Journal of the Royal Statistical Society, Series B: pp. 301-320, which is hereby incorporated by reference.

In some embodiments, the feature selection method comprises application of a decision tree to the training set using the N-dimensional feature space and all or a portion of the M-dimensional feature space (block 450). Decision trees are described generally by Duda, 2001, *Pattern Classification*, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, *Pattern Classification*, John Wiley & Sons, Inc., New York. pp. 396-408 and pp. 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety.

The aim of a decision tree is to induce a classifier (a tree) from real-world example data. This tree can be used to classify unseen entities that have not been used to derive the decision tree. As such, a decision tree is derived from the training set 206. As discussed above, the training set contains data for a plurality of reference entities (the training population). For each respective reference entity 208 there is a plurality of first features and a class or scalar value for a second feature that represents the class of the reference entity (e.g., has the desired target property, does not have the desired target property).

Another feature selection method that can be used in the system and methods of the present disclosure is multivariate adaptive regression splines (MARS). MARS is an adaptive procedure for regression, and is well suited for the high-dimensional problems addressed by the present disclosure. MARS can be viewed as a generalization of stepwise linear regression or a modification of the CART method to improve the performance of CART in the regression setting. MARS is described in Hastie et al., 2001, *The Elements of Statistical Learning*, Springer-Verlag, New York, pp. 283-295, which is hereby incorporated by reference in its entirety.

In some embodiments, the feature selection method comprises application of Gaussian process regression to the training set using the N-dimensional feature space and a single second feature in the M-dimensional feature space (block 452). Gaussian Process Regression is disclosed in Ebden, August 2008, arXiv:1505.029652v2 (29 Aug. 2015), "Gaussian Processes for Dimensionality Reduction: A Quick Introduction," which is hereby incorporated by reference.

Now that exemplary feature selection methods have been described, specific exemplary embodiments of a set of first features $\{p_1, \ldots, p_{N-K}\}$ will be described with reference to blocks 454 and 456 of FIG. 4D. In the specific exemplary embodiment described in block 454, the respective measurement of each first feature 210 in a respective subset of first features in the N-dimensional feature space for each corresponding reference entity 208 in the training set 206 is taken when the corresponding reference entity is in the form of an emulsion or a liquid, and the set of first features $\{p_1, \ldots, p_{N-K}\}$ comprises protein concentration, color, phospholipid concentration, moisture content, or phase transition of the corresponding reference entity. For instance, in some such embodiments, a given reference entity 208 is a particular protein or mixture of proteins that have been solubilized. In such instances, the protein concentration is the protein concentration of the given reference entity 208, the moisture content is a measure of moisture content of the reference entity 208, and so forth.

Figure 4D:
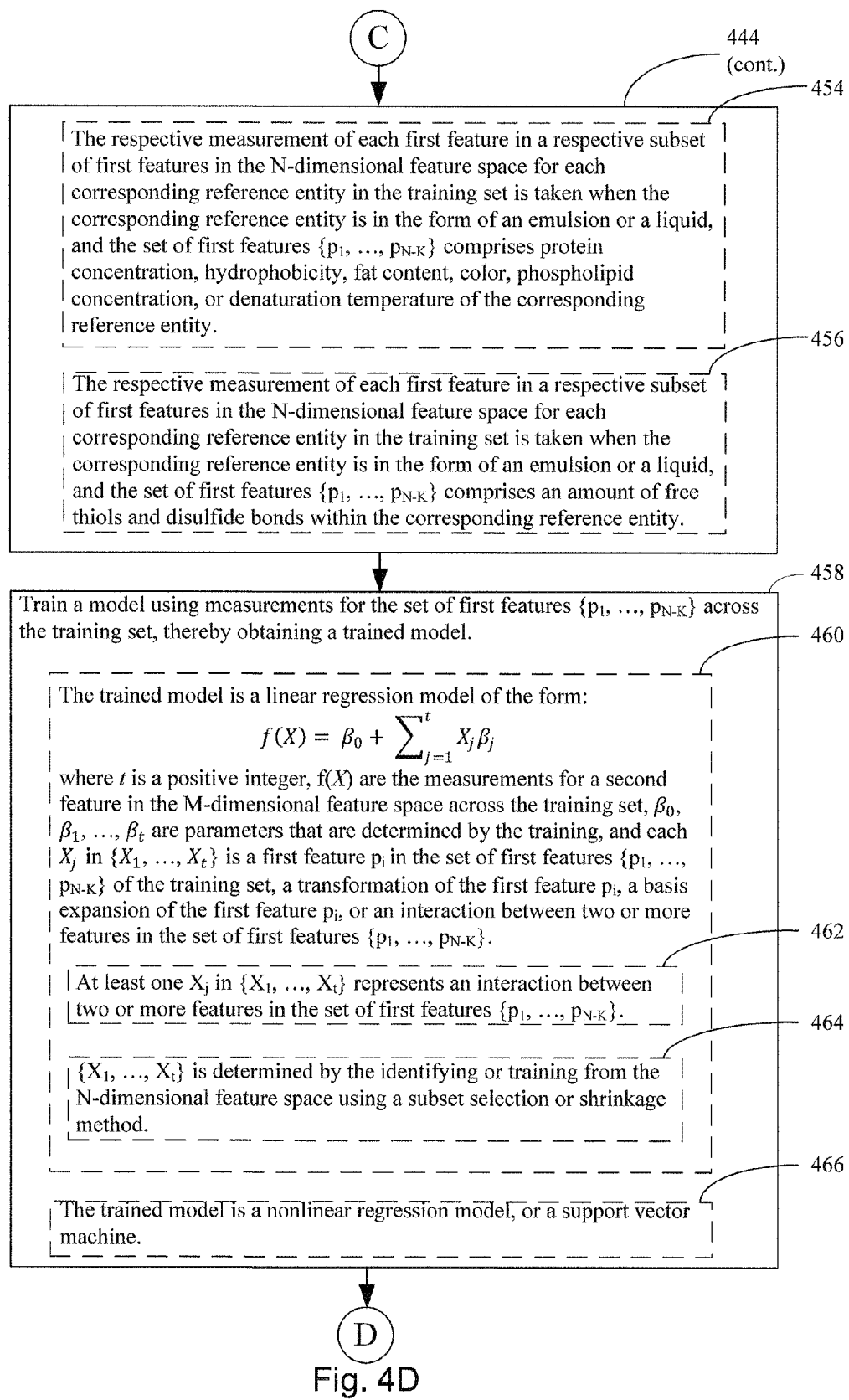

In the specific embodiment of block 456 of FIG. 4D, the respective measurement of each first feature 210 in a respective subset of first features in the N-dimensional feature space for each corresponding reference entity in the training set is taken when the corresponding reference entity is in the form of an emulsion or a liquid, and the set of first features $\{p_1, \ldots, p_{N-K}\}$ comprises an amount of inter- and intra-molecular bonding within the corresponding reference entity. A number of assays for determining an amount of inter- and intra-molecular bonding in a protein are known.

Referring to block 458 of FIG. 4D, once the set of first features $\{p_1, \ldots, p_{N-K}\}$ are identified, measurements of the set of first features $\{p_1, \ldots, p_{N-K}\}$ across the training set are used to train a model 214.

In some embodiments a model 214 is trained using machine learning techniques or methods. Machine learning methods allow a computer system to perform automatic (e.g., through software programs) learning from a set of factual data (e.g., the training set 206), belonging to a specific application field (e.g., domain). Given such a training set 206, machine learning methods are able to extract patterns and relationships from the data themselves. An extensive discussion about machine learning methods and their applications can be found in Mitchell, 1997, *Machine Learning*, McGraw-Hill and U.S. Pat. No. 8,843,482, each of which is hereby incorporated by reference. Well-known machine learning methods include decision trees, association rules, neural networks and Bayesian methods.

Learned patterns and relationships are encoded by machine learning methods in a formal, quantitative model 214, which can take different forms depending on the machine learning technique used. Examples of forms for a model 214 include logic rules, mathematical equations and mathematical graphs. A goal of machine learning methods is that of a better understanding and quantification of patterns within data and relationships between data in order to obtain a model 214 as a representation for the data.

In some embodiments the model 214 is trained against a single second feature 212 across the training set 206. In some embodiments this single second feature is categorical. In some embodiments this single second feature is numerical. In some embodiments, the model is trained against a combination of single second features 212 across the training set. In some embodiments values for second features in the training set are not used to train the model. In some embodiments, kernel transformation techniques and/or principal component analysis techniques are used to identify the set of first features $\{p_1, \ldots, p_{N-K}\}$ as disclosed with respect to some detailed embodiments below. As such, it will be appreciated that, in some embodiments, the set of first features $\{p_1, \ldots, p_{N-K}\}$ is in the form of principal components and it is the principal components that are used to train any of the models 214 described herein. In other embodiments, the measurements of the set of first features $\{p_1, \ldots, p_{N-K}\}$ themselves, not in the form of principal components, are used to train any of the models 214 described herein.

In some embodiments, the model 214 is a supervised regression model and the trained model provides predictions of real values for a single second feature 212. Such approaches are useful instances where the target second feature 212 is measured as a continuous number. An example of such a supervised regression model is provided in Example 1 below.

In some embodiments, the model 214 is a supervised classification model and the trained model provides a prediction of a classification for a single second feature 212. Such approaches are useful instances where the target second feature 212 is measured as a discrete label.

In some embodiments, the model 214 is a supervised classification model and the trained model provides a prediction of a classification of a combination of second features 212 (e.g., multi-class classification). Such approaches are useful instances where the target second feature 212 is measured as a discrete label. An example of such supervised classification is provided in Example 2 below.

In some embodiments, the model 214 is an unsupervised clustering model or a nearest neighbor search model. Example 3 below provides an example of such an unsupervised approach in which models quantify overall first feature 210 distances among reference entities 208.

In some embodiments, an ensemble (two or more) of models 214 is used. In some embodiments, a boosting technique such as AdaBoost is used in conjunction with many other types of learning algorithms to improve their performance. In this approach, the output of any of the models 214 disclosed herein, or their equivalents, is combined into a weighted sum that represents the final output of the boosted classifier. See Freund, 1997, "A decision-theoretic generalization of on-line learning and an application to boosting," Journal of Computer and System Sciences 55, p. 119, which is hereby incorporated by reference.

Figure 4E:
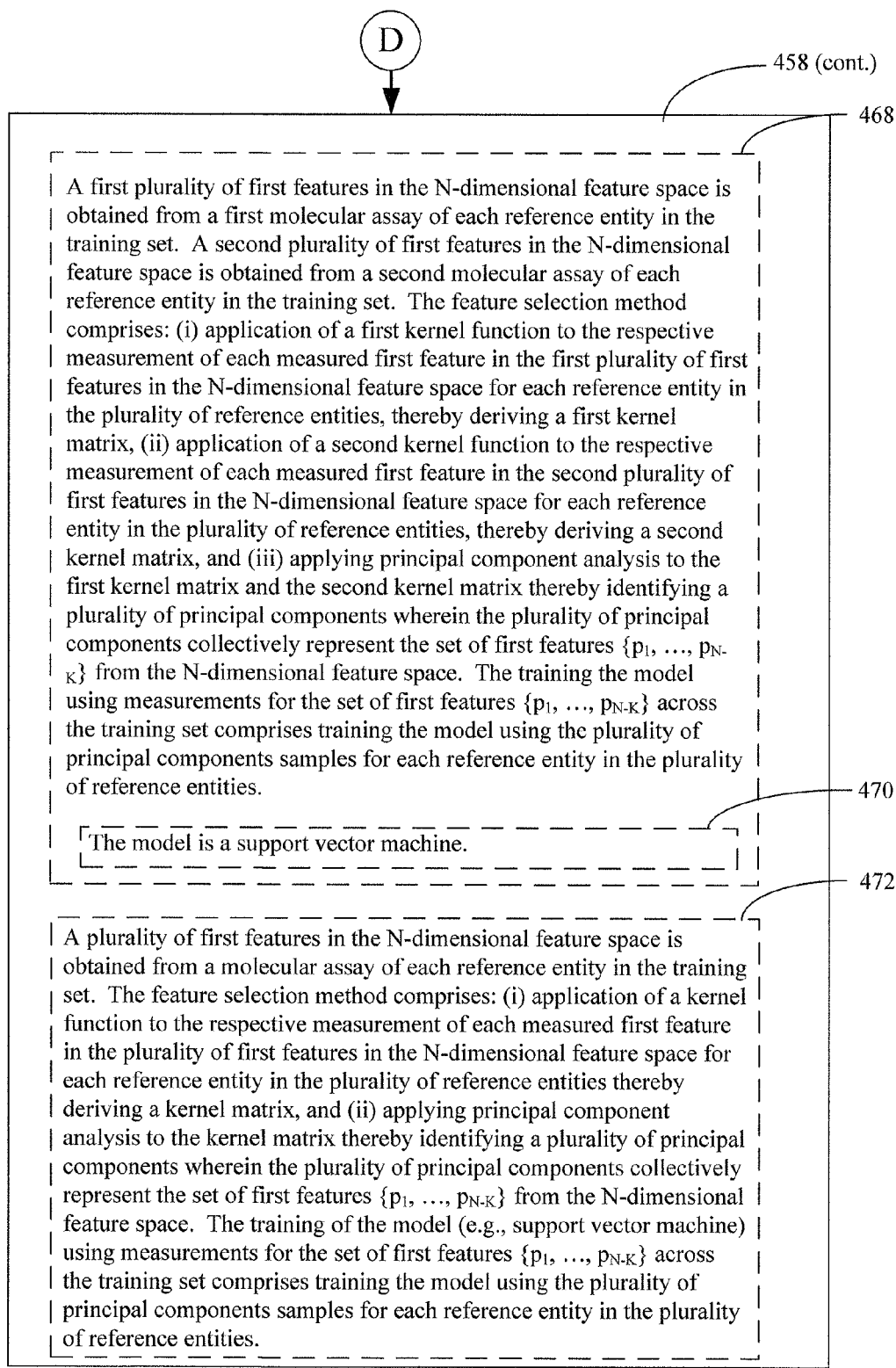
Figure 4F:
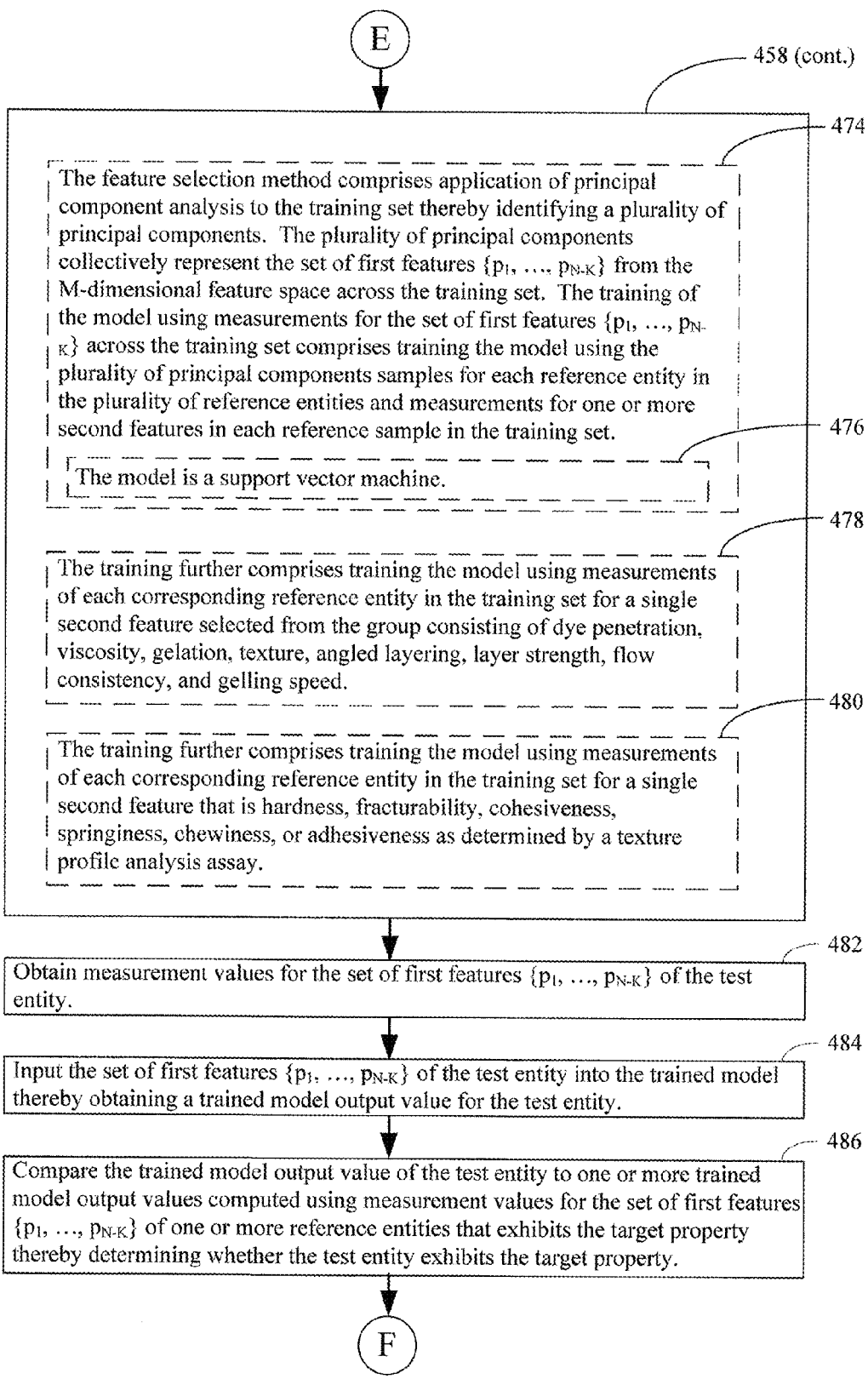

Now that an overview of different classifications of models that are used in various embodiments of the present disclosure have been outlined, more details of specific models and model training are provided with reference to blocks 460 through 480 of FIGS. 4D through 4F.

Referring to block 460, in some embodiments the trained model is a linear regression model of the form:

$$f(X) = \beta_0 + \Sigma_{j=1}^{t} X_j \beta_j$$

where t is a positive integer, f(X) are the measurements for a second feature 212 in the M-dimensional feature space across the training set 206, $\beta_0, \beta_1, \ldots, \beta_t$ are parameters that are determined by the training of the model, and each $X_j$ in $\{X_1, \ldots, X_t\}$ is a first feature $p_i$ in the set of first features $\{p_1, \ldots, p_{N-K}\}$ of the training set, a transformation of the first feature $p_i$, a basis expansion of the first feature $p_i$, an interaction between two or more first features in the set of first features $\{p_1, \ldots, p_{N-K}\}$, or a principal component expressed as a linear combination of two or more first features in the set of first features $\{p_1, \ldots, p_{N-K}\}$. See Hastie et al., 2001, *The Elements of Statistical Learning*, pp. 42-49; and Jolliffe, 1982, "A note on the Use of Principal Components in Regression," Journal of the Royal Statistical Society, Series C. 31 (3), pp. 300-303, each of which is hereby incorporated by reference. Examples of a transformation of a first feature $p_i$ include, but are not limited to, a log, square-root, a square of $p_i$, or, in general, raising $p_i$ to a power. An example of a basis expansion of the first feature $p_i$ include, but are not limited to representing the first feature $p_i$ as a polynomial, a piecewise polynomial or a smoothing spline as discussed in Hastie et al., 2001, *The Elements of Statistical Learning*, Chapter 5, which is hereby incorporated by reference. An example of an interaction between two or more features in the set of first features $\{p_1, \ldots, p_{N-K}\}$ is $p_1 \cdot p_2$. Referring to block 462, in some embodiments, at least one $X_j$ in $\{X_1, \ldots, X_t\}$ represents an interaction between two or more features in the set of first features $\{p_1, \ldots, p_{N-K}\}$.

Referring to block 464, in some embodiments, $\{X_1, \ldots, X_t\}$ is determined by the identifying or training from the N-dimensional feature space using a subset selection or shrinkage method for the linear regression model. In a subset selection process, only a subset of the variables is used for the linear regression model. In some embodiments, a subset selection process is invoked as the feature selection method of step 440 before training the linear regression model. Examples of subset selection methods are disclosed in Hastie et al., 2001, *The Elements of Statistical Learning*, pp. 55-58, which is hereby incorporated by reference.

Rather than discarding first features as is the case in subset selection, shrinkage methods impose a penalty on the size of their coefficients. In some embodiments, the subset selection process is invoked as the feature selection method of step 440 before training the linear regression model. Examples of shrinkage methods are disclosed in Hastie et al., 2001, *The Elements of Statistical Learning*, pp. 59-65, which includes the lasso method, which is hereby incorporated by reference.

Referring to block 466 of FIG. 4D, in some embodiments, the trained model 214 is a nonlinear regression model. In nonlinear regression approaches, each $X_j$ in $\{X_1, \ldots, X_t\}$ is modeled as a random variable with a mean given by a nonlinear function $f(x,\beta)$. See Seber and Wild, 1989, *Nonlinear Regression*, New York: John Wiley and Sons, ISBN 0471617601, which is hereby incorporated by reference.

Continuing to refer to block 466 of FIG. 4D, in some embodiments of the present disclosure, the trained model 214 is a support vector machine (SVM). In such embodiments, SVMs are trained to classify a respective entity using measurements of the set of first features $\{p_1, \ldots, p_{N-K}\}$ across the training set 206 and a measurement of a second feature 212 across the training set. SVMs are described in Cristianini and Shawe-Taylor, 2000, "An Introduction to Support Vector Machines," Cambridge University Press, Cambridge; Boser et al., 1992, "A training algorithm for optimal margin classifiers," in Proceedings of the 5$^{th}$ Annual ACM Workshop on Computational Learning Theory, ACM Press, Pittsburgh, Pa., pp. 142-152; Vapnik, 1998, *Statistical Learning Theory*, Wiley, New York; Mount, 2001, *Bioinformatics: sequence and genome analysis*, Cold Spring Harbor Laboratory Press, Cold Spring Harbor, N.Y.; Duda, *Pattern Classification*, Second Edition, 2001, John Wiley & Sons, Inc., pp. 259, 262-265; and Hastie, 2001, *The Elements of Statistical Learning*, Springer, New York; and Furey et al., 2000, *Bioinformatics* 16, 906-914, each of which is hereby incorporated by reference in its entirety. When used for classification, SVMs separate a given set of binary labeled data training set (e.g., the target second feature is provided with a binary label of either possessing the target second feature or not possessing the target feature) with a hyperplane that is maximally distant from the labeled data. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

In one approach, when a SVM is used, the feature data is standardized to have mean zero and unit variance and the reference entities 208 of the training set 206 are randomly divided into a training set and a test set. For example, in one embodiment, two thirds of the members of the training set 206 are placed in the training set and one third of the members of the training set are placed in the test set. The measurements for the set of first features $\{p_1, \ldots, p_{N-K}\}$ are then used to train the SVM. Then the ability for the trained SVM to correctly classify entities in the test set is determined. In some embodiments, this computation is performed several times for a given combination of the set of first features $\{p_1, \ldots, p_{N-K}\}$. In each iteration of the computation, the members of the training population are randomly assigned to the training set and the test set. Then, the quality of the combination of the set of first features $\{p_1, \ldots, p_{N-K}\}$ is taken as the average of each such iteration of the SVM computation.

Referring to block 468 of FIG. 4E, in some embodiments a first plurality of first features in the N-dimensional feature space is obtained from a first molecular assay of each reference entity 208 in the training set and a second plurality of first features in the N-dimensional feature space is obtained from a second molecular assay of the test entity of each reference entity in the training set. To illustrate, in one example, N is 200 and the first plurality of first features consists of first features 210-X-1 through 210-X-100 and the second plurality of first features consists of first features 210-X-101 through 210-X-200. This reinforces three concepts in accordance with the present disclosure. First, more than one first feature can be measured in a single molecular assay of a reference entity. For instance, the single molecular assay can be run under different conditions thereby producing different first features. Or different types of first features can be calculated using the raw data from the single molecular assay. Second, more than one molecular assay can be used in obtaining the training set 206. Third, since the first features of the training set may originate from different molecular assays there may be no linear separation possible for the measurements of the first features. In such instances, kernel methods can be invoked to realize a non-linear mapping to a feature space that is capable of separating out the measurements of the first features across the training set (e.g., first features 210-X-1 through 210-X-200 in the example above) and thus afford training of a model.

For instance, in some embodiments, the feature selection method comprises: (i) application of a first kernel function to the respective measurement of each measured first feature in the first plurality of first features in the N-dimensional feature space for each reference entity in the plurality of reference entities, thereby deriving a first kernel matrix and (ii) application of a second kernel function to the respective measurement of each measured first feature in the second plurality of first features in the N-dimensional feature space for each reference entity in the plurality of reference entities, thereby deriving a second kernel matrix.

Kernel methods work by embedding the measurements of first features into a vector space, $\mathcal{F}$, called a kernel matrix. A characteristic of kernel methods is that the embedding in feature space is generally defined implicitly, by specifying an inner product for the kernel matrix. Thus, for a pair of data items, $x_1$ and $x_2$ (e.g., first feature 210-1-1 and 210-1-2), denoting their embeddings as $\Phi(x_1)$ and $\Phi(x_2)$, respectively, the inner product of the embedded data is specified, $\langle \Phi(x_1), \Phi(x_2) \rangle$, via a kernel function $K(x_1, x_2)$. In some embodiments, any symmetric, positive semidefinite function is a valid kernel function, corresponding to an inner product in some corresponding kernel matrix. In some embodiments, all that this needed are inner product computations of the first features 210. In such embodiments, an explicit representation of the mapping $\Phi$ nor the nature of the corresponding kernel matrix is required. In such embodiments, it suffices to be able to evaluate the kernel function. Thus, evaluating the kernel on all pairs of first feature 210 measurements in the first plurality of first features across the training set 206 yields a symmetric, positive semidefinite matrix known as the kernel matrix or the Gram matrix. Intuitively, a kernel matrix can be regarded as a matrix of generalized similarity measures among the data points. The first stage of processing in a kernel method is to reduce the data by computing this matrix.

In some embodiments, the model used for the training set 206 is a support vector machine (SVM), which forms a linear discriminant boundary in the kernel matrix. Consider a training set consisting of n pairs $(x_i, y_i)$, where $x_i$ is a first feature measurement 210 for a given reference entity 208 and $y_i$ is a corresponding second feature 212 of the given reference entity 208 and, moreover, $y_i$ is in the form of a label, e.g. $y_i \in \{-1, 1\}$ (e.g. the given reference entity 208 does not have a subject property "−1", the given reference entity 208 does have a subject property "1"). Here, the n×n kernel matrix is computed where the $(i,j)^{th}$ entry is $K(x_i, x_j)$. Given this matrix, and given the labels $y_i$, the original data is no longer needed and the problem of fitting the SVM to data reduces to an optimization procedure that is based entirely on the kernel matrix and the labels.

Different kernel functions correspond to different embeddings of the data and thus can be viewed as capturing different notions of similarity. For example, in a space derived from amino acid sequences, two genes that are close to one another will have protein products with very similar amino acid sequences. This amino acid space would be quite different from a space derived from microarray gene expression measurements, in which closeness would indicate similarity of the expression profiles of the genes. In general, a single type of data can be mapped into many different feature spaces. The choice of feature space is made implicitly via the choice of kernel function. See Lanckriet et al., 2004, "A Statistical Framework for Genomic Data Fusion," Bioinformatics 20, pp. 2626-2635, which is hereby incorporated by reference. Thus, in reference to block 468, a first kernel function is chosen for the respective measurements of each measured first feature in the first plurality of first features in the N-dimensional feature space for each reference entity in the plurality of reference entities thereby computing a first kernel matrix because this first kernel function is suitable for the underlying first molecular assay. A second kernel function is chosen for the respective measurement of each measured first feature in the second plurality of first features in the N-dimensional feature space for each reference entity in the plurality of reference entities thereby computing a second kernel matrix because this second kernel function is suitable for the underlying second molecular assay. As such, in some embodiments, application of the first kernel function produces a first square matrix (first kernel matrix) in which each entry encodes a particular notion of similarity of one first feature to another first feature in the first plurality of first features. Moreover, application of the second kernel function produces a second square matrix (second kernel matrix) in which each entry encodes a particular notion of similarity of one first feature to another in the second plurality of first features. Implicitly, each kernel matrix also defines an embedding of the first features in a feature space. Thus, the kernel representation casts heterogeneous data—data from different molecular assays— into the common format of kernel matrices.

The kernel formalism also allows the various kernel matrices (e.g., the first kernel matrix and the second kernel matrix of block 468) to be combined. Algebraic operations such as addition, multiplication and exponentiation preserve the key property of positive semidefiniteness, and thus allow an algebra of kernels. See Berg et al., 1984, *Harmonic Analysis of Semigroups: Theory of Positive Definite and Related Functions*, Springer, New York, which is hereby incorporated by reference. For example, given the first kernel function $K_1$ and the second kernel function $K_2$, inducing the embeddings $\Phi_1(x)$ and $\Phi_2(x)$, respectively, it is possible to define the kernel $K=K_1+K_2$, inducing the embedding $\Phi(x)=[\Phi_1(x), \Phi_2(x)]$. More generally, a set of kernels $\mathcal{K} = \{K_1, K_2, \ldots, K_m\}$ can be linearly combined $$K = \sum_{i=1}^{m} \mu_i K_i$$

where the weights $\mu_i$ are constrained to be non-negative to assure positive semidefiniteness: $\mu_i \geq 0$; $i=1, \ldots, m$. Then, applying a kernel-based statistical model, such as a support vector machine, to the training set 206 involves solving an optimization problem based on the kernel matrix and the labels (block 470). In particular, the SVM finds a linear discriminant in the kernel matrix that has maximal distance ('margin') between the members of the positive and negative classes. As such, while block 468 is limited to two kernel functions for two corresponding molecular assays, the present disclosure is not so limited. First features from any number of disparate molecular assays reference entities may be measured. In some embodiments, a separate kernel function can be applied to the first features of each corresponding molecular assay to obtain a kernel matrix. These kernel matrices can then be linearly combined. In some such embodiments, the training set comprises first features obtained from three different molecular assays and such data is processed using three different kernel functions which are then combined. In some such embodiments, the training set comprises first features obtained from four different molecular assays and such data is processed using four different kernel functions which are then combined. In some such embodiments, the training set comprises first features obtained from five or more different molecular assays and such data is processed using five or more different kernel functions which are then combined.

Continuing with reference to block 468 and in some embodiments, the feature space of the first and second kernel is combined. In some embodiments, the implicit feature space of the combined kernel is a concatenation of the feature spaces of the first and second kernel functions.

In some embodiments, principal component analysis is applied to the first kernel matrix and the second kernel matrix thereby identifying a plurality of principal components where the plurality of principal components collectively represent the set of first features $\{p_1, \ldots, p_{N-K}\}$ from the N-dimensional feature space. In typical embodiments, principal component analysis is applied to the linear (e.g., weighted) combination of the first and second matrices. In some embodiments, this application of principal component analysis is referred to a kernel principal component analysis. See, for example, Scholkopf, et al., 1999, *Advances in kernel methods*, pp. 327-352, MIT Press Cambridge, Mass., USA, ISBN:0-262-19416-3, which is hereby incorporated by reference. In such embodiments, the training the model using measurements for the set of first features $\{p_1, \ldots, p_{N-K}\}$ across the training set comprises training the model (e.g., SVM) using the plurality of principal components samples for each reference entity in the plurality of reference entities. Typically, in such embodiments the plurality of principal components samples for each reference entity is trained using a second feature 208, wherein the second feature is categorical, or reduced to categorical form.

In some embodiments, principal component analysis is not applied to the linear (e.g., weighted) combination of kernel matrices. In such embodiments, the support vector machine is trained directly on the linear (e.g., weighted) combination of kernel matrices. As discussed above, in some embodiments, in some embodiments, the linear combination of kernel matrices is a linear combination of two or more kernel matrices, three or more kernel matrices, four or more kernel matrices, or five or more kernel matrices.

In some embodiments, principal component analysis is applied to the linear (e.g., weighted) combination of kernel matrices and a support vector machine is not used. That is, in some embodiments, the trained model is the principal components of the principal component analysis.

In some embodiments, the model 214 is a principal components analysis (PCA) model. PCA can be used to analyze first feature data of the training set 206 in order to construct a decision rule that discriminates a label (e.g., a second feature that is encoded as a classification, e.g., ("has property", "does not have property)). PCA reduces the dimensionality of the training set 206 by transforming the first features 212 of the training set to a new set of variables (principal components) that summarize the features of the training set. See, for example, Jolliffe, 1986, Principal Component Analysis, Springer, New York, which is hereby incorporated by reference. PCA is also described in Draghici, 2003, *Data Analysis Tools for DNA Microarrays*, Chapman & Hall/CRC, which is hereby incorporated by reference. Principal components (PCs) are uncorrelated and are ordered such that the $k^{th}$ PC has the $k^{th}$ largest variance among PCs. The $k^{th}$ PC can be interpreted as the direction that maximizes the variation of the projections of the data points such that it is orthogonal to the first k−1 PCs. The first few PCs capture most of the variation in the training set 206. In contrast, the last few PCs are often assumed to capture only the residual 'noise' in the training set 206. As such, PCA can also be used to create a model 214 in accordance with the present disclosure. In such an approach, each row in a table such as that illustrated in FIG. 10 is constructed and represents the measurements for the select first features from a particular reference entity 208 of the training set 206 and can be considered a vector. As such, FIG. 10 can be viewed as a matrix of vectors, each vector representing a respective reference entity and including measurements for first features measured from the respective reference entity. In some embodiments, this matrix is represented in a Free-Wilson method of qualitative binary description of monomers (Kubinyi, 1990, 3D QSAR in drug design theory methods and applications, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been considered. Then, each of the vectors (where each vector represents a reference entity of the training set) is plotted. Many different types of plots are possible. In some embodiments, a one-dimensional plot is made. In this one-dimensional plot, the value for the first principal component from each of the reference entities of the training population is plotted. In this form of plot, the expectation is that reference entities of a first subgroup (e.g. those reference entities that have a first categorical value encompassed by the target second feature 212) will cluster in one range of first principal component values and reference entities of a second subgroup (e.g., those reference entities that have a second categorical value encompassed by the target second feature 212) will cluster in a second range of first principal component values. In some embodiments, the reference entities 208 of the training set 206 are plotted against more than one principal component. For example, in some embodiments, the reference entities 208 of the training set 206 are plotted on a two-dimensional plot in which the first dimension is the first principal component and the second dimension is the second principal component. In such a two-dimensional plot, the expectation is that reference entities of each subgroup represented in the training set will cluster into discrete groups. For example, a first cluster of reference entities in the two-dimensional plot will represent reference entities that have a first categorical value encompassed by a first target second feature 212 and as well as a first categorical value encompassed by a second target second feature 212 (encoded 0,0) whereas a second cluster of reference entities in the two-dimensional plot will represent reference entities that that have a second categorical value encompassed by the first target second feature 212 and as well as a first categorical value encompassed by the second target second feature 212 (encoded 1,0).

Referring to block 472 of FIG. 4E, in some embodiments, a plurality of first features 210 in the N-dimensional feature space is obtained from a molecular assay of each reference entity 208 in the training set. In embodiments in accordance with block 472, the feature selection method comprises: (i) application of a kernel function to the respective measurement of each first feature 210 in the plurality of first features in the N-dimensional feature space for each reference entity 208 in the plurality of reference entities (or a subset thereof) thereby deriving a kernel matrix. In some such embodiments, the kernel matrix is used to directly train a support vector machine. In other embodiments dimension reduction is first invoked prior to training a support vector machine. For instance, in some embodiments principal component analysis is applied to the kernel matrix to thereby identifying a plurality of principal components where the plurality of principal components collectively represent the set of first features $\{p_1, \ldots, p_{N-K}\}$ from the N-dimensional feature space. While the plurality of principal components collectively represent the set of first features $\{p_1, \ldots, p_{N-K}\}$ from the N-dimensional feature space, it is not necessarily the case that each first feature in the set of first features $\{p_1, \ldots, p_{N-K}\}$ contributes to a principal component. For instance, the principal component analysis may determine that some of the first features do not contribute to explaining variation of a target second feature 212 and thus does not incorporated these first features into principal components. Continuing to refer to block 472, in embodiments were principal component analysis is used, the training of the model (e.g., support vector machine) using measurements for the set of first features $\{p_1, \ldots, p_{N-K}\}$ across the training set comprises training the model using the plurality of principal components samples for each reference entity in the plurality of reference entities. In typical embodiments, the training of the model (e.g., support vector machine) using measurements for the set of first features $\{p_1, \ldots, p_{N-K}\}$ across the training set comprises training the model using the plurality of principal components samples for each reference entity in the plurality of reference entities and measurements for one or more second features 212 in each reference sample in the training set.

Referring to block 474 of FIG. 4F, in some embodiments, kernel functions are not applied to the measurements of the first features 210 in the training set. In such embodiments, the feature selection method comprises application of principal component analysis to the training set thereby identifying a plurality of principal components. The plurality of principal components collectively represent the set of first features $\{p_1, \ldots, p_{N-K}\}$ from the M-dimensional feature space across the training set. While the plurality of principal components collectively represent the set of first features $\{p_1, \ldots, p_{N-K}\}$ from the N-dimensional feature space, it is not necessarily the case that each first feature in the set of first features $\{p_1, \ldots, p_{N-K}\}$ contributes to a principal component. For instance, the principal component analysis may determine that some of the first features do not contribute to explaining variation of a target second feature 212 and thus does not incorporated these first features into principal components. Continuing to refer to block 474, in embodiments where principal component analysis is used, the training of the model 214 using measurements for the set of first features $\{p_1, \ldots, p_{N-K}\}$ across the training set comprises training the model using the plurality of principal components samples for each reference entity 208 in the plurality of reference entities and measurements for one or more second features 212 in each reference sample in the training set. In some embodiments the model is a support vector machine (block 476).

In embodiments, of the present disclosure, a model is trained using measurements of the first features across the training set 206 against a target (e.g., directly measurements of the first features, kernel matrices built from such measurements, principal components of direct measurements or kernel matrices), where the target is either measurements of a second feature 212 across the training set 206 or some combination of measurements of a plurality of second features 212 across the training set 206. Moreover, just as the first features 210 may be projected into a higher dimensional space using one or more kernel functions and/or subjected to dimension reduction techniques such as by subset selection, a shrinkage method or principal component analysis, so may the second features 212.

Blocks 478 and 480 of FIG. 4F provide non-limiting examples of second features 212. Referring to block 478, in some embodiments, the training of block 458 further comprises training the model 214 using measurements of each corresponding reference entity 208 in the training set 206 for a single second feature 212 selected from the group consisting of dye penetration, viscosity, gelation, texture, angled layering, layer strength, flow consistency, and gelling speed.

In some embodiments, gelation is tested by applying small-amplitude oscillatory tests in which a small sinusoidal strain (or stress) to the reference entity and measuring the resulting stress (or strain). These small-amplitude oscillatory tests are commonly performed in shear and therefore have the abbreviation SAOS, for small-amplitude oscillatory shear. In some embodiments, the strains (or stresses) used in SAOS tests are on the order of 1 to 3 or 5% to assure that the material response is in the linear range—the range in which the stress is proportional to the applies strain. See Gunasekaren and Mehmet, 2000, "Dynamic oscillatory shear testing of foods—selected applications," Trends in Food Science & Technology 11, pp. 115-127, which is hereby incorporated by reference.

Some of the most popular foods, such as gelatin desserts, cooked egg whites, frankfurters, surimi based seafood analogs, and fruit jellies, can be considered gels. A gel is a solid-in-liquid colloid in which the solid phase forms a network structure that immobilizes the liquid and produces solid-like properties. A gel can also be described as a substantially diluted system that exhibits no steady state flow. The initial state can be a solution, dispersion, or suspension. Some food gels are formed irreversibly by cooking, while others like gelatin form reversible gels. Gelation arises either from chemical cross-linking by way of covalent reactions or from physical cross-linking through polymer-polymer interactions. See Tabilo-Munizaga and Barbosa-Canovas, 2005, Journal of Food Engineering 67, pp. 147-156, which is hereby incorporated by reference. Stress-strain tests are useful in studying the behavior of food gels and generally can be categorized as two types, small-strain testing and large-strain testing. Small-strain testing refers to deforming a sample when only a small percentage of the deformation is required to break the sample, which often is performed by fundamental tests. Large-strain testing refers to deforming a sample to the point of permanent structural change. Moreover, large strain testing often yields information that correlates with sensory evaluation. In some embodiments, a second feature is gelation that is measured by a small-strain test or a large-strain test. Tabilo-Munizaga and Barbosa-Canovas, 2005, Journal of Food Engineering 67, pp. 147-156, which is hereby incorporated by reference, describes exemplary small-strain test or a large-strain tests that can be used to measure second features 212 in accordance with embodiments of the systems and methods of the present disclosure. In some embodiments, the second feature 212 is measured using a large-strain test such a puncture test, a uniaxial compression test, a torsion test, or a folding test as described in Tabilo-Munizaga and Barbosa-Canovas, 2005, Journal of Food Engineering 67, pp. 147-156, which is hereby incorporated by reference. In some embodiments, the second feature is measured using a small-strain test such an oscillatory test, a stress relaxation test, or a yield stress determination as described in Tabilo-Munizaga and Barbosa-Canovas, 2005, Journal of Food Engineering 67, pp. 147-156, which is hereby incorporated by reference. In some embodiments, the second feature 212 is measured using a rheological test such as steady shear rate-shear stress, time dependent shear rate-shear stress, stress growth and decay at a constant shear rate, dynamic viscoelastic behavior, and creep-compliance viscoelastic behavior as disclosed in Rao, 1999, "Rheological behavior of processed fluid and semisolid foods" in M. A. Rao (ed.), *Rheology of fluid and semisolid foods: principles and applications*, Chapters 3 and 5, pp. 105-108, and 244-254, which is hereby incorporated by reference.

Figure 8:
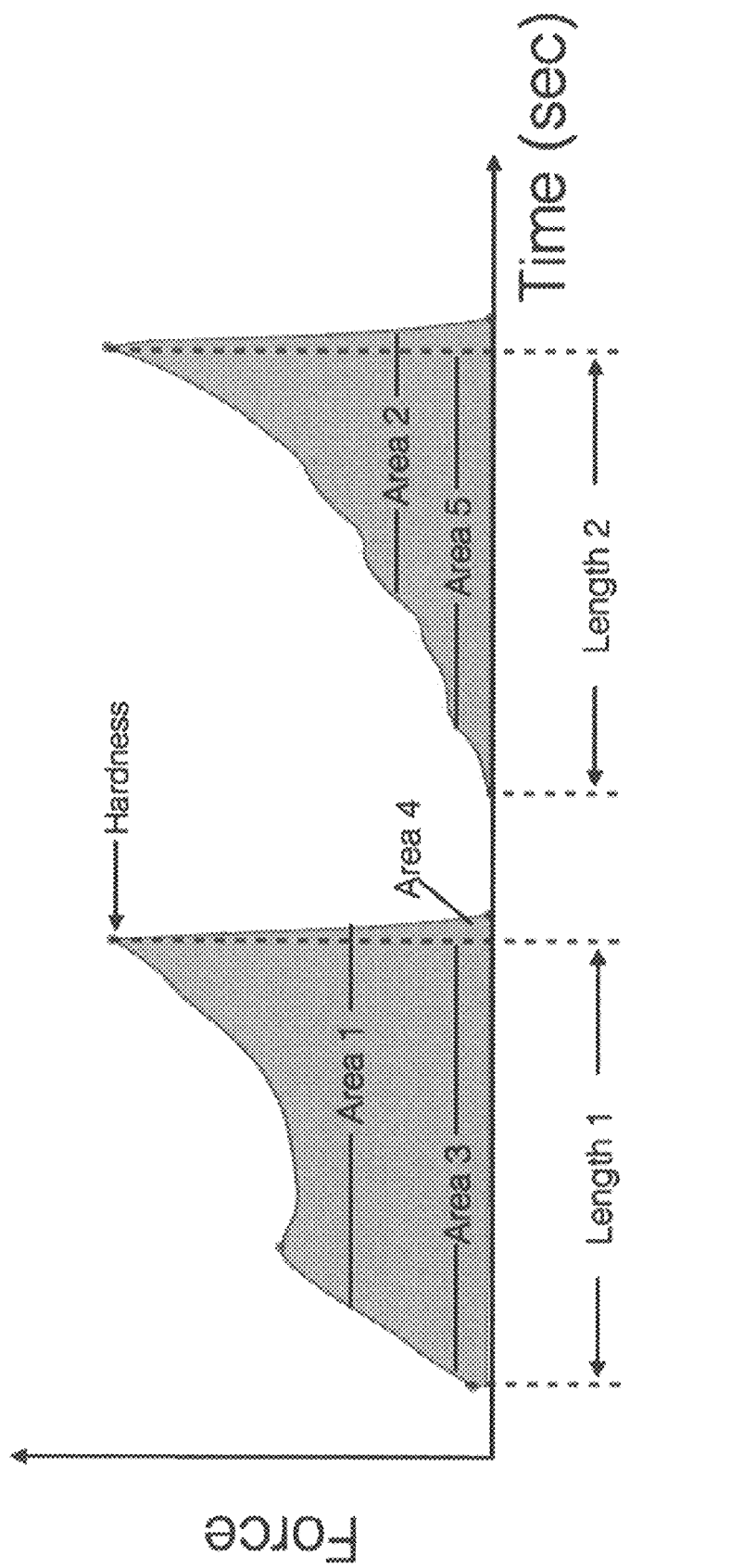
FIG. 8 illustrates how quantitative measurements of textural features can be extracted from a texture profile analysis of physical food samples via a probe used to compress the sample in accordance with an embodiment of the present disclosure.

Referring to block 480, in some embodiments, the training further comprises training the model 214 using measurements of each corresponding reference entity 208 in the training set 206 for a single second feature 212 that is hardness, fracturability, cohesiveness, springiness, chewiness, or adhesiveness as determined by a texture profile analysis (TPA) assay. See Pons and Fiszman, 1996, Journal of Texture Studies 27, 597-624, which is hereby incorporated by reference. TPA allows for the objective measurement of texture by imitating the chewing process. TPA obtains the profile of the force that must be applied to chew products by subjecting a sample of the product on two consecutive occasions to a force that is similar to the biting strength of the jaw and, in this example five textural parameters are measured, hardness (kg m s$^{-2}$), springiness (adimensional), cohesiveness (adimensional), chewiness (kg) and resilience (adimensional). TPA data of a typical sample is often graphed as a curve with two dimensions: time vs. magnitude of compression force. Quantitative measurements of textural features can be extracted from the curve as illustrated in FIG. 8. Hardness is defined as the peak force during the first compression. Springiness is defined as the time it takes to achieve maximum force during the second compression (length 2) divided by the time it takes to achieve maximum force during the first compression (length 1). Cohesiveness is defined by the total area of the second peak (Area 2) divided by the total area of the first peak (Area 1). Chewiness is defined as hardness*cohesiveness*springiness. Resilience is defined as the area under the first peak following the maximum of the first peak (Area 4) divided by the area under the first peak prior to the maximum of the first peak (Area 3).

Referring to block 482, of FIG. 4F, once a model 214 has been selected and trained with the training set, in accordance with the methods disclosed above, it is possible to classify test entities without any requirement that such test entities be assayed against the second features 212. Moreover, the final trained model 214 developed using the systems and methods of the present disclosure typically do not use a number of the first features 210 in the training set. As such, in using a trained model to classify a given test entity, it is only necessary to obtain measurements of a limited set of first features 220-X-1 through 220-1-Y, where Y is a positive integer that is typically much less than N. In some embodiments Y is an order of magnitude smaller than N. For instance, in some embodiments N is 500 and Y is 30.

Referring to block 484, the set of first features $\{p_1, \ldots, p_{N-K}\}$ of the test entity 218 are inputted into the trained model thereby obtaining a trained model output value for the test entity. For instance, in the case where the trained model is a linear regression model of the form:

$$f(X) = \beta_0 + \Sigma_{j=1}^{t} X_j \beta_j$$

described above, $\{X_1, \ldots, X_t\}$ is computed using the set of first features $\{p_1, \ldots, p_{N-K}\}$ of the test entity and the value f(X) is computed using the parameters $\beta_0, \beta_1, \ldots, \beta_t$ that were determined by training the model. Examples 1 through 3, below, provide additional examples of how the set of first features $\{p_1, \ldots, p_{N-K}\}$ of the test entity 218 are inputted into the trained model thereby obtaining a trained model output value for the test entity. Referring to block 486 of FIG. 4F, the trained model output value of the test entity 218 is compared to one or more trained model output values computed using measurement values for the set of first features $\{p_1, \ldots, p_{N-K}\}$ of one or more reference entities that exhibits the target property thereby determining whether the test entity exhibits the target property. For instance, consider the case of the linear regression model above in which all reference entities that have a target property score a value of between 0.5 and 0.75 for f(X) whereas all reference entities 208 that do not have the target property score a value of between 0.25 and 0.45 for f(X). In accordance with block 486, if the test entity scores a value of 0.6 for f(X), then the test entity is deemed by the model to have the target property.

Figure 4G:
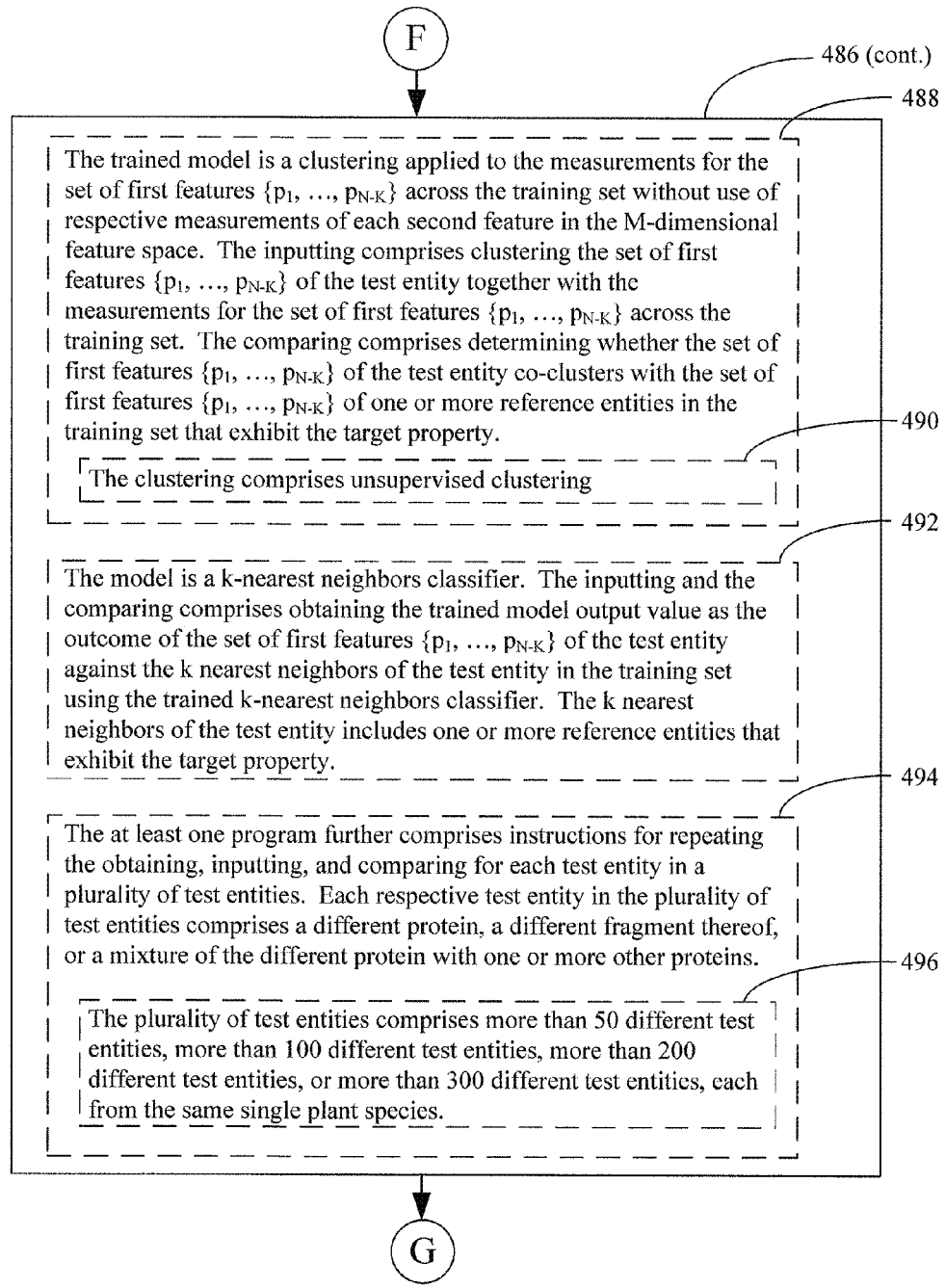

Referring to block 488 of FIG. 4G, in some embodiments the trained model is a clustering applied to the measurements for the set of first features $\{p_1, \ldots, p_{N-K}\}$ across the training set without use of respective measurements of each second feature in the M-dimensional feature space. In some such embodiments, the inputting of block 484 comprises clustering the set of first features $\{p_1, \ldots, p_{N-K}\}$ of the test entity together with the measurements for the set of first features $\{p_1, \ldots, p_{N-K}\}$ of the reference entities 208 across the training set 206. In some embodiments, the training set 206 is used to identify principal components using principal component analysis and the values of these principal components across the reference entities 208 and the test entity 218 are co-clustered together. In accordance with block 488, the comparing of block 486 comprises determining whether the set of first features $\{p_1, \ldots, p_{N-K}\}$ of the test entity 218 (or the principal components derived from the set of first features) co-clusters with the set of first features $\{p_1, \ldots, p_{N-K}\}$ (or the principal components derived from the set of first features) of one or more reference entities in the training set that exhibit the target property.

To illustrate how the set of first features $\{p_1, \ldots, p_{N-K}\}$ are used in clustering, consider the case in which ten first features 210 are used. In some embodiments, each reference entity 208 of the training set 206 will have measurement values (e.g. expression values) for each of the ten first features 210. In some embodiments, each reference entity 208 of the training set 206 has measurement values (e.g. expression values) for only some of the ten first features 210 and the missing values are either filled in using imputation techniques or ignored (marginalized). In some embodiments, each reference entity 208 of the training set 206 has measurement values (e.g. expression values) for only some of the ten first features 210 and the missing values are filled in using constraints such as those disclosed in Wagstaff, 2004, *Classification, Clustering and Data Mining Applications*, Chapter 61 "Clustering with Missing Values: No Imputation Required," which is hereby incorporated by reference.

The measurements from a reference entity 208 in the training set 206 define the vector: $X_1$, $X_2$, $X_3$, $X_4$, $X_5$, $X_6$, $X_7$, $X_8$, $X_9$, $X_{10}$ where $X_i$ is the measurement level of the $i^{th}$ first feature in the set of first features $\{p_1, \ldots, p_{N-K}\}$ for a particular reference entity 208. If there are Q reference entities in the training set 206, selection of the 10 first features will define Q vectors. Note that, as discussed above, the systems and methods of the present disclosure do not require that each measurement value of every single first feature used in the vectors be represented in every single vector Q. In some embodiments, data from a reference entity 208 in which one of the $i^{th}$ first features 210 has not been measured can still be used for clustering by assigning the missing first feature a value of either "zero" or some other normalized value. In some embodiments, prior to clustering, the first feature measurement values in the vectors are normalized to have a mean value of zero (or some other predetermined mean value) and unit variance (or some other predetermined variance value).

Those members of the training set 206 that exhibit similar measurement patterns across their respective vectors will tend to cluster together. A particular combination of set of first features $\{p_1, \ldots, p_{N-K}\}$ is considered to be a good classifier in this aspect of the present disclosure when the vectors cluster into identifiable groups found in the training set 206 with respect to a target second feature 212. For instance, if the training set includes class a: reference entities that have class 1 for the target second feature (and therefore are deemed to have the target property), and class 2 for the target second features (and therefore are deemed to not have the target property) an ideal clustering model 214 will cluster the training set 206 and, in fact, the test entities 218, into two groups, with one cluster group uniquely representing class 1 and the other cluster group uniquely representing class 2 for the target second feature.

Clustering is described at pages 211-256 of Duda and Hart, *Pattern Classification* and Scene Analysis, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in the training set. If distance is a good measure of similarity, then the distance between reference entities in the same cluster will be significantly less than the distance between the reference entities in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 218 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973.

More recently, Duda et al., Pattern Classification, $2^{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, Cluster analysis (3d ed.), Wiley, New York, N.Y.; and Backer, 1995, Computer-Assisted Reasoning in Cluster Analysis, Prentice Hall, Upper Saddle River, N.J., each of which is hereby incorporated by reference. Particular exemplary clustering techniques that can be used in the present disclosure include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. Such clustering can be on the set of first features $\{p_1, \ldots, p_{N-K}\}$ (or the principal components derived from the set of first features).

In some embodiments, the clustering comprises unsupervised clustering (block 490) where no preconceived notion of what clusters should form when the training set is clustered are imposed.

Referring to block 492, in some embodiments, the model 214 is a k-nearest neighbors classifier. In such embodiments, the inputting of block 484 and the comparing of block 486 comprises obtaining the trained model output value as the outcome of the set of first features $\{p_1, \ldots, p_{N-K}\}$ of the test entity 218 against the k nearest neighbors of the test entity in the training set 206 using the trained k-nearest neighbors classifier. If the k nearest neighbors of the test entity includes one or more reference entities that exhibit the target property, the test entity is also deemed to exhibit the target property.

Nearest neighbor classifiers are memory-based and require no classifier to be fit. Given a query point $x_0$, the k training points $x_{(r)}$, r, $\ldots$, k closest in distance to $x_0$ are identified and then the point $x_0$ is classified using the k nearest neighbors. Ties can be broken at random. In some embodiments, Euclidean distance in feature space is used to determine distance as:

$$d_{(i)} = \|x_{(i)} - x_{(0)}\|$$

In some embodiments, when the nearest neighbor algorithm is used, the measurement data for the first features used to compute the linear discriminant is standardized to have mean zero and variance 1. In the present disclosure, the reference entities 208 of the training set 206 are randomly divided into a training population and a test population. For example, in one embodiment, two thirds of the members of the training set 206 are placed in a training population and one third of the members of the training set are placed in a test population. The set of first features $\{p_1, \ldots, p_{N-K}\}$ represents the feature space into which reference entities of the test population are plotted. Next, the ability of the training population to correctly characterize the members of the test population is computed. In some embodiments, nearest neighbor computation is performed several times for a given set of first features $\{p_1, \ldots, p_{N-K}\}$. In each iteration of the computation, the members (reference entities 208) of the training set 206 are randomly assigned to the training population and the test population. Then, the quality of the given set of first features $\{p_1, \ldots, p_{N-K}\}$ is taken as the average of each such iteration of the nearest neighbor computation.

In some embodiments, the nearest neighbor rule is refined to address issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc.; and Hastie, 2001, *The Elements of Statistical Learning*, Springer, New York, each of which is hereby incorporated by reference in its entirety.

Referring to block 494, advantageously, the systems and methods of the present disclosure allows for the rapid screening of test entities 218 for a target property without having to measure second features 212 that serve as a metric for the target property. Rather, simple molecular tests that have no apparent ability or directly observable correlation with the target property are measured for the test entity and applied to a trained classifier 214 to ascertain whether the test entity has the target property. As such, in some embodiments, the at least one program further comprises instructions for repeating the obtaining (e.g., as described at block 482), inputting (e.g., as described at block 484), and comparing (e.g., as described at block 486) for each test entity 218 in a plurality of test entities. In some such embodiments, each respective test entity 218 in the plurality of test entities comprises a different protein, a different fragment thereof, or a mixture of the different protein with one or more other proteins. In other embodiments, each respective test entity 218 in the plurality of test entities comprises a different one of any of the compositions disclosed herein (e.g., an organic molecule derived from living organisms such as protein (e.g., unmodified protein, sulfated, acylated or glycosylated protein, non-ribosomal peptide), amino acid, oil (e.g., triglyceride, sterols and other neutral lipids), polar lipid (e.g., phospholipids, glycolipids, sphingolipids), carbohydrate (e.g., polysaccharide, oligosaccharide, disaccharide, monosaccharide), sugar alcohol, phenol, polyphenol, nucleic acid, polynucleic acid, polyketide, a xenobiotic compound, combinations and covalently-bound combinations thereof (e.g., e.g. glycosidic protein or protein-bound lipid), and/or mixtures thereof (e.g., an oil and a phospholipid, etc.). In this way, referring to block 496 of FIG. 4G, in some embodiments, the plurality of test entities comprises more than 50 different test entities, more than 100 different test entities, more than 200 different test entities, or more than 300 different test entities, that are screened by the systems and methods of the present disclosure. In some embodiments, each of these entities is from the same single plant species. In some embodiments, more than 50 different test entities, more than 100 different test entities, more than 200 different test entities, or more than 300 different test entities are screened by the systems and methods of the present disclosure in less than 1 week, less than 1 day, or less than 8 hours.

As noted in block 494, the systems and methods of the present disclosure afford high throughput screening of test entities by obviating the need to perform functional assays on such test entities. In order to find a suitable entity that has the target property, in some instances it is necessary to assay numerous test entities from numerous different sources (e.g., numerous different plants). Moreover, in some embodiments it is too cost prohibitive to fully characterize a test entity 218 prior to testing. In such embodiments, rather than fully characterizing the test entity, basic information regarding the test entity, such as the source plant or source plants of the test entity combined with basis information regarding how the test entity was extracted from the source plant or plants is placed in the data structure 302 uniquely associated with the given test entity. In this way, if the model 214 indicates that the test entity has the target property, it is possible to reconstruct how to extract more of the test entity from the source plants. As an example, consider the case where plant A is crushed, solubilized, and the extract from the plant is run through column B at a flow rate of C using a buffer gradient D. Fractions of the column elute are taken periodically and the average time or the start time or the end time of each fraction is recorded. In this example, by recording the source plant, the column used for purification, the flow rate of the column, the buffer gradient used, and the elution time of the test entity in the data structure 302 uniquely associated with the test entity, more of the test entity sample can be obtained if it turns out that the test entity is deemed by a trained model to have the target property. From this additional sample of the test entity, the molecular assays on the test entity can be rerun on the same or different trained models for confirmation and/or more time consuming functional assays can be run on the test entity. Moreover, if the test entity comprises a plurality of compounds, each such compound can be purified, assayed using the molecular assays, and tested by the trained model and/or directly assayed for the target property by assaying the purified compound with the functional assays.

As the forgoing suggests, data management problems can arise if the data associated with a test entity, such as its origin and how it was extracted, are not suitably tracked. Advantageously, referring to block 498, in some embodiments, each test entity 316 is extracted from a plant and the at least one program (e.g., the screening module 204) further comprises instructions for associating one or more data structures with the test entity. FIG. 3 illustrates an exemplary data structure 302 within the ambit of block 494. In some embodiments, the data structure 302 identifies the test entity 218, an extraction parameter 304 for the test entity 218, and a characteristic 316 of the source plant.

Figure 4H:
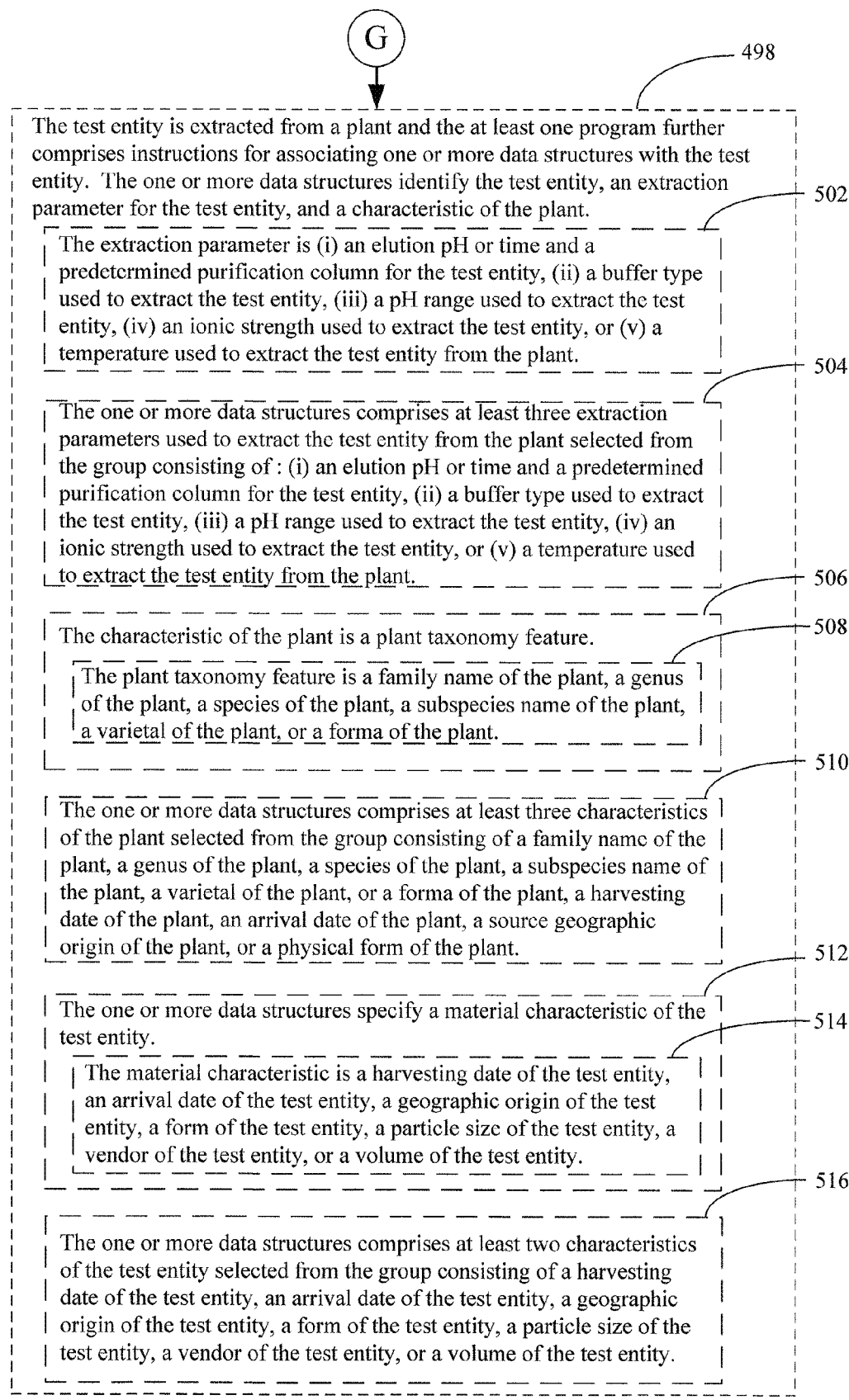

Referring to block 502 of FIG. 4H and FIG. 3, in some embodiments, the extraction parameter 304 is (i) an elution pH or time and a predetermined purification column type 306 for the test entity 218, (ii) a buffer type 308 used to extract the test entity 218, (iii) a specific pH or pH range 310 used to extract the test entity 218, (iv) a specific ionic strength or an ionic strength range 312 used to extract the test entity 218, or (v) a specific temperature or temperature range 314 used to extract the test entity 218 from the plant(s).

Referring to block 504 of FIG. 4H and FIG. 3, in some embodiments, the one or more data structures 302 comprises at least three extraction parameters 304 used to extract the test entity 218 from the plant(s) selected from the group consisting of: (i) an elution pH or time and a predetermined purification column type 306 for the test entity 218, (ii) a buffer type 308 used to extract the test entity 218, (iii) a pH range 310 used to extract the test entity 218, (iv) an ionic strength 312 used to extract the test entity 218, or (v) a temperature 314 used to extract the test entity 218 from the plant.

Referring to block 506 of FIG. 4H and FIG. 3, in some embodiments, the characteristic of the source plant (or plants) 316 is a plant taxonomy feature. For instance, referring to block 508, in some embodiments, the plant taxonomy feature is a family name 318 of the plant, a genus 320 of the plant, a species 322 of the plant, a subspecies name 324 of the plant, a varietal 326 of the plant, or a forma 328 of the plant.

Referring to block 510 of FIG. 4H and FIG. 3, in some embodiments, the one or more data structures 302 comprises at least three characteristics 316 of the plant (or source plants in the case where multiple plants were used to source a single test entity) selected from the group consisting of a family name 318 of the plant, a genus 320 of the plant, a species 322 of the plant, a subspecies name 324 of the plant, a varietal 326 of the plant, a forma 328 of the plant, a harvesting date 330 of the plant, an arrival date 332 (e.g., the date the plant arrived at the lab where molecular assays are performed on the test entity extracted from the plant) of the plant, a source geographic origin 334 of the plant, or a physical form 336 of the plant.

Referring to block 512 of FIG. 4H and FIG. 3, in some embodiments, the one or more data structures 302 specify a material characteristic 338 of the test entity. For instance, referring to block 514, in some embodiments, the material characteristic 338 is a harvesting date 340 of the test entity, an arrival date 342 of the test entity, a geographic origin 344 of the test entity, a form 346 of the test entity, a particle size 348 of the test entity, a vendor 350 of the test entity, or a volume 352 of the test entity.

Referring to block 516 of FIG. 4H and FIG. 3, in some embodiments, the one or more data structures 302 comprises at least two characteristics of the test entity selected from the group consisting of a harvesting date 340 of the test entity, an arrival date 342 of the test entity, a geographic origin 344 of the test entity, a form 346 of the test entity, a particle size 348 of the test entity, a vendor 350 of the test entity, or a volume 352 of the test entity.

In some embodiments, data structure 302 stores additional information regarding test entities, such as publically available information such as the *Arabidopsis* Information Resource (TAIR), which provides plant pathways and compound database, metabolite profiling data. In some embodiments, data structure 302 stores additional information regarding test entities, such as from the Plant Metabolic Network (PMN) which provides metabolic pathways from a large number of plants that are cataloged in PMN's PlantCyc database and experimentally supported, computationally predicted, and hypothetical pathways and enzymes. PMN is also a gateway to species-specific pathway databases for several plants, including *Arabidopsis*, rice, tomato, medicago, and poplar. In some embodiments, the data structures 302 store metabolite profiling data regarding test entities, (e.g., metabolite response statistics, raw and processed GC/MS data, data matrices, mass-spectrum and retention-index libraries and standards-compliant metadata).

In some embodiments, additional information regarding test entities 218 is stored in the data structures 302, such as protein sequence length of a protein in the test entity 218, replicon, molecular weight, type/subunits, small molecule regulator, cofactor, substrate or ligand, evidence code, cell component, organism and protein features of components in the test entity.

In some embodiments, additional information regarding test entities 218 is stored in the data structures 302, such as information regarding presence of bioactive peptides, glycans, lipids, polyketides, nonribosomal peptides, secondary metabolites and xenobiotic compounds in the test entities. In some embodiments, such information is in accordance with the standards of the KEGG Compound database.

In certain aspects, the target properties of replacement ingredients identified in test entities 218 using the systems and methods of the present disclosure can be assessed in finished products. Such target properties include but are not limited to achieving a desired crumb density, structure/texture, elasticity/springiness, coagulation, binding, mouthfeel, leavening, aeration/foaming, creaminess, and emulsification of the food product. The target properties described above can overlap or may be interdependent. In some embodiments, the replacement ingredient can functionally replace a traditional ingredient in baked goods and/or emulsions. In some embodiments, the replacement ingredients replace traditional ingredients on a weight basis.

In some embodiments, the target finished product is a powderized protein composition. In some such embodiments, the powderized protein composition is a flour. As such, in some embodiments, one or more test entities 218 that have been selected as being suited for this purpose by a trained model 214 in accordance with the systems and methods of the present disclosure are used to form the flour. In some embodiments, the flour is a powder ground from grains, seeds, roots, or other forms of test entities 214 selected by the trained model 214. Most flours have a high starch content which imparts thickening and binding properties, and may provide moisture content. In some embodiments, the flour that is produced in this way is a suitable substitute for all purpose flour, unbleached flour, bleached flour, bread flour, self-rising flour, wheat flour, cake flour, acorn flour, almond flour, amaranth flour, atta flour, rice flour, buckwheat flour, cassava flour, chestnut flour, chuno flour, coconut flour, corn (maize) flour, hemp flour, maida flour, mesquite flour, nut flour, peanut flour, potato flour, rice flour, rye flour, tapioca flour, t'eff flour, soy flour, peanut flour, arrowroot flour, taro flour, acorn flour, bean flours such as, e.g., soy flour, garbanzo flour, fava bean flour, pea flour; or other flour. In some embodiments, the test entity 218 that is selected to make this flour is from Sorghum, White sorghum, Soy bean, Millet, Vallarta, Stueben, Green fagelot, Black beluga, Black calypso, Chana dal, Amaranth, Lentil, Red lentil, Black lentil, Golden lentil, Do pung-style lentil, Sprouted green lentil, Sweet brown rice, Navy bean, Red bean, Pink bean, Canellini bean, Giant white lima bean, Christmas lime bean, Baby lima bean, Mung bean, Peeled fava bean, Good mother stellard bean, Cranberry chorlottis bean, Santa maria pinguinto bean, Brown tepary bean, Black turtle bean, Yellow slit pea, Canadian yellow pea, or Black turtle beans.

In some embodiments, the target finished product is a starch substitute. As such, in some embodiments, one or more test entities 218 that have been selected as being suited for this purpose by a trained model 214 in accordance with the systems and methods of the present disclosure are used to form the starch substitute. In some embodiments, the starch that is produced in this way is a suitable substitute for arrowroot starch, corn starch, tapioca starch, mung bean starch, potato starch, sweet potato starch, rice starch, sago starch, or wheat starch. Here, the term "starch" refers to polysaccharide materials, often produced by plants to act as energy stores.

In some aspects, the systems and method of the present disclosure provide a food product prepared using one or more test entities 218 selected by one or more trained models 214 as described herein, where the food product is indistinguishable from an equivalent product prepared using conventional ingredients. In some embodiments, the food product is a baked food product. Such baked food products include cookies, brownies, cake, and the like. In some embodiments, the food product is a sauce, dressing, or custard. In some embodiments, the food product is an ice cream, pasta, meatloaf, or burger patty. In some embodiments the food product is an emulsion, such as mayonnaise or dressings.

Representative First Features 210.

In some embodiments a first feature 210/218 that is measured for a reference entity 208 and/or a test entity 218 comprises protein state, charge, stability, protein content, molecular weight (e.g., average molecular weight or molecular weight distribution), pH, solubility, protein bond interactions (e.g., this could involve interactions beyond covalent interactions—ionic, hydrophobic bonds etc.), concentration, isoelectric point, hardness, viscosity, moisture content, volume, specific gravity, density, phase transition, temperature (pressure and humidity dependence thereof), extensibility, phospholipid concentration, a textural feature, aggregation of the corresponding entity.

In some such embodiments, a first feature 210/218 that is measured for each reference entity 208 and test entity 218 is protein concentration, such as total protein quantitation. Total protein quantitation is a common measurement in life science, biopharmaceutical and food and beverage laboratories. Some of the most frequently used assays for total protein quantitation are dye binding assays, such as the Coomassie-based Bradford Assay and can be used for the purpose of determining protein concentration in the present disclosure. However, many substances, including some detergents, flavonoids and protein buffers are known to interfere with the colorimetric properties Bradford Assay relies on. Additionally, the linearity of the Bradford Assay is limited in both quality and range. Accordingly, in some embodiments protein concentration is measured using the Thermo Scientific Pierce 660 nm Assay. In some embodiments, this assay is performed on a Thermo Scientific UV-Visible spectrophotometer with embedded BioTest software, such as the Evolution™ 60S, BioMate™ 3S or GENE-SYS™ 10S Bio, or equivalents thereof. In some embodiments, a reference protein such as Bovine Serum Albumin (BSA) or Bovine Gamma Globulin (BGG) is used in the protein concentration assay. See Keppy, Thermo Fisher Scientific, Madison Wis., Application Note: 51839, which is hereby incorporated by reference.

In some embodiments a first feature 210/220 that is measured is a fat content description expressed on a numeric scale or categorically. In some such embodiments, the fat content is expressed categorically, where the categorical value for fat content is selected from the set {oily, non-oily, greasy, and non-greasy}, subsets thereof, and supersets thereof.

In some embodiments a first feature 210/220 that is measured is texture expressed on a numeric scale or categorically. In some such embodiments, the texture is hardness expressed on a numeric scale or categorically. In some such embodiments, the texture is hardness expressed categorically, where the categorical value for hardness is selected from the set {soft, firm, and hard}, subsets thereof, or supersets thereof. In some such embodiments, the texture is cohesiveness expressed on a numeric scale or categorically. In some such embodiments, the texture is cohesiveness expressed categorically, where the categorical value for cohesiveness is selected from the set {crumbly, crunchy, brittle, chewy, tender, tough, mealy, pasty, and gummy}, subsets thereof, or supersets thereof.

In some embodiments a first feature 210/220 that is measured is viscosity expressed on a numeric scale or categorically. In some such embodiments, the viscosity is expressed categorically, where the categorical value for viscosity is selected from the set {thin, and viscous}, subsets thereof, or supersets thereof.

In some embodiments a first feature 210/220 that is measured is particle size expressed on a numeric scale or categorically. In some such embodiments, the particle size is expressed categorically, where the categorical value for particle size is selected from the set {grainy, and course} or supersets thereof. In some embodiments a first feature 210/220 that is measured is particle distribution expressed on a numeric scale or categorically.

In some embodiments a first feature 210/220 that is measured is particle shape and orientation expressed on a numeric scale or categorically. In some such embodiments, the particle shape and orientation is expressed categorically, where the categorical value for particle shape and orientation description is selected from the set {fibrous, cellular, and crystalline}, subsets thereof, and supersets thereof.

In some embodiments a first feature 210/220 that is measured is moisture content expressed on a numeric scale or categorically. In some such embodiments, the moisture content is expressed categorically, where the categorical value for moisture content is selected from the set {moist, wet, and watery}, subsets thereof, and supersets thereof.

In some embodiments a first feature 210/220 that is measured is viscosity. Exemplary techniques for measuring viscosity and the types of viscosity that can be measured are described in Malcom, 2002, Food Texture and Viscosity, Second Edition, Chapter 6 "Viscosity Measurement," pp. 235-256, Elsevier Inc., and (W. Boyes, ed.), 2009, *Instrumentation Reference Book*, Fourth Edition, Chapter 7, pp. 69-75, "Measurement of Viscosity," each of which is hereby incorporated by reference.

Representative Second Features.

In general, a second feature 212 is any metric that represents a desired outcome or target property for a food ingredient. As such, any of the features that are disclosed as first features herein may, in some implementations, be coded as a second feature rather than as a first feature when such second features represent a desired outcome or target property for such implementations. In typical implementations, second features are harder to assay than first features, though this is not always the case.

Representative second features 212 that can be used in any of the embodiments of the present disclosure include, but are not limited to, structure, emulsification ability, stability, water binding ability, phase separation, oil holding capacity, foaming ability, coalescence, gelling, gelation, caramelization, aeration, chewiness, gumminess, springiness, sensory (taste, texture, flavor, aroma, mouthfeel, aftertaste, finish, appearance), syneresis, cohesiveness, brittleness, elasticity, adhesiveness, shelf-life, color, and odor.

In some embodiments a second feature 210 is flavor expressed categorically. In some such embodiments, the categorical values for flavor are selected from the set {sweet, sour, bitter, salty, savory, pungent, metallic, spicy, eggy, fishy, buttery, chocolaty, fruity, peppery, baconlike, creamy, milky, beefy, fatty, nutty, sweaty, fruity, rancid, and beany}, subsets thereof, or supersets thereof.

In some such embodiments a second feature 212 is elasticity expressed on a numeric scale or categorically. In some such embodiments, the elasticity is expressed categorically, where the categorical values for elasticity are selected from the set {plastic, and elastic}, or supersets thereof.

In some embodiments a second feature 212 that is measured is adhesiveness expressed on a numeric scale or categorically. In some such embodiments, the adhesiveness is expressed categorically, where the categorical value for adhesiveness is selected from the set {tacky, and gooey} or supersets thereof.

In some embodiments a second feature 212 that is measured is structure stability observed through yield stress analysis. Materials with structure can absorb the stress being applied until the structure starts to breakdown. The result is an increase in viscosity as the structure is maintained, followed by a rapid decrease in viscosity as the structure collapses. See Tabilo-Munizaga and Barbosa-Canovas, 2005, Journal of Food Engineering 67, pp. 147-156, which is hereby incorporated by reference.

In some embodiments, a second feature 212 that is measured in accordance with the systems and methods of the present disclosure using a rheometer, or viscometer, which measures the rheological properties of fluids by the resistance to flow under a known force or the produced stress by a known amount of flow, such as a capillary viscometers, a falling-ball viscometer, a rotational rheometers, or an oscillatory rheometer. See Tabilo-Munizaga and Barbosa-Canovas, 2005, Journal of Food Engineering 67, pp. 147-156, which is hereby incorporated by reference.

In some embodiments, a second feature 212 that is measured is structure or hardness (e.g., gel structure) which corresponds to a peak force during the first compression cycle in the puncture method. See Wang and Damodaran, 1991, J. Agric. Foo Chem. 39, pp. 434-438, which is hereby incorporated by reference.

In some embodiments, a second feature 212 that is measured is conformation (e.g., conformation of proteins in gels). In some such embodiments this is measured using circular dichroism. See Wang and Damodaran, 1991, J. Agric. Foo Chem. 39, pp. 434-438, which is hereby incorporated by reference.

In some embodiments, the target property is gelling speed and the second features that serve as metrics for this target property are measured by compression tests, stress relaxation tests, creep test, oscillation tests, puncture force, and texture profile analysis as summarized in Table 3 of Banerjee and Bhattacharya, 2012, "Food Gels: Gelling Process and New Applications," *Critical Reviews in Food Science and Nutrition* 52, pp. 234-346, which is hereby incorporated by reference.

Example 1: Predicting the Ability of a Protein Isolate to Gel

Goal

This example describes machine-learning models that predict food-related functional properties of novel proteins from their basic molecular properties. These models increase screening efficiency by allowing for the identification and further characterization of only the most promising protein candidates out of a massive population of potential candidates.

In this example, a model 214 was created that predicts the gelling abilities (second feature 212) of a protein (test entity 218) based on a set of molecular properties (first features 210). Gelling ability is a prominent functional feature (second feature 212) in food science because it gives the appropriate texture to food products. Thus, thermal gelling ability makes proteins valuable in many food applications. For example, in the process of making plant-based substitute for scrambled eggs, plant proteins with excellent gelling ability comparable to egg proteins are sought.

Results.

Egg proteins were chosen as reference entities 208 for the purpose of training the machine-learning models 214 because such egg proteins have known good gelling ability. The molecular (first features 210) and functional features (second features 212) of egg samples were measured to form a training set 206 in accordance with block 404 of FIG. 4A, and used to train predictive models 214 on the training set 206 in accordance with block 458 of FIG. 4D. The model 214 takes protein molecular feature data (first features 210) as input and generates a prediction of gelling ability (second feature 212) as output.

Figure 5:
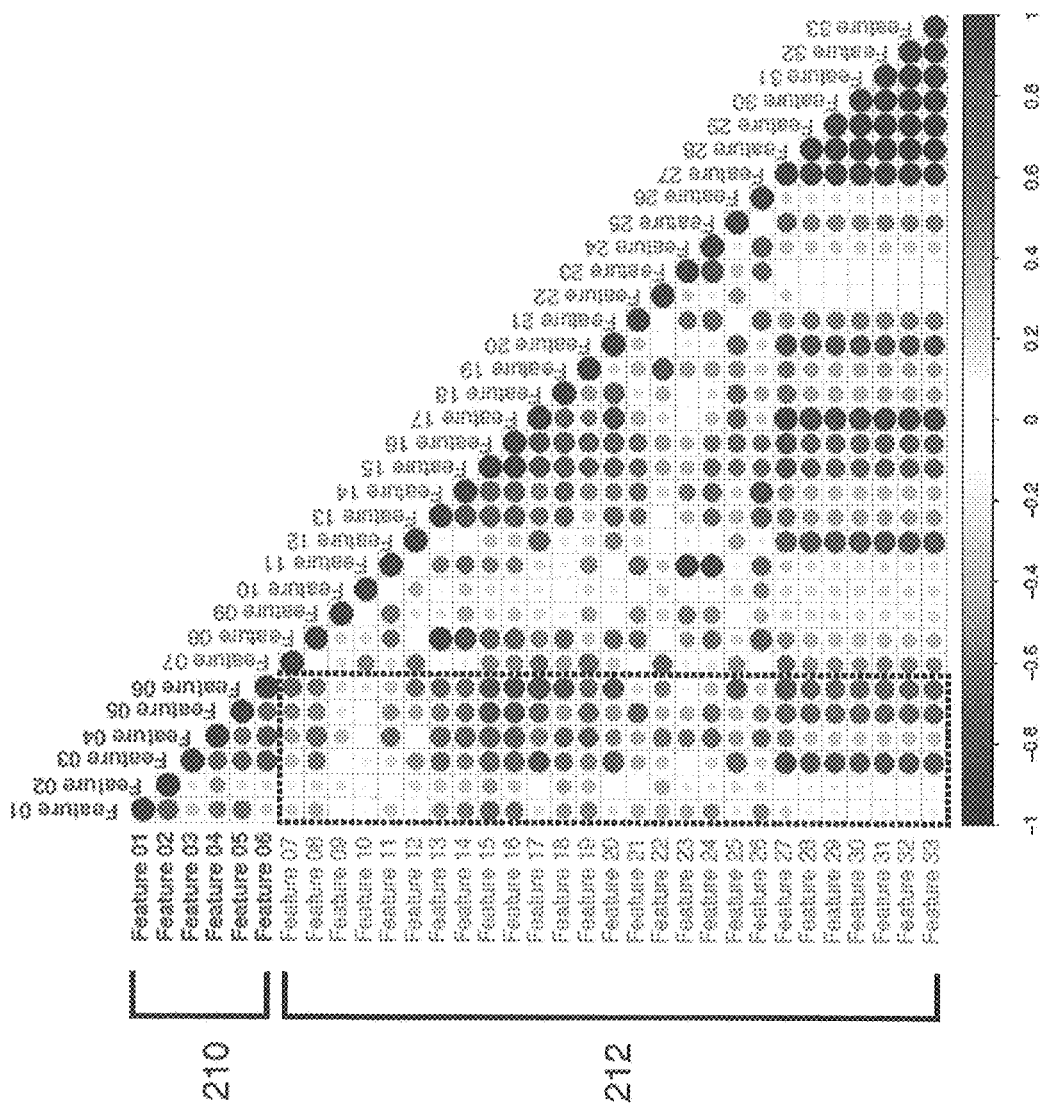
FIG. 5 illustrates the correlation between molecular features and functional features in one exemplary application of the present disclosure.

The reference entities 208 in the training set 206 comprised composite blends with various ratio of egg white and yolk (13 points uniformly sampled from an egg white gradient from 0% to 100%, plus a homogenized natural whole egg sample) for a total sample size of 42 (Q=42) (14 samples with three biological replicates each). The molecular features (first features 210) characterized for each egg protein composite blend (reference entity 208) included protein content, hydrophobicity, WBC, and phospholipid count. These molecular features served as the first features in an M-dimensional feature space. The functional features (second features 212) characterized for each egg protein composite blend (reference entity 208) includes dye penetration, viscosity, gelation, texture (small scale), texture (puck), texture (kramer cell), angled layering, layer strength, flow consistency, and gelling speed. These functional features served as the second features in an N-dimensional feature space. A total of 43 measurements were made for each reference entity 208 (egg sample), 6 molecular features and 27 functional features. Thus the training set 206 is a 42 by 33 matrix. Correlations between the molecular features (first features 210) and the functional features (second features 212) across the reference entities 208 of the training set 206 are illustrated in FIG. 5.

This training set 206 was used to train regression models using the molecular features (the first features 210) as inputs and the functional features (the second features 212) as targets in accordance with block 458 generally, and block 460 more particularly. Inputs (measurements of first features 210 in the training set 206) and targets (measurements of second features 212 in the training set) were compiled into a matrix format in which measurement values for features were represented as columns, and samples (reference entities 208) as rows. The matrix was then divided into training, validation, and testing data subsets. A total of 38 samples (reference entities 208) were reserved for the training plus validation sets (90%) of the dataset, whereas four samples were reserved for testing. During model training using the training plus validation set, a leave-one-out cross-validation procedure was used in which models 214 were trained on all the data except for one point and a prediction was made for that point, then repeated for all data points. This minimized error introduced by random data splitting. The testing set was only used for final evaluation of model performance.

Figure 6:
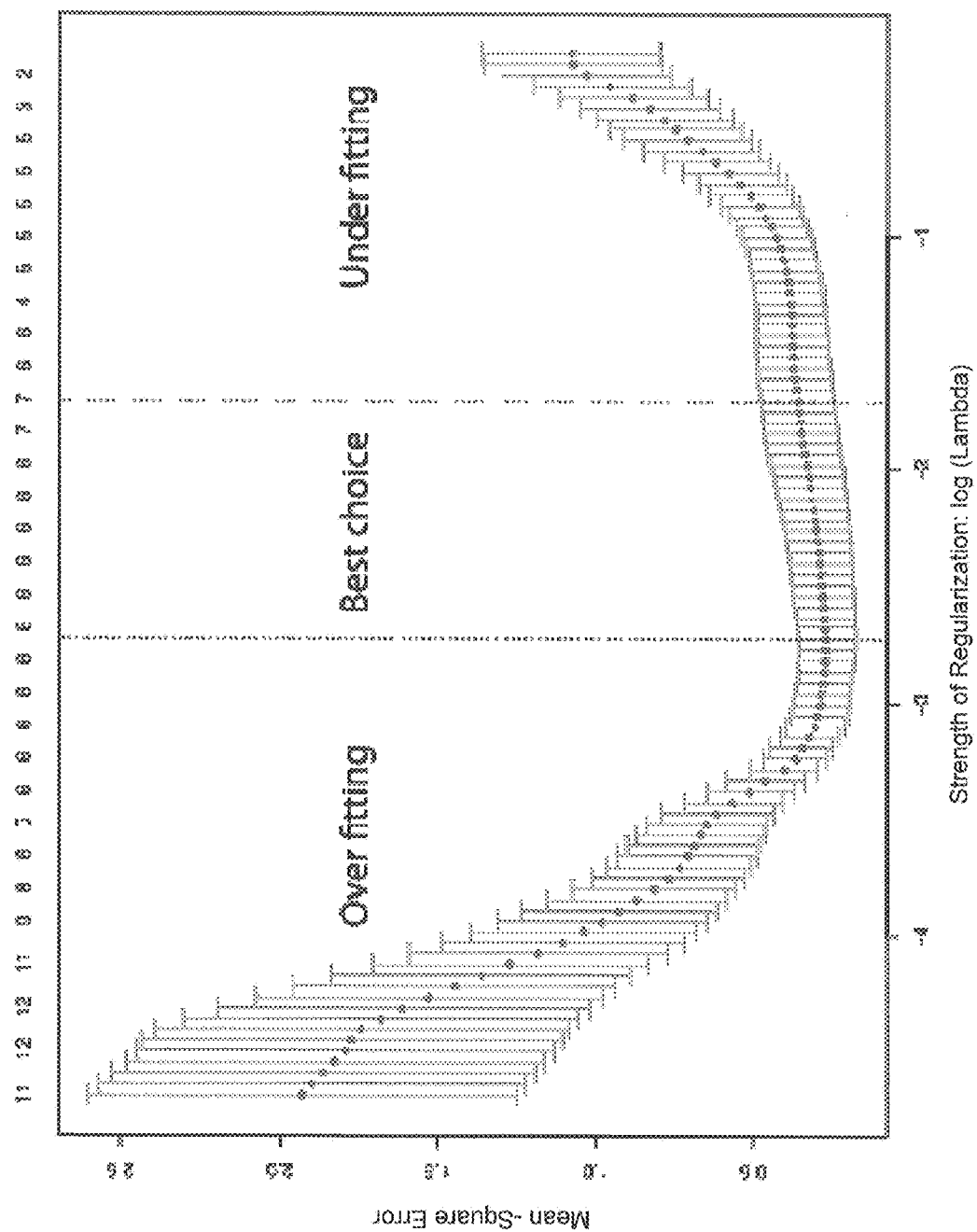
FIG. 6 illustrates model performance evaluation for a series of linear models, in which each model takes in a certain number of different molecular feature measurements (first features) as inputs and predicts gelling ability (second feature) as output, in accordance with an embodiment of the present disclosure.

Advantageously, the training set 206 afforded the ability to use different models 214, including linear regression (block 460), random forest, and Gaussian process models, for different target functionalities. Moreover, target functionalities were modeled and predicted with different prediction accuracy. Here, gelling ability is provided as an example of one such functional feature (second feature 212) that was modeled based on molecular features (first features 210) due to its relevance as a metric for the target property. FIG. 6 illustrates model performance evaluation for a series of linear models, each using a different number of molecular features, as an example. Each model takes in a certain number of different molecular feature measurements (first features) as inputs and predicts gelling ability (second feature) as output. In FIG. 6, Mean Squared Error (MSE) between prediction and validation data is used as the metric of model performance. The regularization depicted in FIG. 6 is an example of block 440 generally, and block 448 more particularly, of FIG. 4C.

Prediction.

Using models 214 trained with the egg training set 206, predictions were made on plant protein (test entity 218) gelling abilities (second feature 212), in accordance with blocks 482, 484, and 486 of FIG. 4F, and these predictions were validated experimentally. One of the positively predicted plant protein isolates (test entity 218) was successfully applied in an egg-focused food application as described below. A set of plant protein isolates (test entities 218) were screened for targeted gelling functionalities, in accordance with blocks 482, 484, and 486 of FIG. 4F, and predictions were made as to which test entities 218 would gel appropriately for an egg-substitute application.

The process in accordance with this Example 1 began with 63 features (6 molecular features and all possible interactions among them). The number of features shrinks as the strength of regularization was increased, in accordance with block 440 generally, and block 448 more specifically, of FIG. 4C. In the example of gelling ability prediction, a total of three molecular features (first features 210) and four combinations of molecular features, were determined to be the most relevant predictors in protein gelling ability prediction. See FIG. 7. In FIG. 7, colons represent the product between first features (e.g., "Feature:1:3.5" means the interaction between first feature 1, first feature 3 and first feature 5). As such, Feature 1:3:5 serves as a first feature 210. Two columns of coefficients were calculated by training models 214 under two optimal regularization strengths (lamba). Non-zero coefficients were tested significantly different from zero by t-test at the significance level of 0.05. The p-value for each of the features, or combinations thereof, selected in this Example for further use in models is provided in FIG. 7.

Validation.

Predictions were validated in two different ways in this example. First, isolates (test entities 218) identified by the trained model 214 were tested for how they layered up upon heating. Positively predicted isolates (positively predicted test entities 218) formed small layering areas, indicating their ability to gel. The gelling ability was quantified by the size of layering area of protein samples on a heated surface in an assay known as the "angled layering assay." Second, positively predicted isolates (positively predicted test entities 218) were tested in a food model that served as prototypes of egg patties. In the model, high purity plant protein isolates are rehydrated. Emulsion of plant protein isolate, oil, hydrocolloid, salt and other ingredients were prepared using a Pro Scientific shear mixer operated at 5000 RPM for four minutes at room temperature. Emulsion was deposited in round molds (3 inches diameter) in 50 gram aliquots and then heated in a convection oven at 220° F. for 55 minutes. Results show that these isolates form heat-setting gels that have texture similar to that in positive control reference entities 208 (egg proteins).

Example 2—Predicting Food Texture Performance Using Linear and Non-Linear Classification Methods Goal As a person skilled in the art will understand, food texture is one of the primary attributes which, together with color, flavor and smell, contribute to sensory quality of foods. Furthermore, it is the characteristic of quality that is valued by consumers, and its target properties are characterized by being hard to define because they are subjective characteristics. A food's texture dictates the way the food is experienced physically, and also serves as a mechanism to deliver flavor and nutrition. In that way, a product's texture is a primary determinant of a high-quality versus low-quality food product. Texture can be affected by many factors, including ingredient composition, pH, ionic strength, cooking temperature, and more. Consequently, the textural landscape can be vast, given the combinatorial possibilities of ingredients, formulations, and cooking process protocols.

This example describes the development of a model 214 that navigates textural landscapes thereby affording the prediction of which ingredients, formulations, and processing methods will result in textural qualities matching targeted outcomes. The model 214 predicts combinations of ingredients, formulations, and processes that would result in textures rivaling those found in egg-related applications.

In this example, the first features 210 of reference entities 208 of the training set 206 were measured using an instrument called a texture analyzer, which performs a texture profile analysis (TPA) on physical food samples (here, reference entities 208) via a probe used to compress the sample. TPA data was collected from two groups of reference entities 208: positive control reference entities and negative control reference entities in accordance with block 404 of FIG. 4A. This process is also called vectorization or quantification of samples (reference entities 208). As such, the class label of "positive" or "negative" served as the second feature 212 for the reference entities 208 in this example.

Models 214 were trained using textural features as first feature 210 inputs and sample group labels (positive or negative) as second features 212 in accordance with block 458 of FIG. 4D.

For this example, 538 reference entities 208 (samples), with three replicates each, were collected for a total training set 206 size of 1922. Five textural features obtained from TPA analysis were determined for each reference entity 208 and treated as first features 210. Thus, the training set 206 was a 1922 by 5 matrix. Egg-based samples served as positive controls (positive reference entities 208) in this example. However, it should be noted that other types of food products can be modeled and such other types of food products are within the scope of the present disclosure. Negative control samples (negative reference entities 208) were based on plant protein samples whose textures were a priori known to be far from that of positive reference entity 208 egg samples.

Inputs (textural features as first features 210) and targets (class labels "positive" and "negative," as the target second feature 212) of the training set 206 were compiled into a matrix format in which features (210/212) were represented as columns and samples (reference entities 208) as rows. The matrix was then divided into training, validation (1730 samples, or 90 percent of the total number of samples), and testing data subsets (192 samples, or 10 percent of the total number of samples).

The training set 206 was used for model 214 training (in accordance with block 458 of FIG. 4D), validation data for model selection, and testing data for performance evaluation. During model 214 training using the training plus validation set, a leave-one-out cross-validation procedure was employed in which models were trained on all the data except for one sample and a prediction made for that sample, and then this process was repeated for all samples in the training plus validation set. The testing set was only used for final evaluation of model 214 performance.

Model selection and model training regimens were performed to create two high performing models 214, a bagged logistic regression model and a support vector machine from five models tested under various balancing scenarios. The five models tested were random forest, ADAboost, support vector machine, bagged logistic regression, and XG Boost. Bagged logistic regression models are described in Breiman, 1996, "Bagged Predictors," Machine Learning 24, pp. 123-140, Kluwer Academic Publishers, Boston Mass., which is hereby incorporated by reference. For this Example 2, Scikit-learn, a Python module integrating a wide range of machine learning algorithms, was used. See Brucher and Perrot, 2011, "Scikit-learn: Machine Learning in Python," Journal of Machine Learning Research 12, pp. 2825-2380, which is hereby incorporated by reference, was used.

Cross-validation procedures were performed to minimize error introduced by random data splitting, and regularization methods were applied during training to reduce the chance of model overfitting.

TPA data was measured from newly generated test entities 218 as first features 220, representing different combinations of protein isolates, ingredient formulations, and cooking processes. The trained models 214 then predicted which test entities 218 match or exceeded the textures of egg-based samples without any requirement that the second feature 212 (or the ultimate target property of being a suitable egg substitute) be measured for the test entities 218.

Predictions made by the trained models on which test entities 218 had the desired value or category for the second feature 212 were validated using two approaches: computational validation and sensory validation.

Computational validation was performed by unsupervised clustering in accordance with blocks 488 and 490 of FIG. 4G. Texture feature-based clustering for all samples, both the reference entities 208 and the test entities 218 was performed regardless of their labels on the target second feature 212 and then assessments were made on which cluster is significantly enriched in egg samples. Then, a determination was made as to which plant-based samples (the test entities 218) were clustered with the egg-samples. The plant-based samples that clustered with the positive reference entity 208 egg samples were consistent with positive predictions of the trained model 214.

Sensory validation was performed by asking opinions of a trained human sensory panel. Sensory panelists were asked to rank textural properties of test entities 216 identified by the trained model 214 in double-blind experiments, and then the rankings between plant-based test entities 216 identified by the trained model 214 and egg-based positive reference entities 208 were compared. This work showed that the test entities 218 that were positively predicted by the trained model 214 developed in this example had similar texture compared to that of the positive egg based reference entity 208 samples. One of the positively predicted test entities serves as the basis of current commercial efforts to develop plant-based protein-rich products which exhibit cooking and textural properties similar to cooked chicken egg products.

Example 3—Predicting Emulsifying Properties Using a Supervised Learning Approach (Nearest Neighbors)

Goal

Emulsions, which are mixtures of two immiscible liquids, serve as the basis of many types of food products, including beverages, dressings, condiments, sauces, gravies, cakes and other batter-based goods, ice cream, whipped toppings, and many more. An emulsifying ingredient is one that allows for an emulsion to form and stabilize. In some cases, certain proteins can have emulsifying properties that allow immiscible liquids to come together in a food application.

In the present example, a model 214 was trained and implemented that allows for the prediction of the emulsifying capabilities (second feature 212) of a plant protein isolate (test entity 218) in a food system based on its molecular characteristics (first features 210/220). This model 214 reduces the search space of potential emulsifiers, as well as increases the likelihood of finding suitable emulsifiers for different food product applications.

Data.

The training set 206 used to train the model 214 in this example included quantitative measurements of a number of protein molecular characteristics (first features 210), including protein state, charge, hydrophobicity, stability, and concentration. These data are generated by assaying protein isolates (reference entities 208) using physical discovery platform instruments. In particular, ten molecular assays were used in molecular property characterization of protein isolates in accordance with block 404 of FIG. 4A. A total of 210 molecular features (first features 210) were extracted from the assays in accordance with blocks 408 and/or 410 of FIG. 4A.

A total of 76 protein isolates (reference entities 208) were characterized by the ten molecular assays and mapped onto the molecular space. Of these 76 protein isolates, 50 were created via an in-house isolation process, whereas 26 were commercially available reference proteins. The set of 210 molecular features was extracted from the characterization data. Thus, the training set 206 comprised a 76 by 210 matrix (i.e., 76 samples by 210 molecular features). The molecular features (first features 212) were compiled into a matrix format in which features are represented as columns and samples as rows. Therefore, each protein sample (reference entity 208) is represented by a vector of molecular features (first features 210).

Unsupervised principal component analysis (PCA) was used to reduce the feature dimension space while maintaining most of the variability of the data. PCA aims to find a lower dimension linear subspace in which each principal component basis is orthogonal to each other, and the data points projected to the subspace explain the maximum portion of variance in the measurements of the target second feature (or second features) across the training set as in the original space. PCA reduced the dimension from original set of first features 210 to five orthogonal principal components. Each principal component is a linear combination of the original first features. The five principal components explained 70% of total variance of the data. In other words, the five principal components explained 70% of total variance in the target second feature across the training set.

A nearest neighbor search model was developed to predict the emulsifying properties of plant protein isolates based on their molecular features in accordance with block 492 of FIG. 4G. The model 214 was created using the principal components derived from the PCA analysis of the first features 210 generated by a number of protein samples (reference entities 208), including those with known emulsifying properties. The vectors of the principal components of the samples were then plotted into a multi-dimensional space and distance metrics were defined to measure distances between the principal components of any two given samples in the molecular space, for all pairwise combinations of samples. The model allowed for the retrieval of potential emulsifiers based on their distances from known emulsifiers in the molecular space.

Figure 9:
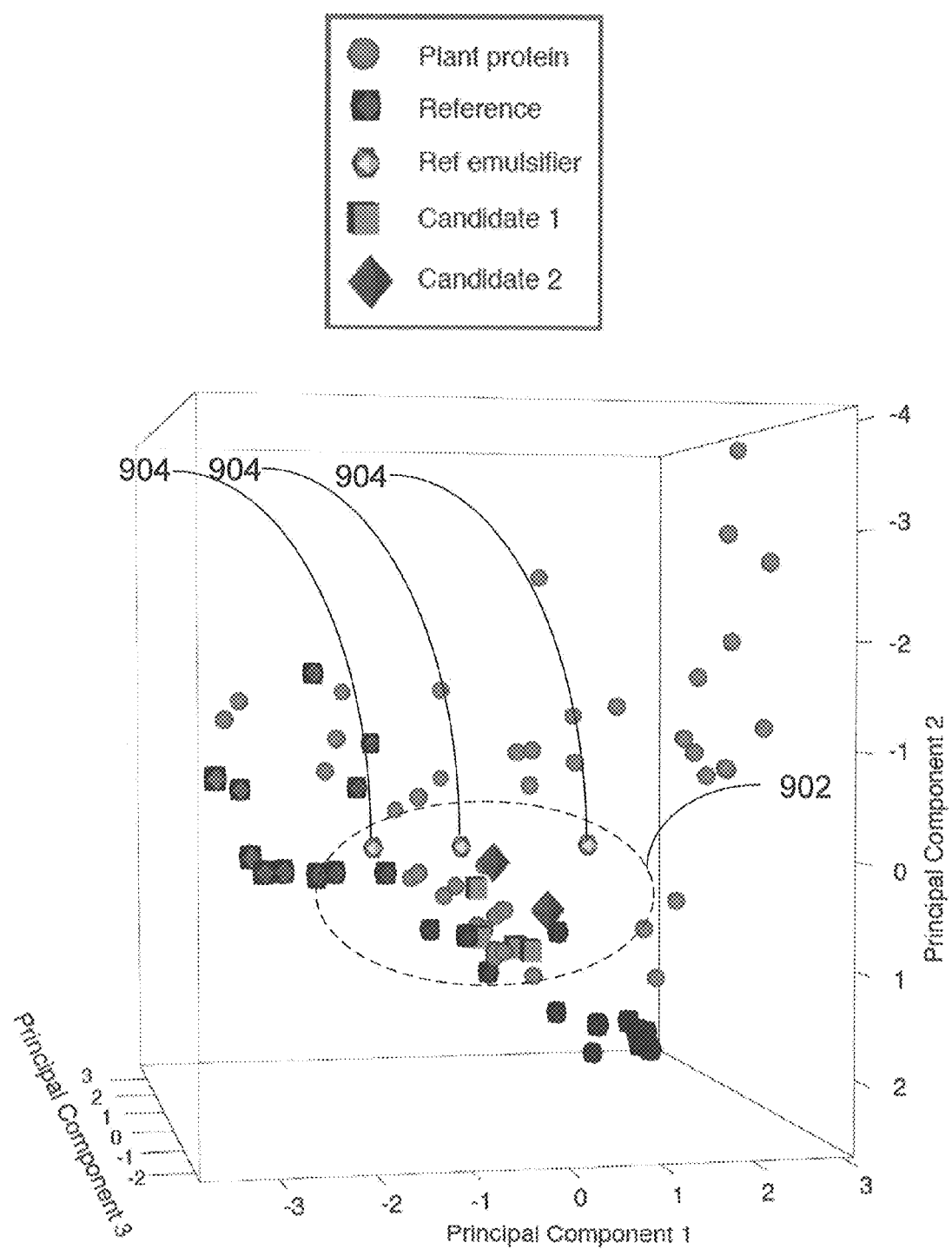
FIG. 9 illustrates the identification of potential emulsifiers by a nearest neighbor search in the molecular feature space in accordance with an embodiment of the present disclosure.

FIG. 9 illustrates the identification of two potential emulsifiers (test entities 218) by this nearest neighbor search in the molecular feature space in accordance with blocks 482, 484 and 486 of FIG. 4F. In FIG. 9, these two potential emulsifiers are denoted "Candidate 1," and "Candidate 2." In FIG. 9, it can be seen that principal components map to the same portion 902 of the molecular feature space as those of a reference emulsifier 904. In his example, each test entity was tested under multiple conditions (such as pH, buffer type, biological replicates, etc.). Thus a single test entity can have multiple (but similar) plots representing its environment-dependent variations in feature space. For this reasons, "Candidate 1" and "Candidate 2" each show up more than once in FIG. 9.

As such, the trained model 214 (the nearest neighbor analysis) afforded the identification of plant protein isolates (test entities 218) that localized closest to whey protein (a known emulsifier) in the molecular feature space, as having great potential for acting as emulsifiers.

The prediction by the model 214 that candidate 1 and candidate 2 had the unmeasured second feature, and thus were likely to have the target property, was validated by experimentally testing their emulsifying capacity and stability (second features) in physical application tests. One of the two protein candidates was found to form stable emulsions under food-appropriate conditions. This leading candidate protein isolate was applied in a condiments-related food model system to yield good results. Thus, the isolate (test entity 218) is presently being developed as an emulsifier for a number of food product lines.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, or 3 and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed:
1. A discovery system for inferentially screening a test entity to determine whether it exhibits a target property without directly measuring the test entity for the target property, the discovery system comprising:
at least one processor and memory addressable by the at least one processor, the memory storing at least one program for execution by the at least one processor, the at least one program comprising instructions for:
A) obtaining a training set that comprises a plurality of reference entities and, for each respective reference entity, (i) a respective measurement of each first feature in a respective subset of first features in an N-dimensional feature space and (ii) a respective measurement of each second feature in a respective subset of an M-dimensional feature space, wherein
N is a positive integer of two or greater,
M is a positive integer,
the training set collectively provides at least one measurement for each first feature in the N-dimensional feature space,
the training set collectively provides at least one measurement for each second feature in the M-dimensional feature space,
at least one second feature in the M-dimensional feature space is a metric for the target property,
the N-dimensional feature space does not include any of the second features in the M-dimensional space,
the M-dimensional feature space does not include any of the first features in the N-dimensional space,
the test entity comprises a protein, a fragment thereof, or a mixture of the protein with one or more other proteins,
the obtaining (A) associates the test entity with a data structure comprising one or more extraction parameters used to extract the test entity from the test member, and
the one or more extraction parameters comprises an extraction parameter in the group consisting of (i) an elution pH or time for the test entity, (ii) a buffer type used to extract the test entity from the test member, (iii) a specific pH or pH range used to extract the test entity from the test member, (iv) a specific ionic strength or an ionic strength range used to extract the test entity from the test member, and (v) a specific temperature or temperature range used to extract the test entity from the test member;
B) identifying two or more first features, or one or more combinations thereof, in the N-dimensional feature space using a feature selection method and the training set, thereby selecting a set of first features $\{p_1, \ldots, p_{N-K}\}$ from the N-dimensional feature space, wherein N−K is a positive integer less than N;
C) training a model using measurements for the set of first features $\{p_1, \ldots, p_{N-K}\}$ across the training set, thereby obtaining a trained model;
D) obtaining measurement values for the set of first features $\{p_1, \ldots, p_{N-K}\}$ of the test entity;
E) inputting the set of first features $\{p_1, \ldots, p_{N-K}\}$ of the test entity into the trained model thereby obtaining a trained model output value for the test entity; and
F) comparing the trained model output value of the test entity to one or more trained model output values computed using measurement values for the set of first features $\{p_1, \ldots, p_{N-K}\}$ of one or more reference entities that exhibits the target property thereby determining whether the test entity exhibits the target property.

2. The discovery system of claim 1, wherein the trained model is a linear regression model of the form:

$$f(X) = \beta_0 + \Sigma_{j=1}^t X_j \beta_j$$

wherein t is a positive integer,
f(X) are the measurements for a second feature in the M-dimensional feature space across the training set,
$\beta_0, \beta_1, \ldots, \beta_t$ are parameters that are determined by the training C), and
each $X_j$ in $\{X_1, \ldots, X_t\}$ is a first feature $p_i$ in the set of first features $\{p_1, \ldots, p_{N-K}\}$ of the training set, a transformation of the first feature $p_i$, a basis expansion of the first feature $p_i$, an interaction between two or more first features in the set of first features $\{p_1, \ldots, p_{N-K}\}$, or a principal component derived from one or more first features in the set of first features $\{p_1, \ldots, p_{N-K}\}$.

3. The discovery system of claim 2, wherein at least one $X_j$ in $\{X_1, \ldots, X_t\}$ represents an interaction between two or more features in the set of first features $\{p_1, \ldots, p_{N-K}\}$.

4. The discovery system of claim 2, wherein $\{X_1, \ldots, X_t\}$ is determined by the identifying B) or training C) from the N-dimensional feature space using a subset selection or shrinkage method.

5. The discovery system of claim 1, wherein the trained model is a nonlinear regression model.

6. The discovery system of claim 1, wherein
the trained model is a clustering applied to the measurements for the set of first features $\{p_1, \ldots, p_{N-K}\}$ across the training set without use of respective measurements of each second feature in the M-dimensional feature space, and
the inputting E) comprises clustering the set of first features $\{p_1, \ldots, p_{N-K}\}$ of the test entity together with the measurements for the set of first features $\{p_1, \ldots, p_{N-K}\}$ across the training set, and
the comparing F) comprises determining whether the set of first features $\{p_1, \ldots, p_{N-K}\}$ of the test entity co-clusters with the set of first features $\{p_1, \ldots, p_{N-K}\}$ of one or more reference entities in the training set that exhibit the target property.

7. The discovery system of claim 6, wherein the clustering comprises unsupervised clustering.

8. The discovery system of claim 1, wherein
the model is a k-nearest neighbors classifier,
the inputting E) and the comparing F) comprises obtaining the trained model output value as the outcome of the set of first features $\{p_1, \ldots, p_{N-K}\}$ of the test entity against the k nearest neighbors of the test entity in the training set using the trained k-nearest neighbors classifier, and
the k nearest neighbors of the test entity includes one or more reference entities that exhibit the target property.

9. The discovery system of claim 1, wherein the model is a support vector machine.

10. The discovery system of claim 1, wherein
the respective measurement of each first feature in a respective subset of first features in the N-dimensional feature space for each corresponding reference entity in the training set is taken when the corresponding reference entity is in the form of an emulsion or a liquid, and
the set of first features $\{p_1, \ldots, p_{N-K}\}$ comprises protein concentration, hydrophobicity, fat content, color, or phospholipid concentration of the corresponding reference entity.

11. The discovery system of claim 1, wherein
the respective measurement of each first feature in a respective subset of first features in the N-dimensional feature space for each corresponding reference entity in the training set is taken when the corresponding reference entity is in the form of an emulsion or a liquid, and
the set of first features $\{p_1, \ldots, p_{N-K}\}$ comprises an amount of inter- or intra-molecular bonds within the corresponding reference entity.

12. The discovery system of claim 1, wherein the training C) further comprises training the model using measurements of each corresponding reference entity in the training set for a single second feature, wherein
the single second feature is selected from the group consisting of dye penetration, viscosity, gelation, texture, angled layering, layer strength, flow consistency, and gelling speed, or
the single second feature is hardness, fracturability, cohesiveness, springiness, chewiness, or adhesiveness as determined by a texture profile analysis assay.

13. The discovery system of claim 1, wherein
N is 10 or more, and
N–K is 5 or less.

14. The discovery system claim 1, wherein the respective measurement of each first feature in the N-dimensional feature space for a single reference entity in the plurality of reference entities is obtained from a molecular assay set comprising three or more different molecular assays.

15. The discovery system of claim 1, wherein the respective measurement of each second feature in a respective subset of the M-dimensional feature space for a single reference entity in the plurality of reference entities is obtained from a functional assay set comprising three or more different functional assays of the single reference entity.

16. The discovery system of claim 1, wherein the feature selection method comprises regularization across the training set using the N-dimensional feature space and a single second feature in the M-dimensional feature space.

17. The discovery system of claim 1, wherein the feature selection method comprises application of a decision tree to the training set using the N-dimensional feature space and all or a portion of the M-dimensional feature space.

18. The discovery system of claim 1, wherein the feature selection method comprises application of a Gaussian process regression to the training set using the N-dimensional feature space and a single second feature in the M-dimensional feature space.

19. The discovery system of claim 1, wherein
the feature selection method comprises application of principal component analysis to the training set thereby identifying a plurality of principal components wherein the plurality of principal components collectively represent the set of first features $\{p_1, \ldots, p_{N-K}\}$ from the M-dimensional feature space across the training set, and
the training of the model using measurements for the set of first features $\{p_1, \ldots, p_{N-K}\}$ across the training set C) comprises training the model using the plurality of principal components samples for each reference entity in the plurality of reference entities and measurements for one or more second features in each reference sample in the training set.

20. The discovery system of claim 1, wherein
a plurality of first features in the N-dimensional feature space is obtained from a molecular assay of each reference entity in the training set, the feature selection method comprises:
- (i) application of a kernel function to the respective measurement of each measured first feature in the plurality of first features in the N-dimensional feature space for each reference entity in the plurality of reference entities thereby deriving a kernel matrix, and
- (ii) applying principal component analysis to the kernel matrix thereby identifying a plurality of principal components wherein the plurality of principal components collectively represent the set of first features $\{p_1, \ldots, p_{N-K}\}$ from the N-dimensional feature space; and the training of the model using measurements for the set of first features $\{p_1, \ldots, p_{N-K}\}$ across the training set comprises training the model using the plurality of principal components samples for each reference entity in the plurality of reference entities.

21. The discovery system of claim 1, wherein
a first plurality of first features in the N-dimensional feature space is obtained from a first molecular assay of each reference entity in the training set,
a second plurality of first features in the N-dimensional feature space is obtained from a second molecular assay of each reference entity in the training set,
the feature selection method comprises:
- (i) applying a first kernel function to the respective measurement of each measured first feature in the first plurality of first features in the N-dimensional feature space for each reference entity in the plurality of reference entities, thereby deriving a first kernel matrix,
- (ii) applying a second kernel function to the respective measurement of each measured first feature in the second plurality of first features in the N-dimensional feature space for each reference entity in the plurality of reference entities, thereby deriving a second kernel matrix, and
- (iii) applying principal component analysis to the first kernel matrix and the second kernel matrix thereby identifying a plurality of principal components wherein the plurality of principal components collectively represent the set of first features $\{p_1, \ldots, p_{N-K}\}$ from the N-dimensional feature space; and the training of the model using measurements for the set of first features $\{p_1, \ldots, p_{N-K}\}$ across the training set comprises training the model using the plurality of principal components samples for each reference entity in the plurality of reference entities.

22. The discovery system of claim 21, wherein the model is a support vector machine.

23. The discovery system of claim 1, wherein the test entity originates from a test member of the Fungi, Protista, Archaea, Bacteria, or Plant Kingdom.

24. The discovery system of claim 1, wherein
the test entity is extracted from a plant, and
the one or more data structures identify the test entity, the extraction parameter for the test entity, and a characteristic of the plant.

25. The discovery system of claim 1, wherein the one or more data structures comprises at least three extraction parameters used to extract the test entity from the test member selected from the group consisting of: (i) an elution pH or time for the test entity, (ii) a buffer type used to extract the test entity from the test member, (iii) a specific pH or pH range used to extract the test entity from the test member, (iv) a specific ionic strength or an ionic strength range used to extract the test entity from the test member, or (v) a specific temperature or temperature range used to extract the test entity from the test member.

26. The discovery system of claim 24, wherein the characteristic of the plant is a plant taxonomy feature.

27. A discovery system for inferentially screening a test entity to determine whether it exhibits a target property without directly measuring the test entity for the target property, the discovery system comprising:
at least one processor and memory addressable by the at least one processor, the memory storing at least one program for execution by the at least one processor, the at least one program comprising instructions for:
- A) obtaining a training set that comprises a plurality of reference entities and, for each respective reference entity, (i) a respective measurement of each first feature in a respective subset of first features in an N-dimensional feature space and (ii) a respective measurement of each second feature in a respective subset of an M-dimensional feature space, wherein
  N is a positive integer of two or greater,
  M is a positive integer,
  the training set collectively provides at least one measurement for each first feature in the N-dimensional feature space,
  the training set collectively provides at least one measurement for each second feature in the M-dimensional feature space,
  at least one second feature in the M-dimensional feature space is a metric for the target property,
  the N-dimensional feature space does not include any of the second features in the M-dimensional space,
  the M-dimensional feature space does not include any of the first features in the N-dimensional space, and
  the test entity comprises a mixture of two or more proteins from a single plant species,
- B) identifying two or more first features, or one or more combinations thereof, in the N-dimensional feature space using a feature selection method and the training set, thereby selecting a set of first features $\{p_1, \ldots, p_{N-K}\}$ from the N-dimensional feature space, wherein N−K is a positive integer less than N;
- C) training a model using measurements for the set of first features $\{p_1, \ldots, p_{N-K}\}$ across the training set, thereby obtaining a trained model;
- D) obtaining measurement values for the set of first features $\{p_1, \ldots, p_{N-K}\}$ of the test entity;
- E) inputting the set of first features $\{p_1, \ldots, p_{N-K}\}$ of the test entity into the trained model thereby obtaining a trained model output value for the test entity; and
- F) comparing the trained model output value of the test entity to one or more trained model output values computed using measurement values for the set of first features $\{p_1, \ldots, p_{N-K}\}$ of one or more reference entities that exhibits the target property thereby determining whether the test entity exhibits the target property.

28. The discovery system of claim 1, the at least one program further comprising instructions for repeating the obtaining D), inputting E), and comparing F) for each test entity in a plurality of test entities, wherein
each respective test entity in the plurality of test entities comprises a different protein, a different fragment thereof, or a mixture of the different protein with one or more other proteins.

29. The discovery system of claim 28, wherein the plurality of test entities comprises more than 50 different test entities each from a single plant species.

\* \* \* \* \*